United States Patent
Dong et al.

(10) Patent No.: US 11,911,513 B2
(45) Date of Patent: *Feb. 27, 2024

(54) CONTROLLED-RELEASE SYSTEM OF ACTIVE PHARMACEUTICAL INGREDIENT AND PREPARATION METHOD THEREFOR

(71) Applicant: SHANGHAI WD PHARMACEUTICAL CO., LTD, Shanghai (CN)

(72) Inventors: Liang Chang Dong, Shanghai (CN); Xishan Chen, Shanghai (CN); Jingmin Shi, Shanghai (CN); Danyong Zhang, Shanghai (CN); Gang Wu, Shanghai (CN)

(73) Assignee: SHANGHAI WD PHARMACEUTICAL CO., LTD, Shanghai (CN)

( * ) Notice: Subject to any disclaimer, the term of this patent is extended or adjusted under 35 U.S.C. 154(b) by 567 days.

This patent is subject to a terminal disclaimer.

(21) Appl. No.: 17/101,706

(22) Filed: Nov. 23, 2020

(65) Prior Publication Data

US 2021/0169811 A1  Jun. 10, 2021

Related U.S. Application Data

(63) Continuation-in-part of application No. PCT/CN2019/088084, filed on May 23, 2019.

(30) Foreign Application Priority Data

May 23, 2018 (CN) .......................... 201810503654.4
Sep. 17, 2020 (CN) .......................... 202010980311.4

(51) Int. Cl.
| | | |
|---|---|---|
| A61K 9/28 | (2006.01) | |
| A61K 31/198 | (2006.01) | |
| A61K 9/00 | (2006.01) | |
| A61K 9/20 | (2006.01) | |
| A61K 45/06 | (2006.01) | |

(52) U.S. Cl.
CPC ............ *A61K 9/284* (2013.01); *A61K 9/0004* (2013.01); *A61K 9/2018* (2013.01); *A61K 9/2054* (2013.01); *A61K 9/2866* (2013.01); *A61K 31/198* (2013.01); *A61K 45/06* (2013.01)

(58) Field of Classification Search
CPC .... A61K 9/284; A61K 9/0004; A61K 9/2018; A61K 9/2054; A61K 9/2866; A61K 31/198; A61K 45/06; A61K 9/2886
See application file for complete search history.

(56) References Cited

U.S. PATENT DOCUMENTS

| | | |
|---|---|---|
| 908,608 A | 1/1909 | Pullen |
| 3,845,770 A | 11/1974 | Theeuwes et al. |
| 3,916,899 A | 11/1975 | Theeuwes et al. |
| 4,140,760 A | 2/1979 | Withington |
| 4,167,558 A | 9/1979 | Sheth et al. |
| 4,193,985 A | 3/1980 | Bechgaard et al. |
| 4,327,725 A | 5/1982 | Cortese et al. |
| 4,434,153 A | 2/1984 | Urquhart et al. |
| 4,612,008 A | 9/1986 | Wong et al. |
| 4,735,804 A | 4/1988 | Caldwell et al. |
| 4,900,557 A | 2/1990 | Dell et al. |
| 5,002,772 A | 3/1991 | Curatolo et al. |
| 5,068,109 A | 11/1991 | Foldager et al. |
| 5,232,704 A | 8/1993 | Franz et al. |
| 5,750,585 A | 5/1998 | Park et al. |
| 5,972,389 A | 10/1999 | Shell et al. |
| 6,120,803 A | 9/2000 | Wong et al. |
| 6,207,197 B1 | 3/2001 | Illum et al. |
| 6,261,601 B1 | 7/2001 | Talwar et al. |
| 6,660,300 B1 | 12/2003 | Bristol-Myers |

(Continued)

FOREIGN PATENT DOCUMENTS

| | | |
|---|---|---|
| CN | 1997421 A | 7/2007 |
| CN | 101926785 A | 12/2010 |

(Continued)

OTHER PUBLICATIONS

Second Office Action dated May 11, 2022 issued in CN Patent Application No. 201980031345.4, with English translation, 7 pages.
First Office Action dated Dec. 17, 2021 issued in CN Application No. 201980031345.4, with English translation, 12 pages.
Notice of Reasons for Refusal dated Nov. 2, 2021 issued in Japanese Patent Application No. 2020-564855, with English translation, 7 pages.
Extended European Search Report dated Jul. 1, 2021 issued in counterpart European Application No. 19808333.9, 9 pages.

(Continued)

*Primary Examiner* — Aradhana Sasan
(74) *Attorney, Agent, or Firm* — FOLEY & LARDNER LLP

(57) ABSTRACT

Disclosed are a controlled-release dosage form with an absorption window in the upper gastrointestinal tract and a preparation method therefor, wherein the controlled-release dosage form comprises a controlled-release platform and a retention platform. The controlled-release platform is a pharmaceutical composition comprising a tablet core and a coating membrane; and the retention platform holds the controlled-release platform in the oral cavity. The operation steps of the controlled-release dosage form are as follows: placing the controlled-release platform in the retention platform, and fixing the retention platform on matching teeth in the oral cavity; taking out the controlled-release dosage form after 4-24 hours and replacing same with a new controlled-release platform; and re-fixing the retention platform on the matching teeth in the oral cavity to achieve the sustained and stable release of drugs.

19 Claims, 13 Drawing Sheets

(56) References Cited

U.S. PATENT DOCUMENTS

| | | |
|---|---|---|
| 6,685,962 B2 | 2/2004 | Friedman et al. |
| 8,377,474 B2 | 2/2013 | Hsu et al. |
| 8,454,998 B2 | 6/2013 | Hsu et al. |
| 8,557,283 B2 | 10/2013 | Hsu et al. |
| 9,086,079 B2 | 7/2015 | Cho |
| 9,439,851 B2 | 9/2016 | Dharmadhkari et al. |
| 10,328,044 B2 | 6/2019 | Heller |
| 2005/0030552 A1 | 2/2005 | Boheim et al. |
| 2006/0204578 A1* | 9/2006 | Vergez ............ A61K 9/0004 514/23 |
| 2007/0196396 A1 | 8/2007 | Pilgaonkar et al. |
| 2008/0095840 A1 | 4/2008 | Gan et al. |
| 2016/0278899 A1* | 9/2016 | Heller ............ A61P 25/16 |
| 2021/0015737 A1* | 1/2021 | Dong ............ A61K 31/522 |

FOREIGN PATENT DOCUMENTS

| | | |
|---|---|---|
| EP | 0389224 A1 | 9/1990 |
| JP | H05500223 A | 1/1993 |
| JP | 2013544850 A | 12/2013 |
| WO | 91/03235 A1 | 3/1991 |
| WO | 9102518 A1 | 3/1991 |
| WO | 2006072940 A2 | 7/2006 |
| WO | 2007096906 A2 | 8/2007 |
| WO | 2012075473 A1 | 6/2012 |
| WO | 2015054302 A1 | 4/2015 |

OTHER PUBLICATIONS

International Search Report dated Aug. 9, 2019 issued in International Patent Application No. PCT/CN2019/088084, with English translation, 10 pages.

Written Opinion of the International Searching Authority dated Aug. 9, 2019 issued in International Patent Application No. PCT/CN2019/088084, with English translation, 10 pages.

Fahn, S., "The spectrum of levodopa-induced dyskinesias," Ann Neurol, Apr. 2000; 47(4 Suppl 1):S2-9, 1 page.

Golbe, MD, Lawrence I., "Young-onset Parkinson's disease: A clinical review," Neurology, 1991, vol. 41, pp. 168-173.

Marconi, Roberto, et al., "Subthalamic nucleus stimulation in Parkinson's disease," Neurol Sci, 2008, vol. 29, S389-S391.

Voon, MD, Valerie, et al., "Deep Brain Stimulation: Neuropsychological and Neuropsychiatric Issues," Movement Disorders, 2006, vol. 21, Suppl. 14, S305-S326.

Nyholm, D., et al., "Stable levodopa plasma levels with jejunal infusion of levodopa-carbidopa intestinal gel in advanced Parkinson's disease patients," [abstract], Movement Disorders, 2012, vol. 27, Suppl 1:410.

* cited by examiner

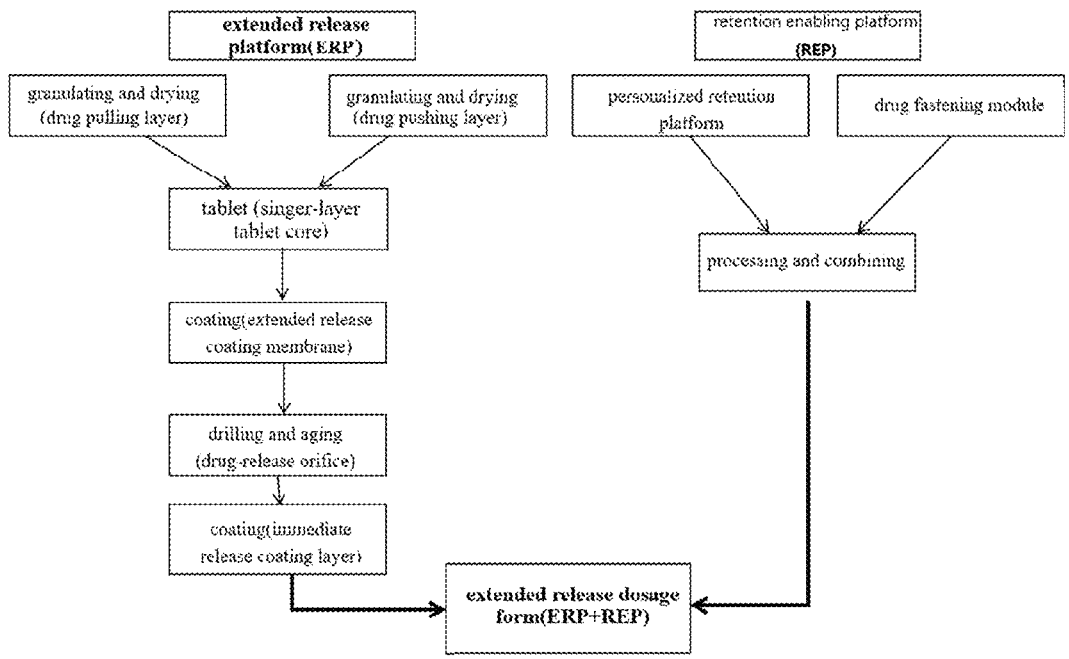
FIG. 3C
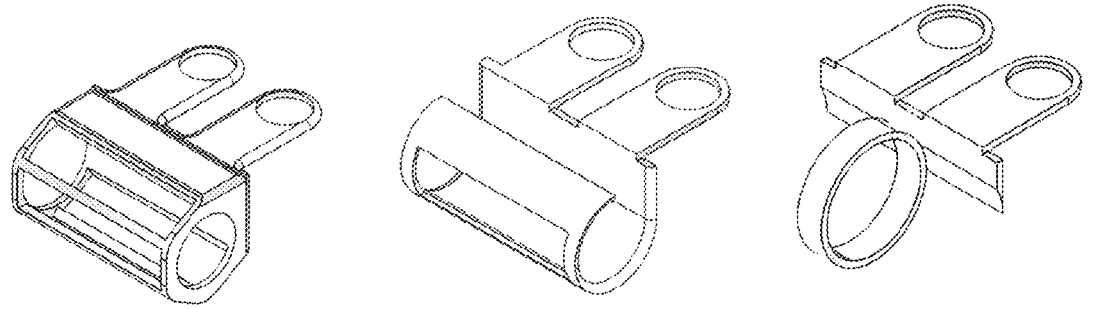
FIG. 4A      FIG. 4B      FIG. 4C
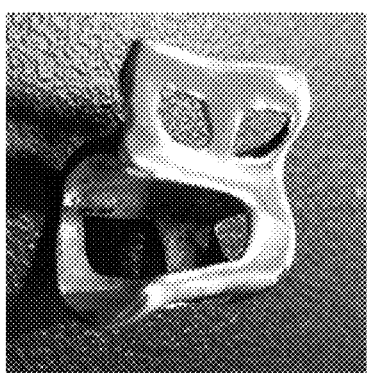 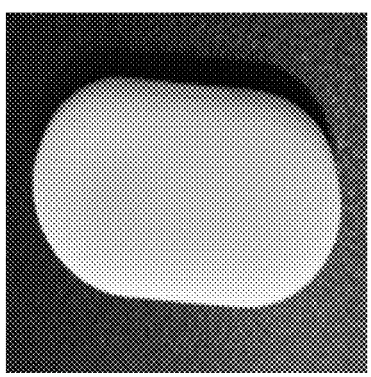 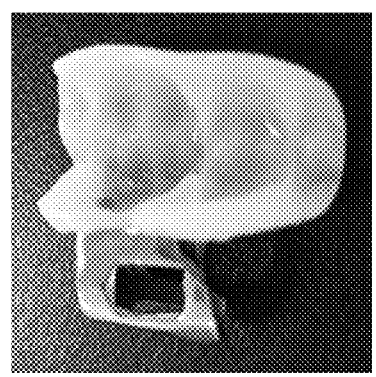
FIG. 4D      FIG. 4E      FIG. 4F

CONTROLLED-RELEASE SYSTEM OF ACTIVE PHARMACEUTICAL INGREDIENT AND PREPARATION METHOD THEREFOR

CROSS REFERENCE TO RELATED APPLICATIONS

The present application is a Continuation in part of PCT/CN2019/088084, filed May 23, 2019, which is based upon and claims priority of Chinese Patent Application CN201810503654.4 filed on May 23, 2018 and Chinese Patent Application No. 202010980311.4 filed on Sep. 17, 2020, which are hereby incorporated by reference in their entireties.

FIELD OF INVENTION

The present invention relates to the fields of biopharmaceuticals and medical devices. Specifically, it relates to a controlled-release system of active pharmaceutical ingredients and a preparation method thereof.

PRIOR ARTS

A great number of active pharmaceutical ingredients (APIs), including levodopa (LD), carbidopa (CD), baclofen, acyclovir, valacyclovir, ganciclovir, metformin, gabapentin, etc., have an absorption window limited at the upper gastrointestinal tract. The incorporation of these APIs into conventional extended-release dosages will not only result in compromised bioavailability, but also lead to failure of achieving prolonged therapeutic coverage. Therefore, a number of technologies have been disclosed in the prior art to extend the retention time in the stomach. These technologies include: expansion (U.S. Pat. Nos. 4,735,804, 5,002,772 and 6,685,962), swelling (U.S. Pat. Nos. 4,434,153, 5,750,585, 5,972,389, 6,120,803, 6,660,300 B1, US 2007/0196396A1 and U.S. Pat. No. 9,439,851), floating (U.S. Pat. Nos. 4,167,558, 5,232,704 and 6,261,601), raft-forming (U.S. Pat. Nos. 4,140,760 and 5,068,109), sinking (U.S. Pat. Nos. 4,193,985 and 4,900,557) and muco-adhesion (U.S. Pat. No. 6,207,197 and US2005/030552), etc. The technologies described above have very limited success, especially when oral dosage forms using these technologies are administered at fasting state. Therefore, there is a need for a novel controlled release system or drug controlled release system that could provide prolonged exposure to these active pharmaceutical ingredients with their absorption window limited at the upper gastrointestinal tract. The oral retention device and these drugs are combined to form a drug-device composition to form an oral retention drug delivery system, which can provide long-term exposure to these drugs with their absorption window limited to the upper gastrointestinal tract.

One of these active pharmaceutical ingredients is levodopa, which is used for the treatment of Parkinson's disease. Parkinson's disease is a progressive disease which results from the loss of dopamine-producing cells in the brain. Dopamine is a substance that is naturally present in the brain and spinal cord. Dopamine helps the nerve cells in the brain properly control the movement function. As the level of dopamine in the brain gets lower, the symptoms of Parkinson's disease appear, for example, muscle stiffness, slow movements and difficulty of keeping one's balance. Dopamine cannot penetrate the blood-brain barrier (BBB), which is the reason why oral dosage form of dopamine does not work. Levodopa is the precursor of dopamine, which can penetrate the BBB and convert into dopamine in brain tissue. Levodopa therapy is still a "gold standard" for treatment of Parkinson's disease, and almost all PD patients receive LD treatment at certain stage of the disease. However, most levodopa is decarboxylated to dopamine before reaching the brain. Therefore, LD is usually administered with decarboxylase inhibitors such as carbidopa or benserazide to prevent the formation of peripheral dopamine. LD/CD treatment can increase the content of dopamine in the brain and alleviate the symptoms of Parkinson's disease.

Despite oral administration of LD drugs, patients often develop into motor complications in the form of fluctuating—so-called "on-off" phenomena—and involuntary movements (dyskinesia) (Fahn S. The spectrum of levodopa-induced dyskinesias. Ann Neurol 2000; 47 [suppl 1]:2-11 and Golbe L I. Young-onset Parkinson's disease: a clinical review. Neurology 1991; 41:168-73.). The reason of this fluctuation can be attributed to the short half-life of LD, resulting in non-physiological, pulsatile stimulation of Post-synaptic dopamine receptors in the striatum. In addition, the therapeutic window is becoming narrower as the PD is progressing, implying that patients with advanced PD are more likely to develop akinasia and dyskinesia.

Theoretically, an extended release oral dosage form could provide a steady plasma concentration of LD for prolonging therapeutic coverage, thus alleviating the "on-off" phenomenon. In fact, due to the limited absorption of LD at the proximal gastrointestinal tract, it is a great challenge to develop an extended release LD dosage form. The residence time of the dosage form at the proximal gastrointestinal tract is approximately 3-4 hours. Therefore, any amount of LD released longer than 3-4 hours will not be absorbed and ends up in fecal material. U.S. Pat. No. 9,086,079, 908,608, 8,557,283, 8,454,998 and 8,377,474 disclose the use of organic acids to prolong the LD absorption time, thus leading to an extended release dosage form with an absorption duration of approximately 4-5 hours. Products using these patented formulations, such as Rytary, are suitable for the treatment of early and moderate Parkinson's disease.

Treatment of patients with advanced Parkinson's disease remains a medical challenge. Deep brain stimulation (DBS) (Marconi R, Landi A, Valzania F. Subthalamic nucleus stimulation in Parkinson's disease. Neurol Sci 2008; 29 Suppl 5: S389-91) and continuous intestinal LD infusion to the duodenum (DUOPA) are currently the method for the treatment of advanced PD patients who have experienced unsatisfactory effect with oral dosage forms. Since DBS involves a brain surgery, this treatment is very invasive and usually intimidating most patients. In addition, DBS also carries a risk of neuropsychiatric side effects (Voon V, Kubu C, Krack P et al; Deep brain stimulation: neuropsychological and neuropsychiatric issues. Mov Disord 2006; 21 [Suppl. 14]: S305-27). DUOPA includes a gel formulation that is administered with a pump via a tube, directly into the upper small intestine throughout the day. Continuous intestinal LD infusion into the duodenum can maintain consistent LD plasma levels for 16 hours, providing a more sustained stimulation of dopamine receptors, thus reducing motor and non-motor complications associated with pulsatile dopaminergic stimulation produced by current oral medications (Nyholm, D., Odin, P., Johansson, A., Chatamra, K., Locke, C., Freeman, S., et al; Stable levodopa plasma levels with jejunal infusion of levodopa-carbidopa intestinal gel in advanced Parkinson's disease patients [abstract]. Movement Disorders 2012; 27 Suppl 1:410).

However, the DUOPA therapy is extremely invasive. Surgery or percutaneous endoscopic gastrostomy is necessitated for the placement of a small tube to the duodenum (Health Canada Fact Sheet for DUODOPA). For some patients, a portable pump can be cumbersome. Other issues may also occur, including sporadic blockage of tubes, displacement of the internal tube, leakage at the tube connection and local infections. In addition, the DUOPA gel formulation is unstable; it has to be stored in a refrigerator (2° C.-8° C.) to minimize the degradation products, especially hydrazine, which is known to be genotoxic and possibly carcinogenic. Even at the refrigerated condition, the shelf life of the product is still very short, only 15 weeks (DUODOPA Prescription Insert). Finally, high costs may be a limiting factor. Treatment with DUOPA is expensive and requires an expert team including neurologists, gastroenterologists, nurses as well as an outbound contact to cooperate in the care of patients.

At present, there are not many related research on oral retention devices. patent application U.S. Ser. No. 10/668,274 and patent application CN 1997421 A disclose an oral drug-containing container based on an electrically controlled drug release mechanism, by which the drug release is electrically controlled, and which does not involve the problem of insertion of medicinal tablets. Moreover, the drug-containing container and the electric control system claimed in this patent are difficult to implement. There is no example in the patent specification, and it does not explain how to realize, based on the mechanism of electrically controlled drug release, the controlled release of an osmotic pump tablet as a drug storage device to achieve the drug absorption in the upper gastrointestinal tract, thereby achieving the long-term stable blood concentration.

In addition, CN 1925823 A discloses a dental bracket by which a fluoride pellet is attached to the teeth to improve the treatment and/or prevention of dental caries. This patent application neither involves the drug absorption in the upper gastrointestinal tract and the long-term stable blood concentration, nor does it involve the way of insertion of medicinal tablets.

In addition, Chinese Patent Application No. CN 105873631 A discloses an oral retention device that needs an electronic pump or a mechanical pump for administration by external power, which does not involve the insertion method of medicinal tablets.

By means of inserting a medicinal tablet from the front to the back (in a direction from the incisors to the molars), the medicinal tablet is easy to slip off from the front of the device (the incisor side), and the patient is likely to suffocate due to accidentally swallowing the dropped medicinal tablet.
Content of the Present Invention The technical problem to be solved in the present invention is to provide a controlled-release system of active pharmaceutical ingredients and a preparation method thereof so as to overcome the defect that the current extended release drugs cannot provide a prolonged and a steady plasma profiles of active pharmaceutical ingredients; and to avoid the potential precipitation of cellulose acetate during the coating process of the release-controlling membrane so as to solve the defects of uneven membrane coating and drug release.

To solve the above technical problems, one of the technical solutions of the present invention is: an extended release dosage form with an absorption window at the upper gastrointestinal tract, wherein the extended release dosage form comprises an extended release platform and a retention enabling platform;

The extended release platform (ERP) is a pharmaceutical composition comprising a tablet core and a coating membrane, wherein the tablet core comprises a drug-containing layer, and the coating membrane comprises cellulose acetate and copovidone, wherein the weight of the cellulose acetate is 50-70% of the weight of the coating membrane, and the weight of the copovidone is 30-50% of the weight of the coating membrane;

The function of the retention enabling platform is to maintain the extended release platform in the oral cavity. At least one end of the retention enabling platform is connected with a cover, so that the extended release platform can maintain in the retention enabling platform.

In order to solve the technical problem of the defect of low bioavailability due to the short residence time of the active pharmaceutical ingredients in the stomach, the present disclosure provides a new oral retention device that retains a medicinal tablet in the oral cavity without easily dropping out. Specifically, the present disclosure provides an oral retention device, with a medicinal tablet being inserted in a way from back to front such that, because the back side of the device is close to the throat, and due to blocking by the oral tissues, such as the buccal fat pad tip and the pterygomandibular folds, the medicinal tablet will not easily drop out from the device in the oral cavity, which will not cause suffocation due to accidental swallowing.

The present disclosure provides an oral retention device comprising a tooth matching component and a drug-loaded component, the tooth matching component being connected to the drug-loaded component, wherein the tooth matching component is used to bridge a tooth in the oral cavity and matches with the tooth, and the drug-loaded component can hold at least one medicinal tablet and is used to retain the medicinal tablet in the oral cavity. The oral retention device is similar to the retention enabling platform described above, but does not contain a cover.

In some preferred embodiments, the copovidone is prepared by the following method, which comprises the following steps: polymerizing vinylpyrrolidone and vinyl acetate, and the weight of the vinylpyrrolidone and the vinyl acetate is in the ratio of 40:60-80:20. Preferably, the weight of the vinylpyrrolidone and the vinyl acetate is in the ratio of 50:50-70:30. More preferably, the weight ratio of the vinylpyrrolidone and the vinyl acetate is in the ratio of 60:40.

Preferably, the retention enabling platform comprises a personalized retention enabling module and a drug fastened module, the drug fastened module can fasten the extended release platform, and the personalized retention enabling module can maintain the drug fastened module in the oral cavity.

More preferably, the drug fastened module is one or more reservoirs. In one embodiment, the reservoir is in a basket structure. In another embodiment, the shape of the cross section of the reservoir is polygon, circular closed-loop or circular open-loop, or a combination thereof.

Preferably, at least one end of the reservoir is connected with a cover, so that the extended release platform can be maintained in the reservoir; more preferably, the cover is a strip.

Preferably, the retention enabling module can be fitted to any one or more teeth in the oral cavity. Preferably the mandibular permanent teeth. More preferably the mandibular molar. Most preferably the mandibular second molar and its anterior and posterior molar.

The retention enabling module can be customized to fit and wrap, clamp or insert the entire maxillary tooth or the entire mandibular permanent tooth; preferably wrap, clamp or insert the mandibular permanent tooth; more preferably wrap the mandibular molar; most preferably wrap, clamp or insert the second mandibular molar and its adjacent parts of the first molar and the second bicuspid.

When the retention enabling platform is an oral retention device, the personalized retention enabling module can be a tooth matching component, and the drug fastened module is equivalent to drug-loaded component. In a preferable embodiment, the tooth matching component and the drug-loaded component are connected on respective sides; and/or the drug-loaded component has a reticular structure or a nonreticular structure, and the drug-loaded component has cross section in the shape of a circular, elliptical, polygonal, or special-shaped closed ring or open ring structure or a combination thereof. The cross section is a cross section perpendicular to a direction of the long axis of the tooth matching component (the direction of the long axis of the tooth matching component is substantially equivalent to the horizontal plane formed after matching of the tooth matching component and the teeth in the oral cavity).

In a preferable embodiment, the drug-loaded component comprises at least one ring body and at least one retainer, or the drug-loaded component is constituted by at least one retainer; wherein the ring body has an opening for insertion of a medicinal tablet, and the retainer has a structure for limiting the medicinal tablet in the drug-loaded component.

In a preferable embodiment, the opening faces the molars in a horizontal direction formed by the molars and the incisors, and is used to enable the medicinal tablet to be inserted from the molars toward the incisors in the horizontal direction; or the opening is provided in a direction perpendicular to the horizontal direction such that the medicinal tablet is inserted down from the above in the direction perpendicular to the horizontal direction; or the opening faces the buccal side in a direction perpendicular to the horizontal direction such that the medicinal tablet is inserted from the buccal side to the lingual side in the direction perpendicular to the horizontal direction. The horizontal direction herein is substantially equivalent to the horizontal direction in which the longest axis of the tooth matching component is located when the oral retention device is placed horizontally, and is also substantially equivalent to the horizontal direction in which the oral retention device and the longest axis of the tooth matching component are located after the oral retention device matches with the teeth in the oral cavity of the subject via the tooth matching component.

Preferably, the form of the medicinal tablet of the present disclosure does not change with time, and the medicinal tablet is an osmotic pump tablet. In a preferable embodiment, the osmotic pump tablet contains an active drug and adjuvants. The active drug has ingredients of one of levodopa or its ester, carbidopa, baclofen, acyclovir, valaciclovir, ganciclovir, metformin, and gabapentin, or one or two of levodopa or its ester and carbidopa. The medicinal tablet is a membrane-controlled medicinal tablet, wherein a controlled-release membrane is a water-insoluble cellulose acetate adjuvant, a tablet core is supported by an insoluble adjuvant matrix or by a propellant, and after the medicinal tablet is completely released in the oral cavity, the medicinal tablet is still of a complete medicinal tablet shape in appearance.

Preferably, the ring body is an open ring body or a closed ring body.

Preferably, the closed ring body is a circular, elliptical, polygonal, or special-shaped closed ring body; and the open ring body is a circular, elliptical, polygonal, or special-shaped open ring body with part thereof missing (non-closed).

In a preferable embodiment, the retainer is of a circular arc hollow or solid shape, or the retainer is formed by connecting a closed ring body and a semicircular part perpendicular to the closed ring body; and/or the retainer abuts with the ring body, or the retainer and the ring body are arranged at an interval.

Preferably, the retainer and the ring body are abutted by means of integral molding or are connected together by a connecting structure.

In a preferable embodiment, the retainer is provided as one retainer that is located on the incisor side in the horizontal direction; and/or the ring body is provided as one ring body that is located on the molar side in the horizontal direction formed by the molars and the incisors.

Preferably, the tooth matching component can match with any one or more teeth in the oral cavity, and/or the tooth matching component has a length equal to the length of 2-5 teeth.

Preferably, the teeth are mandibular permanent teeth. Preferably, they are mandibular molars. Most preferably, they are the first molar and the second molar, or are the first molar, the second molar and the second premolar, or are the first molar, the second molar and the third molar, or are the first molar, the second molar, the third molar and the second premolar.

Preferably, the tooth matching component is prepared according to the size and shape of the individual teeth. The tooth matching component is wrapped, embedded, fitted, or inserted into the tooth that matches with the tooth matching component.

The extended release platform of the present invention is an osmotic pump delivery system including LD and CD. The osmotic pump delivery system can be a single-layer elementary osmotic pump or a two-layer push-pull system. Osmotic pump delivery system could provide constant release of LD/CD in the oral cavity, which is in sharp contrast with matrix extended release system that is susceptible to the conditions in oral cavity such as pH, saliva availability and voluntary or involuntary rubbing of the hydrated matrix tablets by tongue.

The retention enabling platform (REP) of the present invention is a personalized ERP retainer that enables to fasten the ERP in oral cavity. Therefore, LD/CD can be released near the throat and readily swallowed to the stomach. The REP is a kind of REP with security features, which can prevent the accidental blockage of the extended release system. In the present invention, the "personalized" refers to the preparation of the retention enabling platform or retention enabling module that enables to fasten ERP in the oral cavity and fit to the shape of one or more teeth or the whole maxillary teeth or the whole mandibular teeth of the patient according to the shape of the teeth of the patient.

To solve the above technical problems, one of the technical solutions of the present invention is: a preparation method of the extended release dosage form, and the preparation method of the retention enabling platform or the oral retention device comprises 3D printing, injection molding or impression molding. By combining oral scanning, CAD/CAM design and preparation method, REP can be accurately and rapidly prepared according to the image of individual oral scanning.

Wherein, the working principle of 3D printing is basically the same as that of ordinary printer, except that the printing materials are different. The printing materials of ordinary printers are ink and paper, while 3D printers are equipped with different "printing materials" such as metal, ceramics, plastic, sand, etc. After the printer is connected with the computer, the "printing materials" can be stacked layer upon layer through computer control, thereby making the blueprint on the computer into a real object in the end. 3D printing refers to the technical principles of ordinary printers, in which the process of layering is very similar to inkjet printing. This printing technology is called 3D stereo printing technology. There are many different technologies for 3D printing, which differ in that modules are created by using available materials and different layers. Common materials for 3D printing are nylon glass fiber, polylactic acid, ABS resin, durable nylon material, gypsum material, aluminum material, metal titanium, titanium alloy, stainless steel, silver plating, gold plating, cobalt chromium alloy, cobalt chromium molybdenum alloy or rubber material. 3D printing is advantageous in that the automated operation can be implemented, the production speed is fast, the design blueprint in the computer can be directly and accurately converted into a physical model, and it is also suitable for small-scale custom manufacturing.

The method for preparing the oral retention device according to the first aspect of the present disclosure is 3D printing, comprising the following steps:
(1) in preferable design software 3 Shape Dental System, adding a saved drug-loaded component plan, assembling the plan with a tooth matching component plan to form an integrated oral retention device plan, and exporting a 3D printable file;
(2) importing the 3D printable file into a 3D printer, and printing the oral retention device; wherein the 3D printing preferably uses a laser sintering process;
preferably, before the step (1), the following steps are included: (0) in preferable software SolidWorks, designing the drug-loaded component plan according to the data of the size of the medicinal tablet, and saving the plan; and/or in the design software 3 Shape Dental System, designing the tooth matching component plan according to the data of the size of teeth of the subject; and
more preferably, the data of the size of the medicinal tablet and/or the data of the tooth of the subject are obtained by means of scanning with a scanner, and the scanner is preferably 3 Shape TRIOS® scanner.

In a specific embodiment, a "3 Shape TRIOS®" intraoral scanner was used to scan the data of size of a medicinal tablet, the data was then imported into the software "SolidWorks", a plan of a drug-loaded component that can load the drug part, and the plan was created and saved as a "standard attachment" file; the "3 Shape TRIOS®" intraoral scanner was used to scan the teeth of the subject, the data was imported into the software "3 Shape Dental System", and a tooth matching component was designed according to the data of teeth; on the software "3 Shape Dental System", the "standard attachment" was added and assembled with the tooth matching component to form an integrated oral retention device, and a 3D printable file was exported; and the 3D printable file was imported into the 3D printer, and the oral retention device was printed. The 3D printing preferably uses a laser sintering process.

Injection molding is a method of injecting and molding, that is, at a certain temperature, the polymer material that is completely molten is stirred by a screw, injected into a mold cavity with high pressure, and cooled and solidified to get the molding products. This method is suitable for mass production of complex shape parts and is one of the important processing methods. The injection molding method has the advantages of fast production speed, high efficiency, automation of operation, a large variety of designs, a large variety of shapes including simple and complex shapes, and a large variety of sizes including large and small sizes. Moreover, dimension of product is precise, product is easy to be updated and module can be made into complex shapes. Injection molding is suitable for mass production and is applicable to the molding processing field of products with complex shape and the like.

In other embodiments, the method for preparing the oral retention device according to the first aspect of the present disclosure is injection molding, comprising the following steps:
(i) preparing a tooth matching component model according to a teeth model;
(ii) preparing a drug-loaded component model according to the size of the medicinal tablet;
(iii) obtaining an oral retention device model integrating the tooth matching component and the drug-loaded component;
(iv) preparing a personalized oral retention device by means of a traditional injection molding process, wherein
preferably, the teeth model is prepared by means of the traditional model-taking technology, or prepared by obtaining teeth data of a subject by means of the oral scanning technology and printing; and
more preferably, the materials of the tooth matching component model, the drug-loaded component model and the oral retention device model are dental wax, and/or the material of the teeth model is gypsum or resin.

For impression molding, firstly, a drug fastened module suitable for the extended release platform is prepared. Secondly, elliptical thermoplastic sheet is processed by conventional technology. Finally, a personalized REP was prepared. A thermoplastic sheet is heated in hot water at about 70° C. to soften it so as to have good plasticity. When the thermoplastic sheet becomes translucent (about 1 minute), take it out and put it on the teeth, and press the softened thermoplastic sheet to completely wrap the teeth to form a retention enabling module that completely fitted to the teeth. The drug fastened module is then quickly embedded into the uncured retention enabling module and cooled to solidify into a personalized retention enabling platform (REP). Some water can be sprayed briefly to further accelerate the cooling, wait for the personalized retention enabling platform to cool and restore the original opaque plate state, and take out the cooled personalized retention enabling platform from the oral cavity.

In other embodiments, the method for preparing the oral retention device according to the first aspect of the present disclosure is impression molding, comprising:
designing a drug-loaded component according to the size of the medicinal tablet; preparing the tooth matching component from polycaprolactone (PCL) as the material, and preparing the drug-loaded component from cobalt-chromium alloy as the material; and assembling the tooth matching component and the drug-loaded component into a complete oral retention device.

In a specific embodiment, at first, a drug-loaded component capable of loading an osmotic pump tablet is prepared by means of a traditional injection molding process; and then a thermoplastic sheet is heated and softened to prepare a tooth matching component, and at the same time the softened tooth matching component is fitted with the drug-loaded component in an embedded manner and is then cooled to form an integrated oral retention device, which is taken out of the oral cavity.

Preferably, the retention enabling platform is prepared from one or more oral stable materials including oral stable metals and thermoplastic elastomers.

More preferably, the oral stable metal comprises dental titanium, stainless steel, cobalt chromium alloy, cobalt chromium molybdenum alloy, nickel chromium alloy or precious metal, and the thermoplastic elastomer comprises polycaprolactone (PCL), ethylene vinyl acetate copolymer (EVA), high density polyethylene (HDPE), polypropylene (PP), polyacrylate, polyurethane, silicone polymer, polyester, poly (styrene-ethylene-butene-styrene)("SEBS"), poly (styrene-butadiene-styrene) ("SBS"), poly (styrene-isoprene-styrene) ("SIS"), or a copolymer of any two or more of the above, or a physical combination thereof.

Osmotic pump extended release drug delivery system is an advanced oral osmotic pump extended release drug delivery system, which can be in the form of tablets with an outer semi-permeable membrane and one or more small laser drilled orifices. When the tablet is taken orally through the gastrointestinal tract, water is absorbed by osmosis through the semi-permeable membrane, and the resulting osmotic pressure will push the active drug through the orifice of the tablet. The elementary osmotic pump (EOP) developed by Alza in 1974 is the first embodiment of the drug delivery system of the oral osmotic pump. It is composed of a drug-containing tablet core coated with a semi-permeable coating membrane, and an orifice drilled for drug release on the coating membrane, so that simplifies the osmotic pump preparation into the form of an ordinary coated tablet. Push-pull osmotic pump (PPOP) is suitable for soluble or poorly soluble drugs, which can be a bi-layer tablet with a semi-permeable membrane. The drug-containing layer comprises a drug chamber containing drugs and osmotic active substances, and an osmotic push layer comprising osmotic polymer. When the system contacts with the water, the osmotic push layer swells and pushes the drug in the drug chamber to release through the drug delivery orifice. The pharmaceutical composition or the upper gastrointestinal tract (UGI) extended release drug delivery system of the present invention comprises the forms such as a single-layer elementary osmotic pump, a bi-layer push-pull osmotic pump, and a bi-layer push-pull osmotic pump comprising an immediate-release drug overcoat, but differs from the osmotic pump in the prior art.

In the extended release dosage form of the present invention as described above, preferably, in the extended release platform, the drug-containing layer comprises active pharmaceutical ingredients and excipients, and the active pharmaceutical ingredient is one or more of levodopa, carbidopa, baclofen, acyclovir, valacyclovir, ganciclovir, metformin, and gabapentin.

Preferably, the active pharmaceutical ingredient comprises levodopa and/or carbidopa. The excipient is one or more of filler, osmotic agent, hydrophilic polymer, binding agent, lubricant, preservative, flavoring agent, acidifying agent and antioxidant. More preferably, the excipient is one or more of filler, osmotic agent, hydrophilic polymer, binding agent, lubricant and preservative. Even more preferably, the excipients are filler, osmotic agent, hydrophilic polymer, binding agent, lubricant and preservative.

In one embodiment, when the pharmaceutically active ingredient comprises levodopa, the weight percentage of the levodopa is 20-70%. In another embodiment, when the active ingredient comprises carbidopa, the weight percentage of carbidopa is 0-20% but not 0%, Wherein the weight percentage is the weight percentage of each component of the drug-containing layer.

In one embodiment, the pharmaceutically active ingredient comprises levodopa, and the weight percentage of the levodopa is 30-50%. In another embodiment, when the active ingredient comprises carbidopa, the weight percentage of the carbidopa is 1-10%, wherein the weight percentage is the weight percentage of each component of the drug-containing layer.

Preferably, in the pharmaceutical composition described above, when the excipient comprises a filler, the filler is one or more of microcrystalline cellulose, hydroxypropyl cellulose and mannitol; wherein the weight percentage of the filler is 0-50% but not 0%.

In another embodiment, when the excipient comprises an osmotic agent, the osmotic agent is one or more of magnesium sulfate, magnesium chloride, sodium chloride, lithium chloride, potassium sulfate, sodium sulfate, mannitol, urea, sorbitol, inositol, sucrose and glucose, wherein the weight percentage of the osmotic agent is 0-50% but not 0%.

In another embodiment, when the excipient comprises a hydrophilic polymer, the hydrophilic polymer is one or more of hydroxypropyl cellulose, hydroxypropyl methyl cellulose, carboxymethyl cellulose, polyvinylpyrrolidone and hydroxyethyl cellulose, wherein the weight percentage of the hydrophilic polymer is 0-50% but not 0%.

In another embodiment, when the excipient comprises an acidifying agent, the acidifying agent is one or more of citric acid, sodium citrate, potassium citrate, malic acid, fumaric acid, lactic acid, phosphoric acid and tartaric acid, wherein the weight percentage of the acidifying agent is 0-10% but not 0%.

The weight percentage is the weight percentage of each component of the drug-containing layer.

Preferably, the tablet core of the pharmaceutical composition further comprises an osmotic push layer, wherein the osmotic push layer comprises a hydrophilic polymer, an osmotic agent and a binding agent. Preferably, the osmotic push layer comprises a hydrophilic polymer, an osmotic agent, a binding agent, and a lubricant. More preferably, the osmotic push layer comprises a hydrophilic polymer, an osmotic agent, a binding agent, a lubricant and a colorant. The osmotic push layer and the drug-containing layer are components of a bi-layer tablet core, and the coating membrane is wrapped outside the tablet core. The pharmaceutical composition can be a kind of osmotic pump extended release drug delivery system, that is, a bi-layer push-pull osmotic pump.

As a pharmaceutical composition of the bi-layer push-pull osmotic pump, preferably, the hydrophilic polymer of the osmotic push layer is κ-carrageenan, sodium carboxymethyl cellulose or polyethylene oxide, wherein the molecular weight of the hydrophilic polymer is 75,000-7,500,000, and the weight percentage of the hydrophilic polymer is 25-85%.

In one embodiment, the osmotic agent in the osmotic pump push layer is one or more of magnesium sulfate, magnesium chloride, sodium chloride, lithium chloride, potassium sulfate, sodium sulfate, mannitol, urea, sorbitol, inositol, sucrose and glucose, wherein the weight percentage of the osmotic agent is 5-65%.

In another embodiment, the osmotic push layer comprises a binding agent, the binding agent is one or more of methyl cellulose, hydroxypropyl methyl cellulose, hydroxypropyl cellulose, sodium carboxymethyl cellulose, povidone and gelatin, wherein the weight percentage of the binding agent is 3-20%.

In another embodiment, the osmotic push layer comprises a lubricant, the lubricant is one or more of magnesium stearate, magnesium stearate fumarate, talc, and colloidal silica, wherein the weight percentage of the lubricant is 0-2% but not 0%.

In another embodiment, the osmotic push layer comprises a colorant, the colorant is one or more of iron oxide red, iron oxide yellow, and iron oxide black, wherein the weight percentage of the colorant is 0-5% but not 0%.

The weight percentage is the weight percentage of each component of the osmotic push layer.

Preferably, the osmotic push layer comprises sodium carboxymethyl cellulose, sorbitol, povidone, iron oxide red and magnesium stearate; or comprises sodium carboxymethyl cellulose, hydroxypropyl cellulose, sorbitol, iron oxide red, and magnesium stearate; preferably, is composed of sodium carboxymethyl cellulose, povidone K30, sorbitol, iron oxide red and magnesium stearate; or is composed of sodium carboxymethyl cellulose, hydroxypropyl cellulose, sorbitol, iron oxide red and magnesium stearate. More preferably, the sodium carboxymethyl cellulose is sodium carboxymethyl cellulose 7H4XF or 9H4XF.

More preferably, in one embodiment, the osmotic push layer comprises, in weight percentage, 25-85 wt % of sodium carboxymethyl cellulose, 5-65 wt % of sorbitol, 3-20 wt % of povidone, 0-5 wt % of iron oxide red and 0.5-2 wt % of magnesium stearate; or 25-85 wt % of sodium carboxymethyl cellulose, 5-65 wt % of sorbitol, 3-20 wt % of hydroxypropyl cellulose, 0-5 wt % of iron oxide red, and 0.5-2 wt % of magnesium stearate; wherein the weight percentage is the weight percentage of each component of the osmotic push layer.

Even more preferably, the osmotic push layer comprises 55 wt % of sodium carboxymethyl cellulose, 34.0-39.0 wt % of sorbitol, 3-20 wt % of povidone or 10 wt % of hydroxylpropyl cellulose, 0.5-5 wt % of iron oxide red and 0.5-2 wt % of magnesium stearate;

In another embodiment, the osmotic push layer comprises 55 wt % of sodium carboxymethyl cellulose, 39.0 wt % of sorbitol, 5.0 wt % of povidone and 0.5 wt % of iron oxide red and 0.5 wt % of magnesium stearate.

In another embodiment, the osmotic push layer comprises 55 wt % of sodium carboxymethyl cellulose, 34.0 wt % of sorbitol, 10.0 wt % of povidone K30, 0.5 wt % of iron oxide red and 0.5 wt % of magnesium stearate. The weight percentage is the weight percentage of each component of the osmotic push layer.

In another embodiment, the osmotic push layer comprises 55 wt % of sodium carboxymethyl cellulose, 34.0 wt % of sorbitol, 10.0 wt % of hydroxypropyl cellulose, 0.5 wt % of iron oxide red and 0.5 wt % of magnesium stearate. Wherein the weight percentage is the weight percentage of each component of the osmotic push layer.

In some preferred embodiments, the coating membrane of the pharmaceutical composition is further provided with a drug-containing immediate release overcoat. This constitutes a three-layer structure in which the inner layer is a tablet core, the middle layer is a coating membrane, and the outer layer is an overcoat.

More preferably, the drug-containing immediate release overcoat comprises an active pharmaceutical ingredient and an excipient, the active pharmaceutical ingredient comprises levodopa and/or carbidopa, and the excipient is one or more of hydroxypropyl cellulose, aspartame and the Mint Flavors.

In one embodiment, in the extended release platform, when the active pharmaceutical ingredient is levodopa, the weight percentage of the levodopa is 0-75% but not 0%, preferably 23.78-75%; and/or, when the active pharmaceutical ingredient is carbidopa, the weight percentage of carbidopa is 0-93% but not 0%, preferably 26.85-93%; and/or, when the excipient of the overcoat comprises hydroxypropyl cellulose, the weight percentage of the hydroxypropyl cellulose is 2-20%, preferably 10%; and/or, when the excipient of the overcoat comprises aspartame, the weight percentage of the aspartame is 0-5%, preferably 0.9-5%; and/or, when the excipient of the overcoat comprises Mint Flavor, the weight percentage of the Mint Flavor is 0-5%, preferably 0.1%; wherein the weight percentage is the weight percentage of each component of the overcoat.

More preferably, the weight of the coating membrane is not less than 2.0% of the weight of the tablet core; the coating membrane has one or more orifices, and the diameter of orifice is preferably 0.5 mm-1.0 mm, more preferably 0.5 mm, 0.75 mm and 1.0 mm. Preferably, the weight of the coating membrane is 2.0-15.0% of the weight of the tablet core. More preferably, the weight of the coating membrane is 4.0-8.0% of the weight of the tablet core.

Preferably, in one embodiment, the pharmaceutical composition is composed of a drug-containing layer and a coating membrane. In another embodiment, the pharmaceutical composition is composed of a drug-containing layer, an osmotic push layer and a coating membrane. In another embodiment, the pharmaceutical composition is composed of a drug-containing layer, an osmotic push layer, a coating membrane, and an overcoat.

Preferably, the drug-containing layer is composed of levodopa, carbidopa, microcrystalline cellulose, mannitol, citric acid, sodium hydroxypropyl methyl cellulose and magnesium stearate. In another embodiment, the drug-containing layer is composed of levodopa, microcrystalline cellulose, hydroxypropyl methyl cellulose and magnesium stearate. In another embodiment, the drug-containing layer is composed of levodopa, carbidopa, mannitol, citric acid and magnesium stearate. In another embodiment, the drug-containing layer is composed of levodopa, carbidopa, hydroxypropyl cellulose, mannitol, citric acid and magnesium stearate. In another embodiment, the drug-containing layer is composed of levodopa, carbidopa, hydroxypropyl cellulose, mannitol, citric acid, and povidone K30. In another embodiment, the drug-containing layer is composed of levodopa, hydroxypropyl cellulose, mannitol, povidone K30, magnesium stearate, Mint Flavor and aspartame. In another embodiment, the drug-containing layer is composed of levodopa, mannitol, povidone K30 and magnesium stearate. In another embodiment, the drug-containing layer is composed of levodopa, carbidopa, hydroxypropyl cellulose, mannitol, aspartame and magnesium stearate. In another embodiment, the drug-containing layer is composed of levodopa, hydroxypropyl cellulose, mannitol, povidone K30, magnesium stearate, Mint Flavor and aspartame. In another embodiment, the drug-containing layer is composed of levodopa, hydroxypropyl cellulose, mannitol, povidone K30, magnesium stearate, and aspartame. In another embodiment, the drug-containing layer is composed of levodopa, hydroxypropyl cellulose, mannitol, magnesium stearate, Mint Flavor and aspartame.

The osmotic push layer is composed of sodium carboxymethyl cellulose, povidone K30, sorbitol, iron oxide red and magnesium stearate, or the osmotic push layer is composed of sodium carboxymethyl cellulose, hydroxypropyl cellulose, sorbitol, iron oxide red and magnesium stearate. Preferably, the sodium carboxymethyl cellulose is sodium carboxymethyl cellulose 7H4XF or 9H4XF.

In one embodiment, the overcoat is composed of levodopa, carbidopa, hydroxypropyl cellulose, aspartame, and Mint Flavor; or the overcoat is composed of levodopa, carbidopa, hydroxypropyl cellulose and aspartame. In another embodiment, the overcoat is composed of carbidopa, hydroxypropyl cellulose and aspartame. In another embodiment, the overcoat is composed of levodopa, hydroxypropyl cellulose, and Mint Flavor. It is well known to those skilled in the art that the above "include" can be replaced by "consist of".

Preferably, the drug-containing layer is composed of levodopa, carbidopa, microcrystalline cellulose, mannitol, citric acid, sodium hydroxypropyl methyl cellulose and magnesium stearate, the weight percentage of levodopa is 40%, the weight percentage of carbidopa is 10.8%, the weight percentage of microcrystalline cellulose is 20%, the weight percentage of mannitol is 18.7%, the weight percentage of citric acid is 5%, the weight percentage of hydroxypropyl methyl cellulose sodium is 5%, and the weight percentage of magnesium stearate is 0.5%. The weight percentage is the weight percentage of each component of the drug-containing layer.

In another embodiment, the drug-containing layer is composed of levodopa, microcrystalline cellulose, hydroxypropyl methyl cellulose and magnesium stearate, and the weight percentage of the levodopa is 38%, the weight percentage of microcrystalline cellulose is 50%, the weight percentage of hydroxypropyl methyl cellulose is 10%, and the weight percentage of magnesium stearate is 2%, wherein the weight percentage is the weight percentage of each component of the drug-containing layer.

In another embodiment, the drug-containing layer is composed of levodopa, carbidopa, mannitol, citric acid and magnesium stearate. The weight percentage of the levodopa is 19.5%, and the weight percentage of carbidopa is 20%, the weight percentage of mannitol is 50%, the weight percentage of citric acid is 10%, and the weight percentage of magnesium stearate is 0.5%, wherein the weight percentage is the weight percentage of each component of the drug-containing layer.

In another embodiment, the drug-containing layer is composed of levodopa, carbidopa, hydroxypropyl cellulose, mannitol, citric acid and magnesium stearate, the weight percentage of the levodopa is 40%, the weight percentage of carbidopa is 10.8%, the weight percentage of hydroxypropyl cellulose is 31%, the weight percentage of mannitol is 12.7%, and the weight percentage of citric acid is 5%, and the weight percentage of the magnesium stearate is 0.5%, wherein the weight percentage is the weight percentage of each component of the drug-containing layer.

In another embodiment, the drug-containing layer is composed of levodopa, carbidopa, hydroxypropyl cellulose, mannitol, citric acid and povidone K30, the weight percentage of levodopa is 40%, the weight percentage of carbidopa is 10.8%, the weight percentage of hydroxypropyl cellulose is 31%, the weight percentage of mannitol is 12.7%, and the weight percentage of citric acid is 5%, and the weight percentage of povidone K30 is 0.5%, wherein the weight percentage is the weight percentage of each component of the drug-containing layer.

In another embodiment, the drug-containing layer is composed of levodopa, hydroxypropyl cellulose, mannitol, povidone K30, magnesium stearate, Mint Flavor and aspartame, the weight percentage of levodopa is 45%, the weight percentage of hydroxypropyl cellulose is 31%, the weight percentage of mannitol is 16%, the weight percentage of povidone K30 is 5%, the weight percentage of the magnesium stearate is 1%, the weight percentage of the Mint Flavor is 1%, and the weight percentage of the aspartame is 1%, wherein the weight percentage is the weight percentage of each component of the drug-containing layer.

In another embodiment, the drug-containing layer is composed of levodopa, mannitol, povidone K30, and magnesium stearate, the weight percentage of levodopa is 70%, the weight percentage of mannitol is 9%, the weight percentage of povidone K30 is 20%, and the weight percentage of magnesium stearate is 1%, wherein the weight percentage is the weight percentage of each component of the drug-containing layer.

In another embodiment, the drug-containing layer is composed of levodopa, carbidopa, hydroxypropyl cellulose, mannitol, aspartame and magnesium stearate, the weight percentage of levodopa is 20%, the weight percentage of carbidopa is 20%, the weight percentage of hydroxypropyl cellulose is 50%, the weight percentage of mannitol is 4%, and the weight percentage of aspartame is 5%, and the weight percentage of magnesium stearate is 1%, wherein the weight percentage is the weight percentage of each component of the drug-containing layer.

In another embodiment, the drug-containing layer is composed of levodopa, hydroxypropyl cellulose, mannitol, povidone K30, magnesium stearate, Mint Flavor and aspartame, the weight percentage of levodopa is 45%, the weight percentage of the hydroxypropyl cellulose is 31%, the weight percentage of the mannitol is 17%, the weight percentage of the povidone K30 is 5%, the weight percentage of magnesium stearate is 1% and the weight percentage of aspartame is 1%, wherein the weight percentage is the weight percentage of each component of the drug-containing layer.

In another embodiment, the drug-containing layer is composed of levodopa, hydroxypropyl cellulose, mannitol, magnesium stearate, Mint Flavor and aspartame. The weight percentage of the levodopa is 62.5%, the weight percentage of the hydroxypropyl cellulose is 31%, the weight percentage of the mannitol is 4.5%, the weight percentage of the Mint Flavor is 0.1%, the weight percentage of aspartame is 0.9% and the weight percentage of magnesium stearate is 1%, wherein the weight percentage is the weight percentage of each component of the drug-containing layer.

In another embodiment, the drug-containing layer is composed of levodopa, hydroxypropyl cellulose, mannitol, magnesium stearate, Mint Flavor and aspartame. The weight percentage of the levodopa is 46.9%, the weight percentage of the hydroxypropyl cellulose is 31%, the weight percentage of the mannitol is 20.1%, the weight percentage of the Mint Flavor is 0.1%, the weight percentage of aspartame is 0.9%, and the weight percentage of magnesium stearate is 1%, wherein the weight percentage is the weight percentage of each component of the drug-containing layer.

In another embodiment, the drug-containing layer is composed of levodopa, hydroxypropyl cellulose, mannitol, povidone K30, magnesium stearate and aspartame. The weight percentage of the levodopa is 45%, the weight percentage of the hydroxypropyl cellulose is 31%, the weight percentage of the mannitol is 17%, the weight percentage of the povidone K30 is 5%, the weight of the magnesium stearate is 1%, and the weight percentage of the aspartame is 1%, wherein the weight percentage is the weight percentage of each component of the drug-containing layer.

In another embodiment, the drug-containing layer is composed of levodopa, hydroxypropyl cellulose, mannitol, povidone K30, magnesium stearate, Mint Flavor and aspartame. The weight percentage of the levodopa is 45%, the weight percentage of the hydroxypropyl cellulose is 31%, the weight percentage of the mannitol is 12%, and the weight percentage of the povidone K30 is 5%, the weight percentage of the Mint Flavor is 5%, the weight percentage of aspartame is 1%, and the weight percentage of magnesium stearate is 1%, wherein the weight percentage is the weight percentage of each component of the drug-containing layer.

Or when the drug-containing layer is composed of levodopa, hydroxypropyl cellulose, mannitol, magnesium stearate, Mint Flavor and aspartame, the drug-containing layer is composed of 45 wt % of levodopa, 31 wt % of hydroxypropyl cellulose, 22 wt % of mannitol, 0.9 wt % of aspartame, 1.0 wt % of magnesium stearate and 0.1 wt % of Mint Flavor; wherein the weight percentage is the weight percentage of each component of the drug-containing layer.

More preferably, the coating membrane is composed of 50 wt % of cellulose acetate membrane and 50 wt % of copovidone VA64; the coating membrane is composed of 70 wt % of cellulose acetate membrane and 30 wt % of copovidone VA64; the coating membrane is composed of 60 wt % of cellulose acetate membrane and 40 wt % of copovidone VA64; wherein the weight percentage is the weight percentage of each component of the coating membrane.

More preferably, the weight of the coating membrane is 2.0%, 4.2%, 4.5%, 4.6%, 4.8%, 5.0%, 5.9%, 6.5%, 6.7%, 7.0%, 7.7%, 7.9% or 9.7% of the weight of the tablet core.

Preferably, when the osmotic push layer is composed of sodium carboxymethyl cellulose 7H4XF, povidone K30, sorbitol, iron oxide red and magnesium stearate, In one embodiment, the weight percentage of the carboxymethyl cellulose sodium 7H4XF is 55%, the weight percentage of the povidone K30 is 5%, the weight percentage of the sorbitol is 39%, the weight percentage of the iron oxide red is 0.5%, and the weight percentage of the magnesium stearate is 0.5%, wherein the weight percentage is the weight percentage of each component of the osmotic push layer.

In another embodiment, the weight percentage of the carboxymethyl cellulose sodium 7H4XF is 55%, the weight percentage of the povidone K30 is 10%, the weight percentage of the sorbitol is 34%, the weight percentage of the iron oxide red is 0.5%, and the weight percentage of the magnesium stearate is 0.5%, and the weight percentage is the weight percentage of each component of the osmotic push layer.

In another embodiment, the weight percentage of the sodium carboxymethyl cellulose is 85%, the weight percentage of the povidone K30 is 3%, the weight percentage of the sorbitol is 5%, the weight percentage of the iron oxide red is 5%, and the weight percentage of the magnesium stearate is 2%, wherein the weight percentage is the weight percentage of each component of the osmotic push layer.

In another embodiment, the weight percentage of the sodium carboxymethyl cellulose is 25%, the weight percentage of the povidone K30 is 9.5%, the weight percentage of the sorbitol is 65% and the weight percentage of the magnesium stearate is 0.5%, wherein the weight percentage is the weight percentage of each component of the osmotic push layer.

In another embodiment, the weight percentage of the carboxymethyl cellulose sodium 7H4XF is 60%, the weight percentage of the povidone K30 is 10%, the weight percentage of the sorbitol is 26%, the weight percentage of the iron oxide red is 2%, and the weight percentage of the magnesium stearate is 2%, wherein the weight percentage is the weight percentage of each component of the osmotic push layer.

In another embodiment, the weight percentage of the carboxymethyl cellulose sodium 7H4XF is 40%, the weight percentage of the povidone K30 is 20%, the weight percentage of the sorbitol is 36%, the weight percentage of the iron oxide red is 3.5%, and the weight percentage of the magnesium stearate is 0.5%, wherein the weight percentage is the weight percentage of each component of the osmotic push layer.

In another embodiment, the osmotic push layer is composed of sodium carboxymethyl cellulose 9H4XF, povidone K30, sorbitol, iron oxide red and magnesium stearate, the weight percentage of sodium carboxymethyl cellulose 9H4XF is 55%, the weight percentage of povidone K30 is 5%, the weight percentage of sorbitol is 39%, and the weight percentage of iron oxide red is 0.5% and the weight percentage of magnesium stearate is 0.5%, wherein the weight percentage is the weight percentage of each component of the osmotic push layer.

Or, in another embodiment, the osmotic push layer is composed of sodium carboxymethyl cellulose 7H4XF, hydroxypropyl cellulose, sorbitol, iron oxide red and magnesium stearate, the weight percentage of sodium carboxymethyl cellulose 7H4XF is 55%, the weight percentage of hydroxypropyl cellulose is 10%, the weight percentage of sorbitol is 34%, the weight percentage of the iron oxide red is 0.5% and the weight percentage of the magnesium stearate is 0.5%, wherein the weight percentage is the weight percentage of each component of the osmotic push layer.

More preferably, when the overcoat is composed of levodopa, carbidopa, hydroxypropyl cellulose, aspartame and Mint Flavor, the weight percentage of the levodopa is 23.78%, the weight percentage of the carbidopa is 64.22%, the weight percentage of the hydroxypropyl cellulose is 10%, and the weight percentage of the aspartame is 1%, and the weight percentage of the Mint Flavor is 1%, wherein the weight percentage is the weight percentage of each component of the overcoat.

In another embodiment, the overcoat is composed of carbidopa, hydroxypropyl cellulose and aspartame, the weight percentage of carbidopa is 93%, the weight percentage of hydroxypropyl cellulose is 2% and the weight percentage of aspartame is 5%, wherein the weight percentage is the weight percentage of each component of the overcoat.

In another embodiment, the overcoat is composed of levodopa, hydroxypropyl cellulose and Mint Flavor, the weight percentage of the levodopa is 75%, the weight percentage of the hydroxypropyl cellulose is 20%, and the weight percentage of the Mint Flavor is 5%, wherein the weight percentage is the weight percentage of each component of the overcoat.

In another embodiment, when the overcoat is composed of levodopa, carbidopa, hydroxypropyl cellulose, aspartame and Mint Flavor, the weight percentage of the levodopa is 62.15%, the weight percentage of the carbidopa is 26.85%, the weight percentage of the hydroxypropyl cellulose is 10%, and the weight percentage of the aspartame is 0.9%, and the weight percentage of the Mint Flavor is 0.1%, wherein the weight percentage is the weight percentage of each component of the overcoat.

When the overcoat is composed of levodopa, carbidopa, hydroxypropyl cellulose and aspartame, the weight percentage of levodopa is 24%, the weight percentage of carbidopa is 65%, the weight percentage of hydroxypropyl cellulose is 10% and the weight percentage of aspartame is 1%, wherein the weight percentage is the weight percentage of each component of the overcoat.

When the overcoat is composed of levodopa, carbidopa, hydroxypropyl cellulose, aspartame and Mint Flavor, the weight percentage of the levodopa is 54%, the weight percentage of the carbidopa is 35%, the weight percentage of the hydroxypropyl cellulose is 10%, the weight percentage of the aspartame is 0.9%, and the weight percentage of the Mint Flavor is 0.1%; or, the weight percentage of the levodopa is 42.8%, the weight percentage of the carbidopa is 46.2%, the weight percentage of the hydroxypropyl cellulose is 10%, the weight percentage of the aspartame is 0.9%, the weight percentage of the Mint Flavor is 0.1%, or the weight percentage of the levodopa is 28.2%, and the weight percentage of the carbidopa is 60.8%, the weight percentage of the hydroxypropyl cellulose is 10%, the weight percentage of the aspartame is 0.9%, and the weight percentage of the Mint Flavor is 0.1%, wherein the weight percentage is the weight percentage of each component of the overcoat.

More preferably, the weight gain of the overcoat relative to the tablet core is 12.9% or 13.2% or 15.7% or 21.0% of weight percentage.

Preferably, the pharmaceutical composition is composed of a drug-containing layer and a coating membrane, the drug containing layer is composed of 40 wt % of levodopa, 10.8 wt % of carbidopa, 20 wt % of microcrystalline cellulose, 18.7 wt % of mannitol, 5 wt % of citric acid, 5 wt % of hydroxypropyl methyl cellulose sodium and 0.5 wt % of magnesium stearate, and the weight percentage is the weight percentage of each component of the drug-containing layer. The coating membrane is composed of 50% wt % of cellulose acetate membrane and 50 wt % of copovidone VA64, and the weight percentage is the weight percentage of each component of the coating membrane. The weight of the coating membrane is 2.0% of the weight of the tablet core. A dosage form containing the pharmaceutical composition has a 0.5 mm exit orifice mechanically drilled on the drug-containing layer side of the coated tablet, and levodopa and carbidopa are delivered at an average rate of 14.17 mg/hr and 4.59 mg/hr, with 85% of the drug delivered in 12 and 10 hours, respectively. The dosage form can be maintained in the oral cavity until the osmotic layer reaches the delivery orifice, or maintained in the oral cavity for 8-9 hours and then swallowed.

The pharmaceutical composition is composed of a drug-containing layer and a coating membrane, the drug-containing layer is composed of 38 wt % of levodopa, 50 wt % of microcrystalline cellulose, 10 wt % of hydroxypropyl methyl cellulose and 2 wt % of magnesium stearate, wherein the weight percentage is the weight percentage of each component of the drug-containing layer. The coating membrane is composed of 50 wt % of cellulose acetate membrane and 50 wt % of copovidone VA64, wherein the weight percentage is the weight percentage of each component of the coating membrane, and the weight of the coating membrane is 4.5% of the weight of tablet core. The dosage form with a membrane weight gain of 4.5% delivered levodopa at an average rate of 9.4 mg/hr, with 85% of levodopa delivered in 9.0 hours.

Or, the pharmaceutical composition is composed of a drug-containing layer and a coating membrane, the drug-containing layer comprises 19.5 wt % of levodopa, 20 wt % of carbidopa, 50 wt % of mannitol, 10 wt % of citric acid and 0.5 wt % of magnesium stearate, wherein the weight percentage is the weight percentage of each component of the drug-containing layer. The coating membrane is composed of 50 wt % of cellulose acetate membrane and 50 wt % of copovidone VA64, wherein the weight percentage is the weight percentage of each component of the coating membrane, and the weight of the coating membrane is 4.5% of the weight of tablet core. The dosage form with a membrane weight gain of 4.5% delivered levodopa at an average rate of 22.9 mg/hr, with 85% of levodopa delivered in 13.0 hours.

Preferably, in one embodiment, the pharmaceutical composition is composed of a drug-containing layer, an osmotic push layer, and a coating membrane, and the drug-containing layer is composed of 40 wt % of levodopa, 10.8 wt % of carbidopa, 31 wt % of hydroxypropyl cellulose, 12.7 wt % of mannitol, 5 wt % of citric acid and 0.5 wt % of magnesium stearate, wherein the weight percentage is the weight percentage of each component of the drug-containing layer. The osmotic push layer is composed of 55 wt % of sodium carboxymethyl cellulose 7H4XF or 9H4XF, 5 wt % of povidone K30, 39 wt % of sorbitol, 0.5 wt % of iron oxide red and 0.5 wt % of magnesium stearate, wherein the weight percentage is the weight percentage of each component of the osmotic push layer. The coating membrane is composed of 70 wt % of cellulose acetate membrane and 30 wt % of copovidone VA64, wherein the weight percentage is the weight percentage of each component of the coating membrane. The weight of the coating membrane is 2.0%, 4.0% or 5.0% of the weight of the tablet core. When the sodium carboxymethyl cellulose is 7H4XF, one side of the drug-containing layer contains an exit orifice of 0.5 mm, the dosage form with a tablet core weight gain of 5.0% delivered levodopa and carbidopa at an average rate of 17.0 mg/hr and 4.6 mg/hr, with 85% of levodopa and carbidopa delivered in 10.0 hours. The dosage form can be maintained in the oral cavity until the osmotic layer reaches the delivery orifice, or maintained in the oral cavity for 6-7 hours and then swallow. The sizes of delivery orifice vary from 0.5 mm, 0.75 mm and 1.0 mm. The dosage form with a tablet core weight gain of 4.0% delivered levodopa and carbidopa at an average rate of 21.3 mg/hr and 5.7 mg/hr, with 85% of levodopa and carbidopa delivered in 10.0 hours. The dosage form can be maintained in the oral cavity until the osmotic layer reaches the delivery orifice, or maintained in the oral cavity for 4-5 hours and then swallow. When the sodium carboxymethyl cellulose is 9H4XF, the dosage form with a coating membrane weight gain of 2.0% delivered levodopa and carbidopa at an average rate of 24.3 mg/hr and 6.6 mg/hr, with 85% levodopa and carbidopa delivered in 7.0 hours. The dosage form can be maintained in the oral cavity until the osmotic layer reaches the delivery port, or maintained in the oral cavity for 3-4 hours and then swallowed.

In another embodiment, the pharmaceutical composition is composed of a drug-containing layer, an osmotic push layer, and a coating membrane, the drug-containing layer is composed of 40 wt % of levodopa, 10.8 wt % of carbidopa, 31 wt % of hydroxypropyl cellulose, 12.7 wt % of mannitol, 5 wt % of citric acid and 0.5 wt % of povidone K30, wherein the weight percentage is the weight percentage of each component of the drug-containing layer. The osmotic push layer is composed of 55 wt % of sodium carboxymethyl cellulose 7H4XF, 5 wt % of povidone K30, 39 wt % of sorbitol, 0.5 wt % of iron oxide red, and 0.5 wt % of magnesium stearate, wherein the weight percentage is the weight percentage of each component of the osmotic push layer; the coating membrane is composed of 60 wt % of cellulose acetate membrane and 40% copovidone VA64, wherein the weight percentage is the weight percentage of each component of the coating membrane; and the weight of the coating membrane is 5.0% of the weight of the tablet core. The dosage form containing the pharmaceutical composition delivered 85% of the drug in 6 hours. The dosage form can be maintained in the oral cavity until the osmotic layer reaches the delivery port, or maintained in the oral cavity for 2-3 hours, and then swallowed.

In another embodiment, the pharmaceutical composition is composed of a drug-containing layer, an osmotic push layer, and a coating membrane, the drug-containing layer is composed of 45 wt % of levodopa, 31 wt % of hydroxypropyl cellulose, 16 wt % of mannitol, 5 wt % of povidone K30, and 1 wt % of magnesium stearate, 1 wt % of Mint Flavor and 1 wt % of aspartame, wherein the weight percentage is the weight percentage of each component of the drug-containing layer; the osmotic push layer is composed of 55 wt % of sodium carboxymethyl cellulose 7H4XF, 10 wt % of povidone K30, 34 wt % of sorbitol, 0.5 wt % of iron oxide red and 0.5 wt % of magnesium stearate, wherein the weight percentage is the weight percentage of each component of the osmotic push layer; the coating membrane is composed of 60 wt % of cellulose acetate membrane and 40 wt % of copovidone VA64, wherein the weight percentage is the weight percentage of each component of the coating membrane; and the weight of the coating membrane is 4.2%, 6.7% or 9.7% of the weight of the tablet core. The dosage form containing the pharmaceutical composition with a membrane weight gain of 4.2%, 6.7% and 9.7% delivered levodopa at an average rate of 38.3 mg/hr, 27.3 mg/hr, and 21.3 mg/hr, with 85% of levodopa delivered in 5.0 hours, 7.0 hours and 9.0 hours, respectively.

In another embodiment, the pharmaceutical composition is composed of a drug-containing layer, an osmotic push layer, and a coating membrane, the drug-containing layer is composed of 45 wt % of levodopa, 31 wt % of hydroxypropyl cellulose, 16 wt % of mannitol, 5 wt % of povidone K30, 1 wt % of magnesium stearate, 1 wt % of Mint Flavor and 1 wt % of aspartame, wherein the weight percentage is the weight percentage of each component of the drug-containing layer; the osmotic push layer is composed of 55 wt % of sodium carboxymethyl cellulose 7H4XF, 10 wt % of povidone K30, 34 wt % of sorbitol, 0.5 wt % of iron oxide red and 0.5 wt % of magnesium stearate, wherein the weight percentage is the weight percentage of each component of the osmotic push layer; the coating membrane is composed of 70 wt % of cellulose acetate membrane and 30 wt % of copovidone VA64, wherein the weight percentage is the weight percentage of each component of the coating membrane; and the weight of the coating membrane is 4.6% or 7.9% of the weight of the tablet core. The dosage form containing the pharmaceutical composition with a membrane weight gain of 4.6% and 7.9% delivered levodopa at an average rate of 25.5 mg/hr and 16.9 mg/hr, with 85% of levodopa delivered in 7.5 hours and 11.5 hours, respectively.

In another embodiment, the pharmaceutical composition is composed of a drug-containing layer, an osmotic push layer, and a coating membrane, the drug-containing layer is composed of 70 wt % of levodopa, 9 wt % of mannitol, 20 wt % of povidone K30, and 1 wt % of magnesium stearate, wherein the weight percentage is the weight percentage of each component of the drug-containing layer; the osmotic push layer is composed of 85 wt % of sodium carboxymethyl cellulose, 3 wt % of povidone K30, 5 wt % of sorbitol, 5 wt % of iron oxide red and 2 wt % of magnesium stearate, wherein the weight percentage is the weight percentage of each component of the osmotic push layer; the coating membrane is composed of 70 wt % of cellulose acetate membrane and 30 wt % of copovidone VA64, wherein the weight percentage is the weight percentage of each component of the coating membrane; and the weight of the coating membrane is 4.5% of the weight of the tablet core. The dosage form containing the pharmaceutical composition delivered levodopa at an average rate of 35.0 mg/hr, with 85% of levodopa delivered in 8.5 hours.

In another embodiment, the pharmaceutical composition is composed of a drug-containing layer, an osmotic push layer, and a coating membrane, the drug-containing layer is composed of 20 wt % of levodopa, 20 wt % of carbidopa, 50 wt % of hydroxypropyl cellulose, 4 wt % of mannitol, 5 wt % of aspartame and 1 wt % of magnesium stearate, wherein the weight percentage is the weight percentage of each component of the drug-containing layer; the osmotic push layer is composed of 25 wt % of sodium carboxymethyl cellulose, 9.5 wt % of povidone K30, 65 wt % of sorbitol and 0.5 wt % of magnesium stearate, wherein the weight percentage is the weight percentage of each component of the osmotic push layer; the coating membrane is composed of 90 wt % of cellulose acetate membrane and 10 wt % of copovidone VA64, wherein the weight percentage is the weight percentage of each component of the coating membrane; and the weight of the coating membrane is 4.5% of the weight of the tablet core. The dosage form containing the pharmaceutical composition delivered levodopa and carbidopa at an average rate of 7.1 mg/hr, with 85% of levodopa and carbidopa delivered in 12 hours.

Preferably, in one embodiment, the pharmaceutical composition is composed of a drug-containing layer, an osmotic push layer, a coating membrane and an overcoat, the drug-containing layer is composed of 45 wt % of levodopa, 31 wt % of hydroxypropyl cellulose, 16 wt % of mannitol, 5 wt % of povidone K30, 1 wt % of magnesium stearate, 1 wt % of Mint Flavor and 1 wt % of aspartame, wherein the weight percentage is the weight percentage of each component of the drug-containing layer; the osmotic push layer is composed of 55 wt % of sodium carboxymethyl cellulose 7H4XF, 10 wt % of povidone K30, 34 wt % of sorbitol, 0.5 wt % of iron oxide red and 0.5 wt % of magnesium stearate, wherein the weight percentage is the weight percentage of each component of the osmotic push layer; the coating membrane is composed of 70 wt % of cellulose acetate membrane and 30 wt % of copovidone VA64, wherein the weight percentage is the weight percentage of each component of the coating membrane; and the weight of the coating membrane is 4.8% or 7.7% of the weight of the tablet core, the overcoat is composed of 23.78 wt % of levodopa, 64.22 wt % of carbidopa, 10 wt % of hydroxypropyl cellulose, 1 wt % of aspartame and 1 wt % of Mint Flavor immediate release composition, wherein the weight percentage is the weight percentage of each component of the overcoat, and the weight gain of the overcoat relative to the tablet core is 13.2% and 12.9% by weight, respectively. The release profile of the dosage form containing the pharmaceutical composition showed a rapid release of levodopa/carbidopa, the dosage form with 4.8% and 7.7% weight gain in coating membrane followed by sustained release with a release duration of approximately 8.5 hours and 12.0 hours, respectively. The dosage form with a 4.8% membrane weight gain can be maintained in the oral cavity for 4-5 hours and then maintained in the oral cavity for the duration of the meal or throughout the release period. Dosage forms with a 7.7% membrane weight gain can be maintained in the oral cavity for 8-9 hours before swallowing, or be maintained in the oral cavity for the entire release period.

In another embodiment, the pharmaceutical composition is composed of a drug-containing layer, an osmotic push layer, a coating membrane and an overcoat, the drug-containing layer is composed of 45 wt % of levodopa, 31 wt % of hydroxypropyl cellulose, 17 wt % of mannitol, 5 wt % of povidone K30, 1 wt % of magnesium stearate and 1 wt % of aspartame, wherein the weight percentage is the weight percentage of each component of the drug-containing layer; the osmotic push layer is composed of 60 wt % of sodium carboxymethyl cellulose 7H4XF, 10 wt % of povidone K30, 26 wt % of sorbitol, 2 wt % of iron oxide red and 2 wt % of magnesium stearate, wherein the weight percentage is the weight percentage of each component of the osmotic push layer; the coating membrane is composed of 70 wt % of cellulose acetate membrane and 30 wt % of copovidone VA64, wherein the weight percentage is the weight percentage of each component of the coating membrane; and the weight of the coating membrane is 4.8% of the weight of the tablet core, the overcoat is composed of 93 wt % of CD, 2 wt % of hydroxypropyl cellulose and 5 wt % of aspartame immediate release composition, wherein the weight percentage is the weight percentage of each component of the overcoat, and the weight increase of the overcoat relative to the tablet core is 13.2 wt % of. The immediate release overcoat of the dosage form is rapidly released first, followed by sustained releasing for approximately 8 hours. The dosage form can be maintained in the oral cavity for 4-5 hours and then swallow before eating or be maintained in the oral cavity for the entire release period.

In another embodiment, the pharmaceutical composition is composed of a drug-containing layer, an osmotic push layer, a coating membrane and an overcoat, the drug-containing layer is composed of 45 wt % of levodopa, 31 wt % of hydroxypropyl cellulose, 12 wt % of mannitol, 5 wt % of povidone K30, 5 wt % of Mint Flavor, 1 wt % of aspartame and 1 wt % of magnesium stearate, wherein the weight percentage is the weight percentage of each component of the drug-containing layer; the osmotic push layer is composed of 40 wt % of sodium carboxymethyl cellulose 7H4XF, 20 wt % of povidone K30, 36 wt % of sorbitol, 3.5 wt % of iron oxide red and 0.5 wt % of magnesium stearate, wherein the weight percentage is the weight percentage of each component of the osmotic push layer; the coating membrane is composed of 70 wt % of cellulose acetate membrane and 30 wt % of copovidone VA64, wherein the weight percentage is the weight percentage of each component of the coating membrane; and the weight of the coating membrane is 4.8% of the weight of the tablet core, the overcoat is composed of 75 wt % of levodopa, 20 wt % of hydroxypropyl cellulose and 5 wt % of Mint Flavor immediate release composition, wherein the weight percentage is the weight percentage of each component of the overcoat, and the weight gain of the overcoat relative to the tablet core is 13.2 wt %. The immediate release overcoat of the dosage form is rapidly released first, followed by sustained releasing for approximately 8 hours. The dosage form can be maintained in the oral cavity for 4-5 hours and then swallow before eating or be maintained in the oral cavity for the entire period of releasing.

In another embodiment, the pharmaceutical composition is composed of a drug-containing layer, an osmotic push layer, a coating membrane and an overcoat, the drug-containing layer is composed of 62.5 wt % of levodopa, 31 wt % of hydroxypropyl cellulose, 4.5 wt % of mannitol, 0.1 wt % of Mint Flavor, 0.9 wt % of aspartame and 1 wt % of magnesium stearate, wherein the weight percentage is the weight percentage of each component of the drug-containing layer; the osmotic push layer is composed of 55 wt % of sodium carboxymethyl cellulose 7H4XF, 10 wt % of hydroxypropyl cellulose, 34 wt % of sorbitol, 0.5 wt % of iron oxide red and 0.5 wt % of magnesium stearate, wherein the weight percentage is the weight percentage of each component of the osmotic push layer; the coating membrane is composed of 70 wt % of cellulose acetate membrane and 30 wt % of copovidone VA64, wherein the weight percentage is the weight percentage of each component of the coating membrane; and the weight of the coating membrane is 6.5% of the weight of the tablet core, the overcoat is composed of 62.15 wt % of levodopa, 26.85 wt % of carbidopa, 10 wt % of hydroxypropyl cellulose, 0.9 wt % of aspartame and 0.1 wt % of Mint Flavor immediate release composition, wherein the weight percentage is the weight percentage of each component of the overcoat, and the weight gain of the overcoat relative to the tablet core is 21.0 wt %.

In another embodiment, the pharmaceutical composition is composed of a drug-containing layer, an osmotic push layer, a coating membrane and an overcoat, the drug-containing layer is composed of 46.9 wt % of levodopa, 31 wt % of hydroxypropyl cellulose, 20.1 wt % of mannitol, 0.1 wt % of Mint Flavor, 0.9 wt % of aspartame and 1 wt % of magnesium stearate, wherein the weight percentage is the weight percentage of each component of the drug-containing layer; the osmotic push layer is composed of 55 wt % of sodium carboxymethyl cellulose 7H4XF, 10 wt % of hydroxypropyl cellulose, 34 wt % of sorbitol, 0.5 wt % of iron oxide red and 0.5 wt % of magnesium stearate, wherein the weight percentage is the weight percentage of each component of the osmotic push layer; the coating membrane is composed of 70 wt % of cellulose acetate membrane and 30 wt % of copovidone VA64, wherein the weight percentage is the weight percentage of each component of the coating membrane; and the weight of the coating membrane is 6.5% of the weight of the tablet core, the overcoat is composed of 62.15 wt % of levodopa, 26.85 wt % of carbidopa, 10 wt % of hydroxypropyl cellulose, 0.9 wt % of aspartame and 0.1 wt % of Mint Flavor immediate release composition, wherein the weight percentage is the weight percentage of each component of the overcoat, and the weight increase of the overcoat relative to the tablet core is 15.7 wt %.

In a specific preferred embodiment, the pharmaceutical composition is composed of a drug-containing layer, an osmotic push layer, a coating membrane and an overcoat; wherein the drug-containing layer is composed of 45 wt % of levodopa, 31 wt % of hydroxypropyl cellulose, 16 wt % of mannitol, 5 wt % of povidone K30, 1 wt % of magnesium stearate, 1 wt % of Mint Flavor and 1 wt % of aspartame, wherein the weight percentage is the weight percentage of each component of the drug-containing layer; the osmotic push layer is composed of 55 wt % of sodium carboxymethyl cellulose 7H4XF, 10 wt % of hydroxypropyl cellulose, 34 wt % of sorbitol, 0.5 wt % of iron oxide red and 0.5 wt % of magnesium stearate, wherein the weight percentage is the weight percentage of each component of the osmotic push layer; the coating membrane is composed of 70 wt % of cellulose acetate membrane and 30 wt % of copovidone VA64, wherein the weight percentage is the weight percentage of each component of the coating membrane; wherein, the cellulose acetate is a cellulose acetate membrane containing 39.8 wt % of acetyl, and the weight of the coating membrane is 5.9% of the weight of the tablet core; and, the overcoat is composed of 64.22 wt % of levodopa, 23.78 wt % of carbidopa, 10 wt % of hydroxypropyl cellulose, 1 wt % of aspartame and 1 wt % of Mint Flavor, wherein the weight percentage is the weight percentage of each component of the overcoat, the weight of the overcoat is 13.1% of the total weight of the tablet core and the coating membrane. When the solvent for the coating suspension of the overcoat is anhydrous ethanol, the content of carbidopa-related genotoxic impurity hydrazine in the obtained dosage form is 1.7 ppm, the content of carbidopa-related impurity dihydroxyphenyl-acetone (DHPA) is 0.21%. When the solvent for the coating suspension of the overcoat is purified water, the concentration of the solid content of the overcoat is 10.0 wt %, including 24.0% wt % of levodopa, 65.0 wt % of carbidopa monohydrate, 10.0 wt % of hydroxylpropyl cellulose and 1.0 wt % of aspartame in weight percentage; the content of carbidopa-related genotoxic impurity hydrazine in the obtained dosage form is 3.8 ppm, and the content of carbidopa-related impurity DHPA is 0.28%. When the coating solution solvent of the overcoat is anhydrous ethanol, the carbidopa-related genotoxic impurity hydrazine and impurity DHPA of the obtained dosage form are significantly lower than the coating solution solvent of the overcoat is purified water. The immediate release overcoat of the dosage form is rapidly released first, followed by a sustained release with a duration of approximately 8 hours. The osmotic delivery system can be maintained in the oral cavity for 3-5 hours and then swallow before eating or be maintained in the oral cavity for the entire release period.

In a specific preferred embodiment, the pharmaceutical composition is composed of a drug-containing layer, an osmotic push layer, a coating membrane and an overcoat; the drug-containing layer is composed of 45 wt % of levodopa, 31 wt % of hydroxypropyl cellulose, 22 wt % of mannitol, 0.9 wt % of aspartame, 0.5 wt % of magnesium stearate and 0.1 wt % of Mint Flavor, wherein the weight percentage is the weight percentage of each component of the drug-containing layer; the osmotic push layer is composed of 55 wt % of sodium carboxymethyl cellulose 7H4XF, 10 wt % of hydroxypropyl cellulose, 34 wt % of sorbitol, 0.5 wt % of iron oxide red and 0.5 wt % of magnesium stearate, wherein the weight percentage is the weight percentage of each component of the osmotic push layer; the coating membrane is composed of 70 wt % of cellulose acetate membrane and 30 wt % of copovidone VA64, wherein the weight percentage is the weight percentage of each component of the coating membrane; wherein, the cellulose acetate is a cellulose acetate membrane containing 39.8 wt % of acetyl, and the weight of the coating membrane is 6.5% of the weight of the tablet core; and, the overcoat is composed of 54 wt % of levodopa, 35 wt % of carbidopa, 10 wt % of hydroxypropyl cellulose, 0.9 wt % of aspartame and 0.1 wt % of Mint Flavor, wherein the weight percentage is the weight percentage of each component of the overcoat, the weight of the overcoat is 13.1% of the total weight of the tablet core and the coating membrane. The final dosage form is composed of an immediate release overcoat of 62.5 mg levodopa and 37.5 mg carbidopa, and 187.5 mg levodopa was contained in an extended release drug-containing layer. The immediate release overcoat of the dosage form is rapidly released first, followed by a sustained release with a duration of approximately 8 hours. The osmotic delivery system can be maintained in the oral cavity for 4-5 hours and then swallow before eating or be maintained in the oral cavity for the entire release period.

In a specific preferred embodiment, the pharmaceutical composition is composed of a drug-containing layer, an osmotic push layer, a coating membrane and an overcoat; the drug-containing layer is composed of 45 wt % of levodopa, 31 wt % of hydroxypropyl cellulose, 22 wt % of mannitol, 0.9 wt % of aspartame, 1 wt % of magnesium stearate and 0.1 wt % of Mint Flavor, wherein the weight percentage is the weight percentage of each component of the drug-containing layer; the osmotic push layer is composed of 55 wt % of sodium carboxymethyl cellulose 7H4XF, 10 wt % of hydroxypropyl cellulose, 34 wt % of sorbitol, 0.5 wt % of iron oxide red and 0.5 wt % of magnesium stearate, wherein the weight percentage is the weight percentage of each component of the osmotic push layer; the coating membrane is composed of 70 wt % of cellulose acetate membrane and 30 wt % of copovidone VA64, wherein the weight percentage is the weight percentage of each component of the coating membrane; wherein, the cellulose acetate is a cellulose acetate membrane containing 39.8 wt % of acetyl, and the weight of the coating membrane is 7.0% of the weight of the tablet core; and, the overcoat is composed of 42.8 wt % of levodopa, 46.2 wt % of carbidopa, 10 wt % of hydroxypropyl cellulose, 0.9 wt % of aspartame and 0.1 wt % of Mint Flavor, wherein the weight percentage is the weight percentage of each component of the overcoat, the weight of the overcoat is 13.1% of the total weight of the tablet core and the coating membrane. The final dosage form is composed of an immediate release overcoat of 37.5 mg levodopa and 37.5 mg carbidopa, and 112.5 mg levodopa was contained in an extended release drug-containing layer. The immediate release overcoat of the dosage form is rapidly released first, followed by a sustained release with a duration of approximately 8 hours. The osmotic delivery system can be maintained in the oral cavity for 4-5 hours and then swallow before eating or be maintained in the oral cavity for the entire release period.

In a specific preferred embodiment, the pharmaceutical composition is composed of a drug-containing layer, an osmotic push layer, a coating membrane and an overcoat; the drug-containing layer is composed of 45 wt % of levodopa, 31 wt % of hydroxypropyl cellulose, 22 wt % of mannitol, 0.9 wt % of aspartame, 1 wt % of magnesium stearate and 0.1 wt % of Mint Flavor, wherein the weight percentage is the weight percentage of each component of the drug-containing layer; the osmotic push layer is composed of 55 wt % of sodium carboxymethyl cellulose 7H4XF, 10 wt % of hydroxypropyl cellulose, 34 wt % of sorbitol, 0.5 wt % of iron oxide red and 0.5 wt % of magnesium stearate, wherein the weight percentage is the weight percentage of each component of the osmotic push layer; the coating membrane is composed of 70 wt % of cellulose acetate membrane and 30 wt % of copovidone VA64, wherein the weight percentage is the weight percentage of each component of the coating membrane; wherein, the cellulose acetate is a cellulose acetate membrane containing 39.8 wt % of acetyl, and the weight of the coating membrane is 9.0% of the weight of the tablet core; and, the overcoat is composed of 28.2 wt % of levodopa, 60.8 wt % of carbidopa, 10 wt % of hydroxypropyl cellulose, 0.9 wt % of aspartame and 0.1 wt % of Mint Flavor, wherein the weight percentage is the weight percentage of each component of the overcoat, the weight of the overcoat is 13.1% of the total weight of the tablet core and the coating membrane. The final dosage form is composed of an immediate release overcoat of 18.75 mg levodopa and 37.5 mg carbidopa, and 56.25 mg levodopa was contained in an extended release drug-containing layer. The immediate release overcoat of the dosage form is rapidly released first, followed by a sustained release with a duration of approximately 8 hours. The osmotic delivery system can be maintained in the oral cavity for 4-5 hours and then swallow before eating or be maintained in the oral cavity for the entire release period.

Wherein, the preparation method of the overcoat contains: dissolving each component of the above-mentioned weight percent of the overcoat in anhydrous ethanol to prepare a coating suspension. Preferably, the ratio of the components of the overcoat to the anhydrous ethanol is 1:10. In the pharmaceutical composition, carbidopa is only present in an immediate release overcoat, and the core portion of the extended release tablet does not contain carbidopa. The dosage form has the following advantages: the content of carbidopa related genotoxic impurity hydrazine and impurity dihydroxyphenylacetone (DHPA) is lower. When the solvent for the coating suspension of the overcoat is anhydrous ethanol, the carbidopa related genotoxic impurity hydrazine and impurity DHPA of the obtained dosage form are significantly lower than that of the obtained dosage form when the solvent for the coating suspension is pure water.

Unless otherwise specified, the method for preparing the aforementioned pharmaceutical composition is a conventional preparation method in the art.

Preferably, as described above, the pharmaceutical composition is an osmotic pump extended release drug delivery system. Preferably, the osmotic pump extended release drug delivery system is an extended release tablet. More preferably, the extended release tablet is a cylinder with a diameter of 5-10 mm and a height of 5-30 mm, or a caplet with a length of 10-25 mm and a width of 5-10 mm. Most preferably, each of the extended release tablets contains 62.5 mg CD and 500 mg LD, or 62.5 mg CD and 375 mg LD, or 62.5 mg carbidopa and 250 mg levodopa, or 50 mg carbidopa and 500 mg levodopa, or 37.5 mg carbidopa and 375 mg levodopa.

To solve the above technical problems, one of the technical solutions of the present invention is: a method for using the above extended release dosage form, that is, placing the extended release platform in the personalized retention enabling platform, and fastening the retention enabling platform on the corresponding teeth in the oral cavity; taking out the extended release dosage form after keeping for 4-24 hours, replacing the extended release platform with a new one and fastening the retention enabling platform on the corresponding teeth in the oral cavity again, so that the drug can be released continuously and stably.

Without violating the common knowledge in the art, the preferred parameters described above may be optionally combined to obtain the preferred embodiments in the present invention.

The reagents and raw materials employed in the present invention are commercially available.

The advantageous effects achieved by the present invention are as follows: The invention provides an extended release system of an active pharmaceutical ingredient (API) capable of improving absorption window and a preparation method thereof, so as to provide non-invasive extended release products having a stable plasma profiles of active pharmaceutical ingredient such as LD, or LD and CD for the treatment of patients with PD, especially those with advanced PD.

The present invention also provides an oral retention device, with a medicinal tablet being inserted in a direction from the throat to the incisors such that, because the back side of the oral retention device is close to the throat, and due to blocking by the oral mucosal tissues, the medicinal tablet will not easily drop out in the oral cavity. The medicinal tablet is inserted into the oral retention device to form a drug-device composition, which is fixed on the matching tooth in the oral cavity, implementing sustained release of the drug within a certain period of time. After being retained for 0-24 hours, the drug-device composition is taken out, replaced with a new medicinal tablet, and re-fixed on the matching tooth in the oral cavity, so as to continuously and stably release the drug.

BRIEF DESCRIPTION OF THE DRAWINGS

FIG. 3C is a flow chart of manufacturing the extended release dosage form (ERP+REP) of the present invention: wherein the extended release platform is an extended release dosage form of a bi-layer push-pull system with an immediate-release drug overcoat.

FIGS. 4A-4F show the preparation of the retention enabling platform (REP) described in embodiment 1: FIG. 4A. Drug fastened module; FIG. 4B. Drug fastened module; FIG. 4C. Drug fastened module; FIG. 4D. Drug fastened module; FIG. 4E. Thermoplastic tablet; FIG. 4F. Personalized retention enabling platform (REP).

FIG. 5A. Drug fastened module; FIG. 5B. Extended release platform fastened in the drug fastened module.

FIG. 6A. Retention enabling platform (REP); FIG. 6B. Extended release platform fastened in the Retention enabling platform (REP); FIG. 6C. Retention enabling platform (REP) with self-locking cover; FIG. 6D. Extended release platform fastened in the retention enabling platform (REP); FIG. 6E. Extended release platform with the cover closed+retention enabling platform (REP); FIG. 6F. Retention enabling platform with reversible cover (REP); FIG. 6G. Extended release platform fastened in the retention enabling platform (REP); FIG. 6H. Extended release platform with the cover closed+retention enabling platform (REP); FIG. 6I. Retention enabling platform (REP) with a cover that can slide up and down; FIG. 6J. Extended release platform fastened to the retention enabling platform (REP); FIG. 6K. Extended release platform with cover closed+Retention enabling platform (REP);

FIG. 7A.

Retention enabling platform (REP); FIG. 7B. Extended release platform fastened in the retention enabling platform (REP);

LIST OF REFERENCE NUMERALS

Figure 1A:
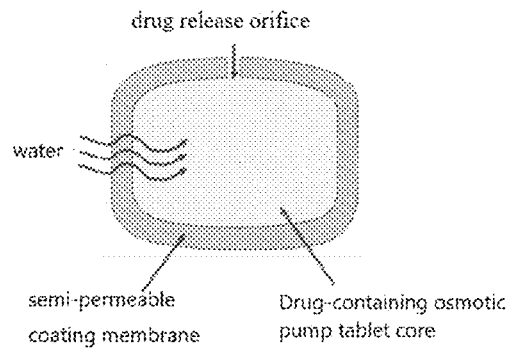
FIG. 1A is a schematic diagram of an extended release platform (ERP), wherein the ERP is a single-layer elementary osmotic pump (EOP).

11: Tooth matching component of back-insertion oral retention device
21: Retainer of back-insertion oral retention device
31: Ring body of back-insertion oral retention device
311: Opening on ring body of back-insertion oral retention device
41: Drug-loaded component of back-insertion oral retention device
12: Tooth matching component of front-insertion oral retention device
22: Retainer of front-insertion oral retention device
32: Ring body of front-insertion oral retention device
321: Opening on ring body of front-insertion oral retention device
42: Drug-loaded component of front-insertion oral retention device

DETAILED DESCRIPTION OF THE PREFERRED EMBODIMENT

The preferred embodiments will be listed below, and the present disclosure will be illustrated more clearly and completely in conjunction with the drawings. It should be noted that unless otherwise specified, the relative arrangement and numerical values of the parts and steps set forth in these embodiments do not limit the scope of the present disclosure. The following embodiments further illustrate the present invention, but the present invention is not limited thereto. The experimental methods without specific conditions specified in the following embodiments were selected according to conventional methods and conditions, or according to product specifications. Active pharmaceutical ingredients (APIs) for the present invention include, but are not limited to, levodopa/carbidopa, baclofen, acyclovir, valaciclovir, ganciclovir, metformin and gabapentin.

In one embodiment, the active pharmaceutical ingredient (API) is levodopa/carbidopa, which is incorporated in a single-layer elementary osmotic pump (EOP) known in the art (U.S. Pat. Nos. 3,845,770 and 3,916,899). As shown in FIG. 1A, EOP comprises an API tablet core and a rate control membrane encompassing the tablet core. The EOP comprises at least one orifice drilling through the membrane so that LD/CD can be released into the oral cavity through the orifice. The tablet core comprises LD/CD, osmotic agent, microcrystalline cellulose (MCC), binding agent, lubricant, flavoring agent (optional), acidifying agent (optional) and antioxidant (optional). The rate control membrane comprises a complete or at least a part of a semipermeable polymer that can penetrate water or moisture present in the oral cavity, while substantially impermeable to drugs and other optional components that can be present in the core. The representative semipermeable polymer is cellulose acetate with 32.0-39.8% acetyl content. Flow enhancers can be incorporated into rate control membranes. The flow enhancers in the invention includes but are not limited to polyethylene glycol, povidone, copovidone and other water-soluble polymers. The preferred flow enhancers are soluble in water and organic solvents such as acetone, methanol, ethanol and isopropanol copovidone (VA64). Typical solvent systems for high-throughput membrane compositions used in the prior art include acetone and water, while acetone is used to dissolve cellulose acetate and water is used to dissolve the enhancer. Their evaporation rates are significantly different, especially at low temperatures, which often lead to unknown incompatibility, i.e. potential precipitation of cellulose acetate during the coating process. Therefore, the solvent in the prior art often produces a high-throughput membrane with mechanical defects, thus weakening the mechanical strength of the membrane. A more homogenous membrane can be easily formed by using copovidone dissolved in acetone or acetone/ethanol mixed solvent, thus having a more consistent release profile compare with other membranes.

Figure 1B:
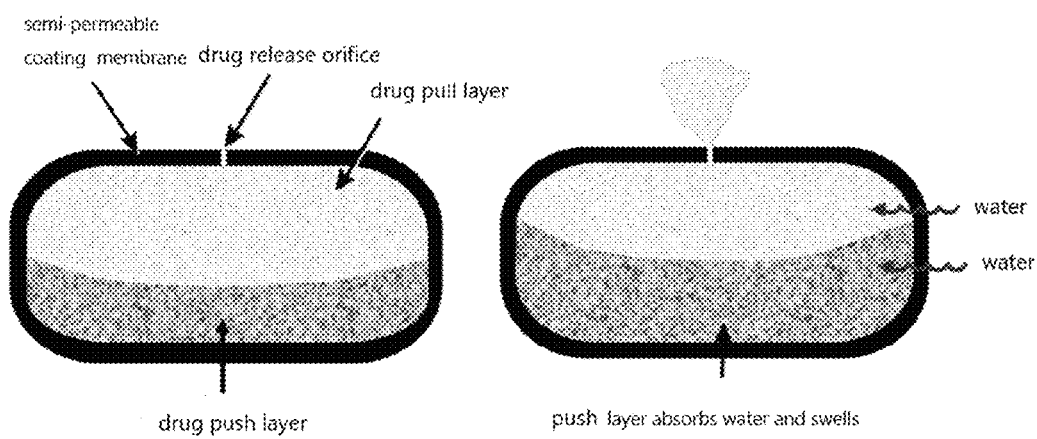
FIG. 1B is a schematic diagram of an ERP, wherein the ERP is a bi-layer osmotic push-pull system.

In another embodiment, LD/CD is incorporated into a bi-layer (push-pull) osmotic delivery system known in the prior art (U.S. Pat. Nos. 4,327,725 and 4,612,008). As shown in FIG. 1B, the push-pull system is composed of two layers of core (including drug-containing pull layer and osmotic push layer) and a rate control membrane encompassing the core. The push-pull system comprises at least one orifice through the membrane on the side containing the drug-containing layer, so that the contents of the pull layer can be released into the oral cavity through the orifice. The pull layer comprises LD/CD, a hydrophilic polymer, an osmotic agent, a binding agent, a lubricant, a flavoring agent (optional), an acidifying agent (optional), and an antioxidant (optional). The push layer comprises a high molecular weight hydrophilic polymer, an osmotic agent, a binding agent, a lubricant, and a colorant (optional). The push-pull osmotic delivery system operates by absorbing water or moisture through a rate control membrane into a bi-layer core, wherein it hydrates the two layers, thereby expanding the osmotic push layer and push the hydrated, dispensable drug-containing layer formulation through orifice from the system.

Due to the presence of the hydrophilic polymer, the push layer composition can retain a large amount of water in the layer. The hydrophilic polymer can be κ-carrageenan, sodium carboxymethyl cellulose, polyethylene oxide with a molecular weight of 75,000 to 7,500,000.

The osmotic agent used for the purpose of the present invention is selected from magnesium sulfate, magnesium chloride, sodium chloride, lithium chloride, potassium sulfate, sodium sulfate, mannitol, urea, sorbitol, inositol, sucrose, glucose, etc. Mannitol and sorbitol are the preferred osmotic agents due to the release of drug-containing layer formulation in the oral cavity and thus attracting attention to their taste and cariogenicity.

Figure 2:
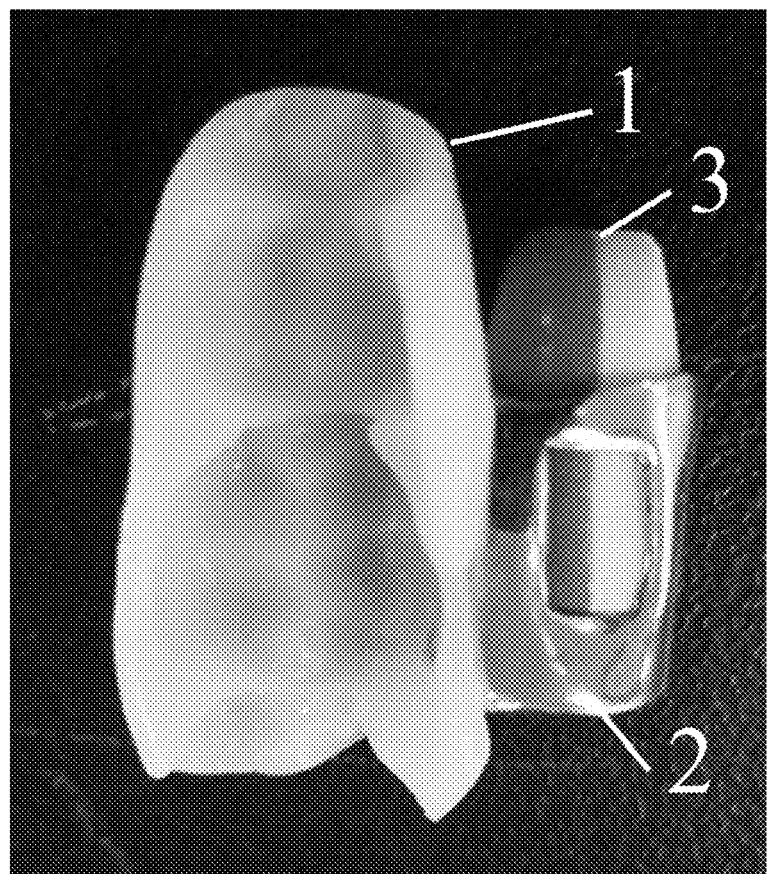
FIG. 2 is the schematic diagram of extended release dosage form (combination of extended release platform ERP and retention enabling platform REP): 1. Personalized retention enabling modules of retention enabling platform (REP); 2. Extended release platform (ERP); 3. Drug fastened modules of retention enabling platform (REP).

FIG. 2 is a schematic diagram of an extend release dosage form (a combination of an extended release platform ERP and a retention enabling platform REP). The retention enabling platform comprises a personalized retention enabling module and a drug fastened module. The retention enabling module can be personalized to match the corresponding teeth. The drug fastened module serves as a reservoir to fasten the extended release platform ERP for maintaining the ERP in a right place. The retention enabling platform REP personalized retention enabling module can match the second molar and anterior and posterior teeth. Due to the length of the retention enabling platform REP, it (the REP that maintains the ERP) is in a non-inhalable position, thus eliminating the possibility of blocking. The preferred structure of the REP is a buckle-type or nut-type basket with various mesh sizes so that the ERP does not fall out. Other structures of the REP can be, but are not limited to, a holder with two clamping arms.

Figure 3A:
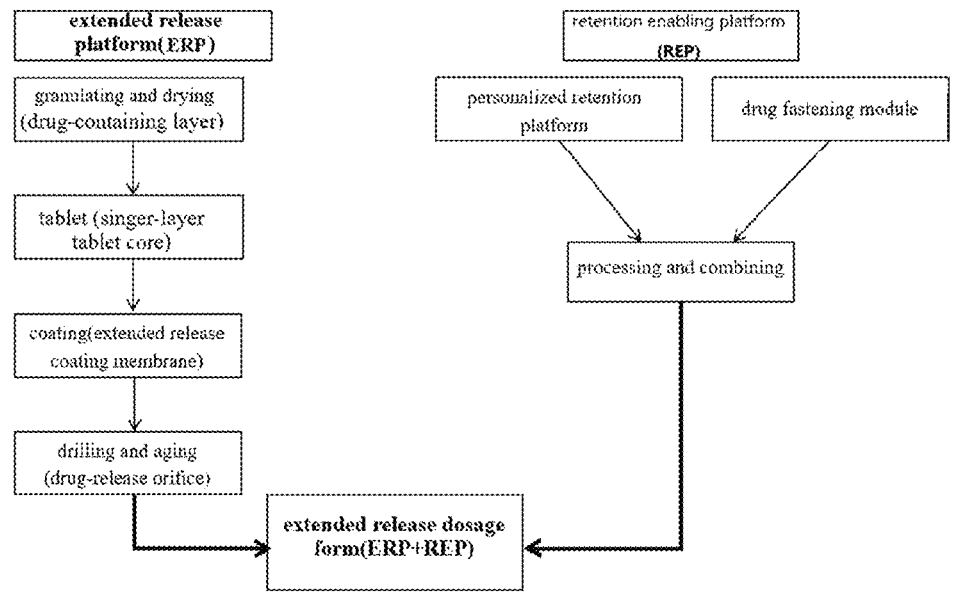
FIG. 3A is a flow chart of manufacturing the extended release dosage form (ERP+REP) of the present invention: wherein the extended release platform is an extended release dosage form of a single-layer elementary osmotic pump (EOP).
Figure 3B:
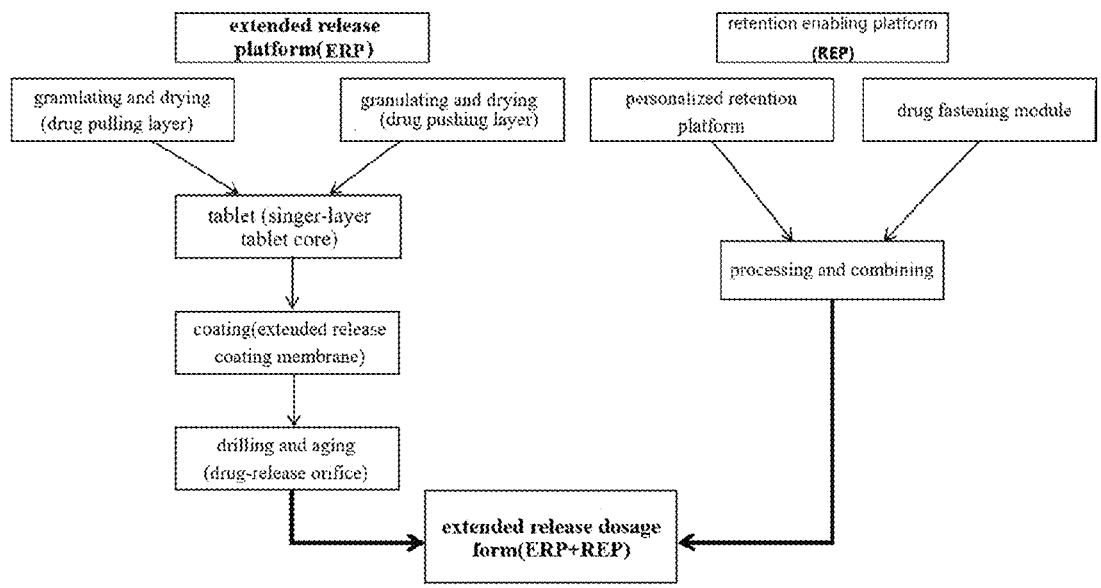
FIG. 3B is a flow chart of manufacturing the extended release dosage form (ERP+REP) of the present invention: wherein the extended release platform is an extended release dosage form of a bi-layer osmotic push-pull system.

FIG. 3A, FIG. 3B and FIG. 3C are flow charts of manufacturing the extended release dosage form (ERP+REP) of the present invention. FIG. 3A shows an extended release dosage form for manufacturing an extended release platform as a single-layer elementary osmotic pump (EOP); FIG. 3B shows an extended release dosage form for manufacturing an extended release platform as a bi-layer push-pull osmotic system; FIG. 3C shows an extended release dosage form for manufacturing an extended release platform as a bi-layer push-pull system with an immediate release drug overcoat.

The retention enabling module REP can be made of polymer materials or dental titanium using 3D printing technology, injection molding processes or impression molding. Polymer materials include, but are not limited to, polycaprolactone (PCL), ethylene-vinyl acetate copolymer (EVA), high density polyethylene (HDPE), polypropylene (PP), polyacrylate and any other tissue compatible polymers. PCL is a good material because of its low melting point and good biocompatibility. Therefore, the personalized retention enabling module of REP made by PCL is easily softened in hot water, and then matches the molar or premolar.

One of the ERP in the invention is a single-layer elementary osmotic pump, and can be manufactured by standard manufacturing techniques. First of all, in the conventional wet granulation method, a high-shear granulator or a fluidized bed granulator can be used to prepare tablet core particle. In the second step, the granules are pressed into a single-layer tablet core in the press. Next, the tablet core is coated with a semi-permeable membrane coating composition. Finally, an orifice was drilled through the coating membrane.

Another ERP in the present invention is a bi-layer push-pull osmotic pump, and can be manufactured as follows. First of all, a high-shear granulator or fluidized bed granulator can be used to prepare granules of drug-containing layer and osmotic push layer. Secondly, the granules of these two layers are pressed into a bi-layer tablet core in a press. Next, the bi-layer tablet core is coated with a semi-permeable membrane coating composition, followed by a drying process. Finally, an orifice was drilled through the membrane of drug-containing layer.

Semi-permeable membranes of osmotic dosage forms can be formed by air suspension technology. The method comprises suspending and tumbling a single-layer tablet core or a bi-layer tablet core in an air flow and coating composition until the membrane is homogenously formed around the core. The air suspension process can be realized by the fluidized bed granulator with a Wurster plug-in. Acetone or acetone ethanol mixed solubilizer can be used as coating solvent, in which 2.0-5 wt % of the membrane-forming composition is dissolved. Other membrane forming techniques, such as pan coating, can also be used. In the pan coating system, the membrane is continuously sprayed onto the tablet core of the rotary pan and deposited into a membrane composition. Generally, the membrane formed by these techniques with a thickness of 25-250 µm, preferably 100-150 µm.

Optionally, a single-layer EOP or bi-layer push-pull system with drilled orifice can be coated with an immediate release LD/CD drug-containing layer.

The personalized retention enabling platform (REP) in the present invention can be manufactured as follows. REP was prepared by 3D printing technology. First, an oral image of an individual was obtained by an oral scanner. Next, the CAD/CAM software was used to design the REP, which was the holder of the ERP. Then, according to CAD/CAM design, 3D printing technology or injection molding process was used to make REP from histocompatible polymer or dental titanium, or cobalt chromium alloy, or cobalt chromium molybdenum alloy.

The personalized retention enabling platform (REP) in the present invention can also be manufactured by injection molding technology. First, the dental impression material was used to make a mold to prepare the same plaster tooth model as the patient; secondly, REP shape of dental wax was prepared on plaster dental model by conventional process; then, the embedded powder and water mixture were used to wrap the dental wax REP, and the embedded dental wax was heated to melt after standing and curing to obtain a REP-shaped injection mold cavity; finally, at a certain temperature, the completely molten cobalt-chromium alloy was poured into the mold cavity, cooled and cured, and then polished.

The personalized retention enabling platform (REP) in the present invention can also be manufactured by impression molding technology. Firstly, a drug fastened module was manufactured, and then, an oval thermoplastic sheet was processed by a conventional process. Then, the thermoplastic sheet was heated to soften it, and the softened thermoplastic sheet was pressed to completely cover the teeth to form a personalized retention enabling module that is completely fitted to the teeth. The drug fastened module was then quickly embedded on the uncured retention enabling module and cooled and solidify to form a personalized retention enabling platform (REP). Wait for the personalized retention enabling platform to cool and restore the original opaque hard membrane state, and remove the cooled personalized retention enabling platform from the oral cavity.

Embodiment 1 Preparation of Retention Enabling Platform (Impression Molding)

1. Drug fastened modules suitable as shown in FIG. 4A, FIG. 4B, FIG. 4C, and FIG. 4D, which is suitable for the extended release platform, were prepared. The drug fastened modules is made of stainless steel, dental titanium, cobalt chromium alloy, or cobalt chromium molybdenum alloy, and the shape of which can be one or more reservoirs with one or both ends open. The shape of the cross section of the reservoir can be polygon, circular closed-loop or open-loop with the opening smaller than the minimum diameter of the tablet.

2. 50 g polycaprolactone was processed into an oval thermoplastic sheet with a size of 2.5 cm×1.5 cm by conventional process (as shown in FIG. 4E);

3. Preparation of personalized REP: a piece of thermoplastic sheet was heated in hot water at about 70° C. to soften it with good moldability. When the thermoplastic sheet becomes translucent (about 1 minute), it was taken out and placed on the teeth, and the softened thermoplastic sheet was pressed to completely wrap the teeth to form a retention enabling module that completely matches the teeth. Then, the stainless-steel drug fastened module was quickly embedded on the uncured retention enabling module, and cooled and cured to form a personalized retention enabling platform (REP). Some water can be briefly sprayed to further accelerate the cooling, then wait for the personalized retention enabling platform to cool and restore the original opaque hard sheet state, and the cooled personalized retention enabling platform was taken out the from the oral cavity (as shown in FIG. 4F). The following FIG. 5A-5B can be used to explain its association and difference with FIG. 4A-4F.

Figures 5A, 5B:
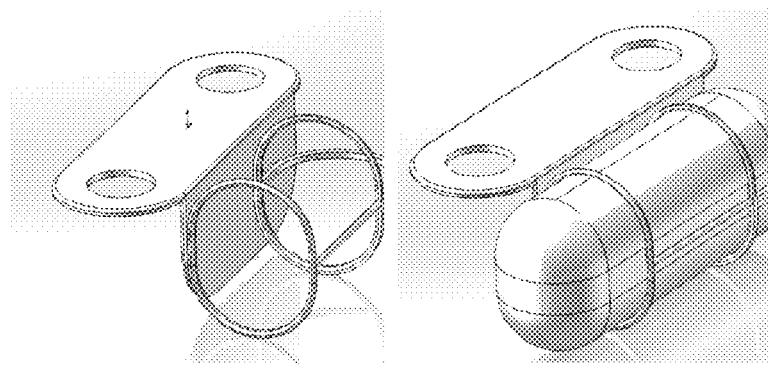
FIGS. 5A-5B show a drug fastened module described in embodiment 1.
Figure 6A:
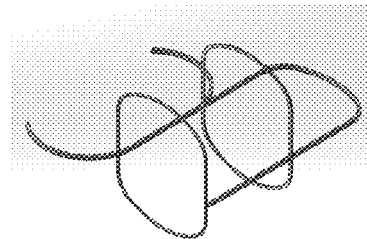
FIGS. 6A-6K show the retention enabling platform (REP) described in embodiment 2 and embodiment 3.
Figure 6B:
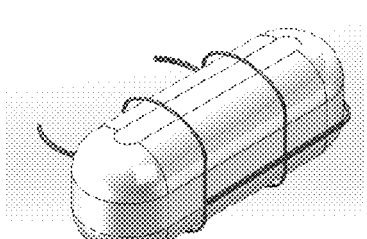
Figure 6C:
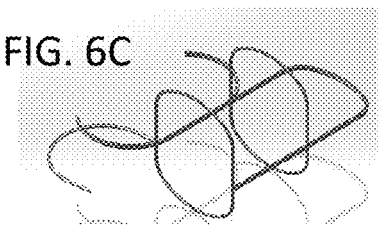
Figure 6D:
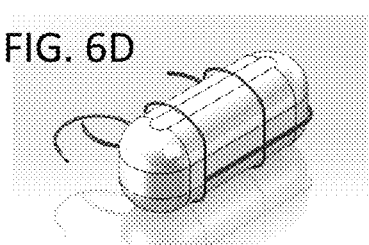
Figure 6E:
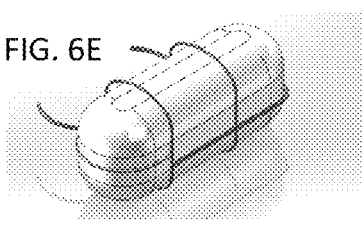
Figure 6F:
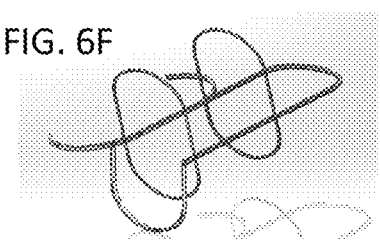
Figure 6G:
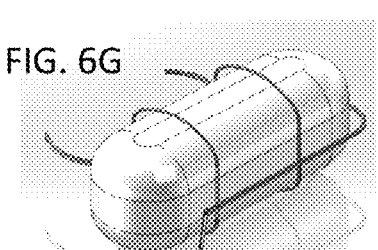
Figure 6H:
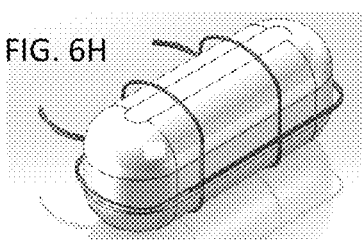
Figure 6I:
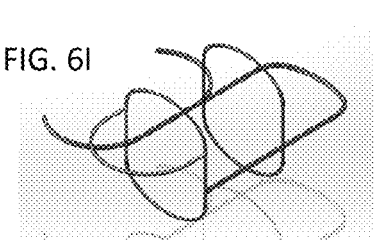
Figure 6J:
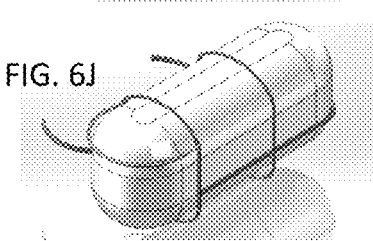
Figure 6K:
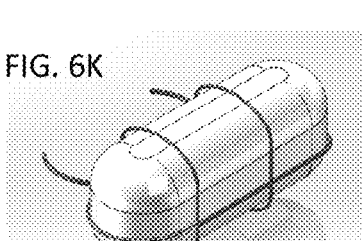

FIG. 5A-5B are the aforementioned drug fastened module: FIG. 5A. The drug fastened module; FIG. 5B. The extended release platform was fastened in the drug fastened module.

Embodiment 2 Preparation of Retention Enabling Platform (Injection Molding)

According to the following procedures, a retention enabling platform that fitted to the mandibular molar teeth was prepared by an injection molding process, as shown in FIG. 6.

First, a plaster dental model with the same dental properties as a patient was prepared by using a dental impression material to form a mold;

REP shape of dental wax was prepared on a plaster dental model by conventional process using dental wax;

The above dental wax REP was then wrapped with a mixture of embedding powder and water, and after standing and curing, the embedded dental wax was melted to obtain an injection mold cavity in the shape of REP;

At a certain temperature, the completely melted cobalt chromium alloy was poured into the mold cavity, cooled and cured, and then polished.

Embodiment 3 Preparation of Retention Enabling Platform (3D Printing)

According to the following procedures, a retention enabling platform that fitted to the mandibular molar teeth was prepared by oral scanning and 3D printing processes, as shown in FIG. 6.

Firstly, an individual oral image was obtained by the oral scanner;

CAD/CAM software or dental software was used to process scanning data, generate electronic tooth model, transform the date into editable file, and design a personalized retention enabling platform device that completely fitted to the teeth;

Cobalt chromium molybdenum 3D printing material was used to print the designed personalized device by 3D printer laser sintering technology.

Embodiment 4 Preparation of Retention Enabling Platform (Injection Molding)

Figure 7A:
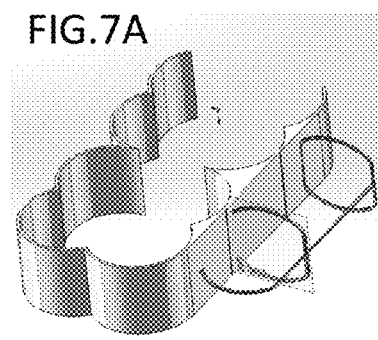
FIGS. 7A-7B show a retention enabling platform (REP) described in embodiment 4 and embodiment 5.
Figure 7B:
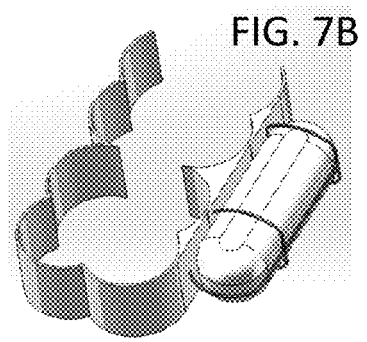

According to the following procedures, the retention enabling platform that fitted to the periphery of the non-occlusal surface of the mandibular molar was prepared by injection molding process, as shown in FIG. 7.

First, a plaster teeth model with the same dental properties as a patient is prepared by using a dental impression material to form a mold;

REP shape of dental wax was prepared on a plaster dental model by conventional process using dental wax;

The above dental wax REP was then wrapped with a mixture of embedding powder and water, and after standing and curing, the embedded dental wax was melted to obtain an injection mold cavity in the shape of REP;

At a certain temperature, the completely melted cobalt-chromium alloy is poured into the mold cavity, cooled and cured, and then polished.

Embodiment 5 Preparation of Retention Enabling Platform (3D Printing)

According to the following procedures, a retention enabling platform that fitted to the periphery of the non-occlusal surface of the mandibular molar was prepared by oral scanning and 3D printing processes, as shown in FIG. 7.

Firstly, an individual oral image was obtained by the oral scanner;

CAD/CAM software or dental software was used to process scanning data, generate electronic tooth model, transform the data into editable file, and design a personalized retention enabling platform device that completely fits to the teeth;

Cobalt chromium molybdenum 3D printing material was used to print the designed personalized device by 3D printer laser sintering technology.

Embodiment 6 Preparation of Extended Release Platform

A dosage form for distributing the beneficial drugs levodopa and carbidopa to oral cavity was manufactured as follows: first, a tablet core was prepared, comprising, in weight percentage, 40.0 $W_t$% of levodopa (LD), 10.8$W_t$% of carbidopa monohydrate (CD), 20.0$W_t$% of microcrystalline cellulose, 18.7$W_t$% of mannitol, 5.0$W_t$% of hydroxypropyl methylcellulose (HPMC E5) and 5.0$W_t$% of citric acid that were each passed through a 40-mesh stainless steel sieve, then blended and granulated with pure water until homogeneous wet mass was formed; the wet mass was passed through a 20-mesh stainless steel sieve and dried at 80° C. for 2 hours; the dried granules were passed through an 18-mesh stainless steel sieve and then mixed with 0.5$W_t$% of magnesium stearate.

Then, 500 mg of the drug core granules were compressed into a single-layer tablet core with a 9.0 mm round punch using a tablet press.

Figure 8:
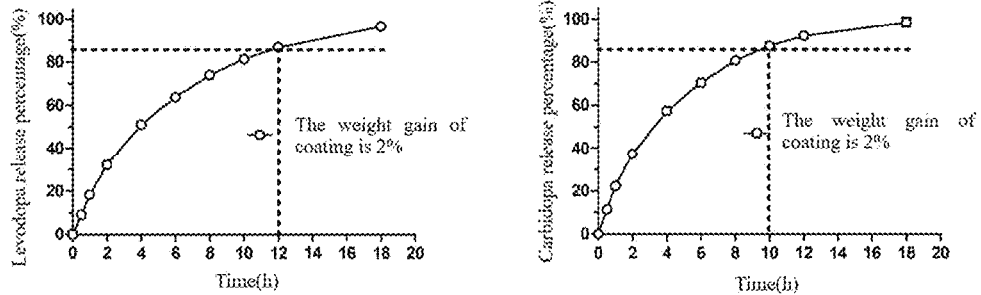
FIG. 8 is a release profile of the extended release platform (ERP) described in embodiment 6, and error bars indicate a standard deviation of n=3.

Next, the single-layer tablet core was coated with a semi-permeable membrane. The membrane-forming composition comprised, in weight percentage, 50$W_t$% of cellulose acetate and 50$W_t$% of Copovidone VA64. The membrane-forming composition was mixed with acetone to make a 4% of solid suspension. Using the process parameters listed in the table below, the membrane-forming composition was sprayed onto the tablet cores in a Glatt GC 1 pan coater to form a coating membrane. The membrane weight gain of the coated tablet was 2.0%. Finally, a 0.5 mm exit orifice was drilled mechanically on the drug layer side of the coated tablet. Residual solvents were removed by drying the dosage form at 40° C. and ambient humidity for 24 hours. The release profile of the final manufactured dosage form was measured in 0.1N HCl aqueous solution using USP I pulp board. As shown in FIG. 8, the final manufactured ERP dosage form delivered LD and CD at an average rate of 14.17 mg/hr and 4.59 mg/hr, with 85% of the drugs delivered in 12 and 10 hours, respectively. The ERP osmotic delivery system can be kept in oral cavity until the push-layer reaches the delivery orifice, or kept there for 8-9 hours, and then swallowed; or it can be fasten on the corresponding teeth in the oral cavity after being combined with the retention enabling platform REP and kept there for 12 hours.

| parameters of coating process | |
| --- | --- |
| Inlet temperature (° C.) | 20-40 |
| Exhaust temperature (° C.) | 14-25 |
| Air flow rate (m³/h) | 20-40 |
| Fluid delivery rate (g/min) | 5-25 |
| Atomizing air pressure (bar) | 0.6-0.8 |
| Pattern air pressure (bar) | 0.6-0.8 |
| Rotating speed (rpm) | 6-15 |
| Batch size (g) | 400 |

Embodiment 7 Preparation of Extended Release Platform

A dosage form designed, shaped and adapted for dispensing the beneficial drugs levodopa and carbidopa monohydrate to oral cavity was manufactured as follows: first, a drug layer composition was prepared, comprising, in weight percentage, 40.0$W_t$% of LD, 10.8$W_t$% of CD, 31.0$W_t$% of hydroxypropyl cellulose having an average molecular weight of 80,000, 12.7$W_t$% of mannitol and 5.0$W_t$% of citric acid, these excipients were each pass through a 40-mesh stainless steel sieve, then blended and granulated with 95% ethanol until homogeneous wet mass was formed; the wet mass was passed through a 20-mesh stainless steel sieve and dried at 80° C. for 2 hours; the dried granules were passed through an 18-mesh stainless steel sieve and then mixed with 0.5$W_t$% of magnesium stearate.

Next, a second composition, the osmotic layer, was prepared, comprising 55.0$W_t$% of sodium carboxymethyl cellulose 7H4XF, 39.0$W_t$% of sorbitol, 5.0$W_t$% of Povidone K30 and 0.5$W_t$% of iron oxide red; these components were each passed through a 40-mesh stainless steel sieve, then blended and granulated with 95% ethanol until homogeneous wet mass was formed; the wet mass was passed through a 20-mesh stainless steel sieve and dried at 80° C. for 2 hours; dried granules were passed through a 18-mesh stainless steel sieve and then mixed with 0.5 wt % of magnesium stearate.

Next, the drug-containing layer and the osmotic layer granules were pressed into a bi-layer tablet core. First, 500 mg of drug layer granules were added to a 9 mm round punch of a tablet press and tamped, then 250 mg of osmotic layer granules were added to the punch, and the granules of both layers were pressed with a tablet press into a contacting bi-layer tablet core.

Figure 9:
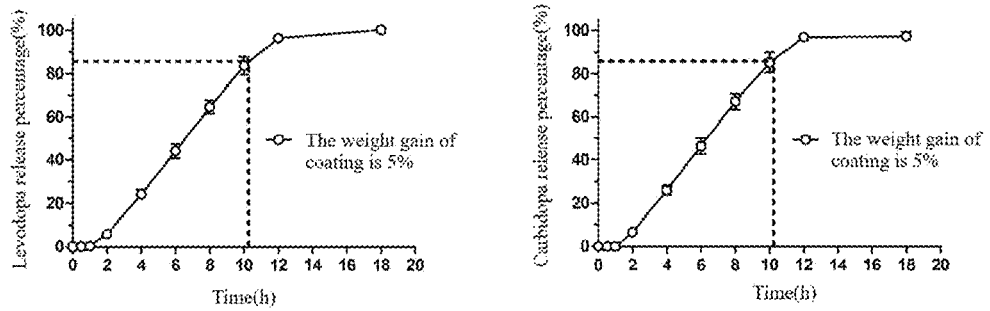
FIG. 9 is a release profile of the extended release platform (ERP) described in embodiment 7, and error bars indicate a standard deviation of n=3.

Next, the bi-layer tablet core was coated with a semi-permeable membrane. The membrane-forming composition comprises, in weight percentage, 70 wt % of cellulose acetate with 39.8 wt % of acetyl content and 30 wt % of copovidone VA64. The membrane-forming composition was mixed with acetone to form a 4% of solid suspension. Using the process parameters listed in embodiment 6, the membrane-forming composition was sprayed onto the bi-layer tablet cores in a Glatt GC 1 pan coater to form a coating membrane, and the membrane weight gain of the coated tablet was 5.0%. Finally, a 0.5 mm exit orifice was drilled mechanically on the drug layer side of the dosage form. Residual solvents were removed by drying the dosage form at 40° C. and ambient humidity for 24 hours. The release profile of the final manufactured dosage form was measured using a USP I paddle method in an aqueous solution of 0.1 N HCl. The final manufactured dosage form delivered LD and CD at an average rate of 17.0 mg/hr and 4.6 mg/hr, respectively, with 85% of LD/CD delivered in 10.0 hours. FIG. 9 depicts the consistent release profiles for both LD and CD. The osmotic delivery system can be kept in oral cavity until the osmotic layer reached the delivery orifice, or kept there for 6-7 hours, and then was swallowed, or it was fastened on the corresponding teeth in the oral cavity and maintained there for 10 hours after combination with the retention enabling platform REP.

Embodiment 8 Preparation of Extended Release Platform

Figure 10:
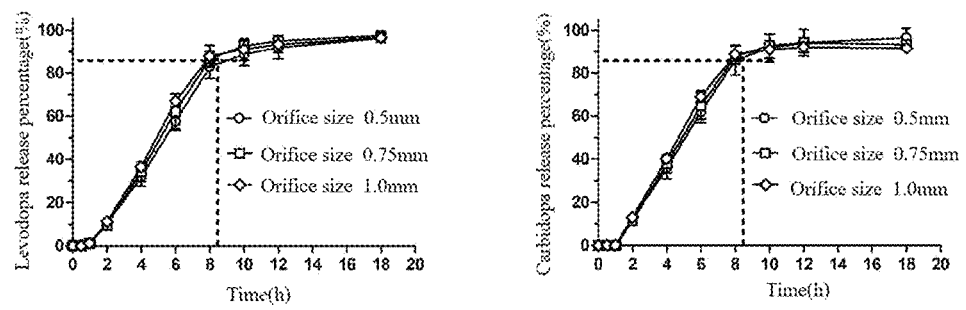
FIG. 10 is a release profile of the extended release platform (ERP) described in embodiment 8, and error bars indicate a standard deviation of n=3.

In this embodiment, the procedures of Embodiment 7 were repeated, and the dosage form consisted of the drug layer, osmotic layer, and coating membrane was identical to those provided in Embodiment 6. In this example, the membrane weight gain was 4.0%, and the size of the delivery orifice varied from 0.5 mm, 0.75 mm, to 1.0 mm. The final manufactured dosage form delivered LD and CD at an average rate of 21.3 mg/hr and 5.7 mg/hr, respectively, with 85% of LD/CD delivered in 8.0 hours. As shown in FIG. 10, the size of the delivery orifice has no significant impact on the release profile. The osmotic delivery system can be kept in oral cavity until the osmotic layer reached the delivery orifice, or kept there for 4-5 hours, and then was swallowed, or it was fastened on the corresponding teeth in the oral cavity and maintained there for 8 hours after combination with the retention enabling platform REP.

Embodiment 9 Preparation of Extended Release Platform

Figure 11:
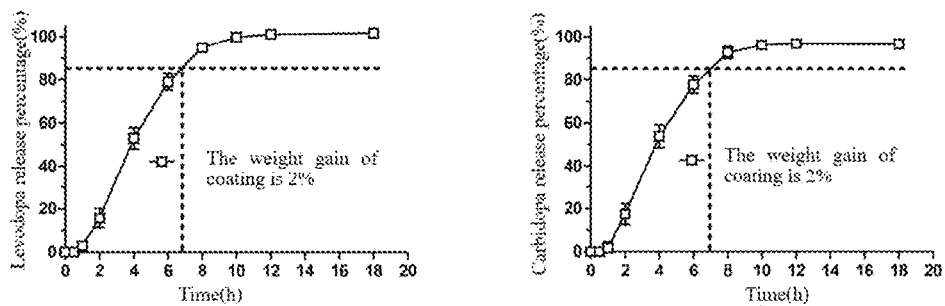
FIG. 11 is a release profile of the extended release platform (ERP) described in embodiment 9, and error bars indicate a standard deviation of n=3.

In this embodiment, the procedures of Embodiment 7 were repeated, and the dosage form consisted of the drug layer was identical to those provided in example 2, while the osmosis layer comprised sodium carboxymethyl cellulose 9H4XF instead of 7H4XF. In this Embodiment, the membrane-forming composition and the size of the delivery orifice were also identical to those in Embodiment 6. The coating membrane weight gain of the dosage form was 2.0%. As shown in FIG. 11, the dosage form delivered LD and CD at an average rate of 24.3 mg/hr and 6.6 mg/hr, respectively, with 85% of LD/CD delivered in 7.0 hours. The osmotic delivery system can be kept in oral cavity until the osmotic layer reached the delivery orifice, or kept there for 3-4 hours, and then was swallowed, or it was fastened on the corresponding teeth in the oral cavity and maintained there for 7 hours after combination with the retention enabling platform REP.

Embodiment 10 Preparation of Extended Release Platform

Figure 12:
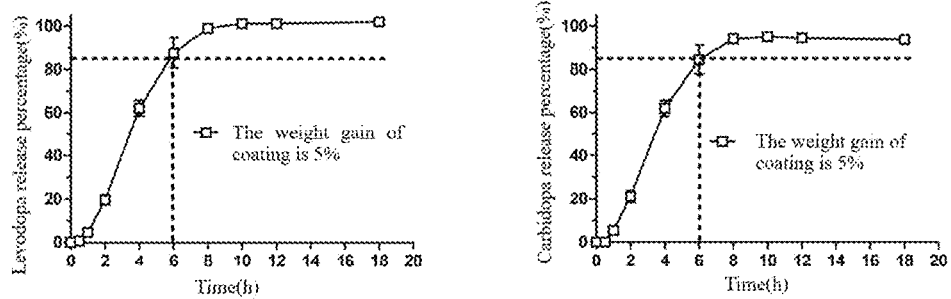
FIG. 12 is a release profile of the extended release platform (ERP) described in embodiment 10, and error bars indicate a standard deviation of n=3.

In this embodiment, the procedures of Embodiment 7 were repeated, and the dosage form consisted of the drug layer and osmotic layer was identical to those provided in Embodiment 7, while the membrane-forming composition comprised 60 wt % of cellulose acetate of cellulose acetate with an acetyl content of 39.8% and 40$W_t$% of copovidone VA64. The membrane weight gain was 5.0%. As shown in FIG. 12, the dosage form delivered 85% of LD/CD in 6 hours. The osmotic delivery system can be kept in oral cavity until the osmotic layer reached the delivery orifice, or kept there for 2-3 hours, and then was swallowed, or it was fastened on the corresponding teeth in the oral cavity and maintained there for 6 hours after combination with the retention enabling platform REP.

Embodiment 11 Preparation of Extended Release Platform

Figure 13:
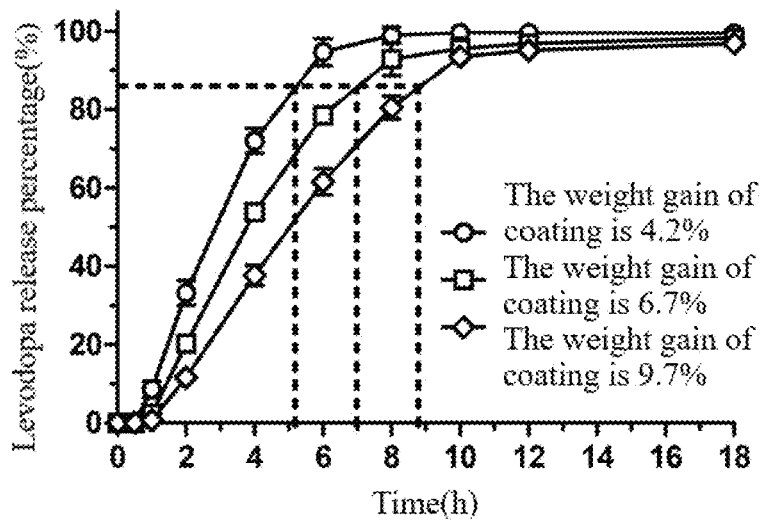
FIG. 13 is a release profile of the extended release platform (ERP) described in embodiment 11, and error bars indicate a standard deviation of n=3.

In this embodiment, the procedures of embodiment 7 were repeated to provide a dosage form.
In this embodiment, the drug layer comprised 45.0$W_t$% of LD, 31.0$W_t$% of hydroxypropyl cellulose (Klucel EXF), 16.0$W_t$% of mannitol, 5.0$W_t$% of Povidone K30, 1.0$W_t$% of aspartame, 1.0$W_t$% of Mint flavor and 1.0$W_t$% of magnesium stearate. The osmosis layer comprised 55$W_t$% of sodium carboxymethyl cellulose 7H4XF, 34.0$W_t$% of sorbitol, 10.0$W_t$% of Povidone K30 and 0.5$W_t$% of iron oxide red and 0.5$W_t$% of magnesium stearate.
The drug layer (500 mg) and osmotic layer granules (250 mg) were compressed into a bi-layer tablet core using a 16×7 capsule-shape tooling.
The bi-layer tablet core was wrapped with the semipermeable membrane, and the weight gains were 4.2$W_t$%, 6.7% and 9.7%, respectively. The membrane-forming composition comprised 60 wt % of cellulose acetate having an acetyl content of 39.8%, 40 wt % of Copovidone VA64. A 1.0 mm exit orifice was drilled mechanically on the drug layer side of the dosage form. Residual solvents were removed by drying the dosage form at 40° C. and ambient humidity for 24 hours.
As shown in FIG. 13, the dosage form delivered LD at an average rate of 38.3 mg/hr, 27.3 mg/hr, and 21.3 mg/hr, and the membrane weight gains were 4.2%, 6.7%, and 9.7%, respectively, with 85% of LD delivered in 5.0 hours, 7.0 hours and 9.0 hours.

Embodiment 12 Preparation of Extended Release Platform

Figure 14:
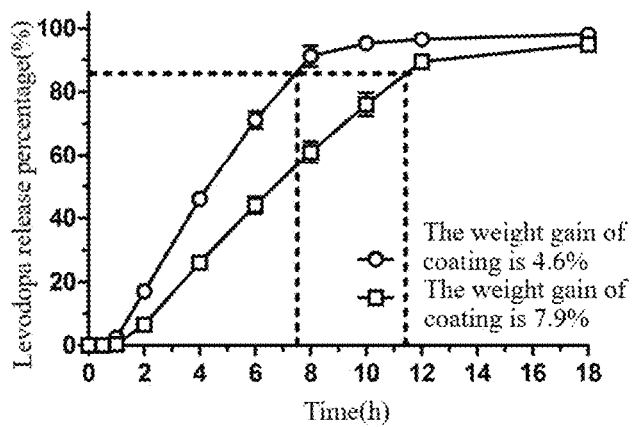
FIG. 14 is a release profile of the extended release platform (ERP) described in embodiment 12, and error bars indicate a standard deviation of n=3.

In this embodiment, the procedures of embodiment 11 were repeated to provide a dosage form other than a membrane-forming composition. In this embodiment, the bi-layer tablet core comprises a membrane-forming composition comprising 70 wt % of cellulose acetate with 39.8% acetyl content and 30 wt % of copovidone VA 64 in weight percentage. The membrane-forming composition was dissolved in a mixed solvent comprising 90% acetone, 9.0% ethanol and 1.0% deionized water to produce a 4% of solid suspension. As shown in FIG. 14, the dosage forms with membrane weight gain of 4.6% and 7.9% delivered LD at an average rate of 25.5 mg/hr and 16.9 mg/hr, respectively, and correspondingly with 85% of LD delivered at 7.5 hours and 11.5 hours.

Embodiment 13 Preparation of Extended Release Platform

Figure 15:
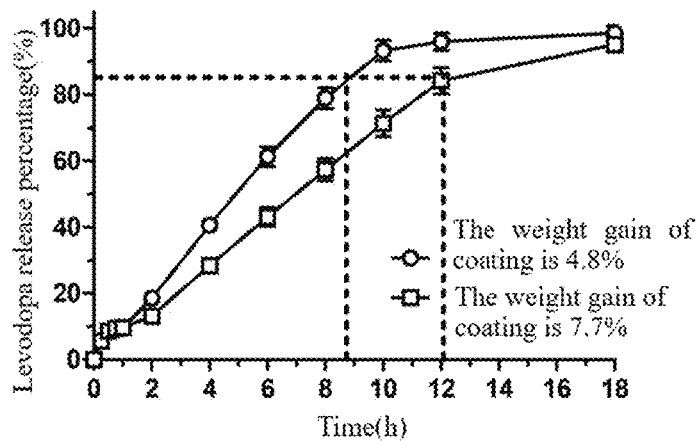
FIG. 15 is a release profile of the extended release platform (ERP) described in embodiment 13, and error bars indicate a standard deviation of n=3.

In this embodiment, the procedures of embodiment 12 were repeated to provide a dosage form. In this embodiment, an immediate release composition comprising 23.78 wt % of LD, 64.22 wt % of CD, 10 wt % of hydroxypropyl cellulose, 1 wt % of aspartame and 1 wt % of Mint Flavor was used to overcoat the dried dosage form with 4.8% and 7.7% membrane weight gain (as shown in c of FIG. 3C). The immediate release overcoat composition was mixed with ethanol to form a 6.7% solid suspension. The final dosage form comprised an immediate-release coating comprising 62.5 mg of CD and 25 mg of LD, and a controlled-release drug layer comprising 225 mg of LD. As shown in FIG. 15, the release profile of the dosage form showed rapid release of LD/CD, followed by an extended release with a release duration of approximately 8.5 hours and 12.0 hours, respectively. The osmotic delivery system having a membrane weight gain of 4.8% can be kept in oral cavity for 4-5 hours, and then kept in oral cavity at meal time or for the whole release duration. The osmotic delivery system having a membrane weight gain of 7.7% can be kept in oral cavity for 8-9 hours before swallowed, or kept in oral cavity for the whole release duration, or fastened on the corresponding teeth in the oral cavity after being combined with the retention enabling platform REP and maintained there for 12 hours.

Embodiment 14 Preparation of Extended Release Platform

In this embodiment, the procedures of Embodiment 6 were repeated, and the dosage form comprised a drug layer and a membrane-forming composition were identical to those provided in Embodiment 6. The drug layer comprised, in weight percentage, 38.0$W_t$% of levodopa, 50.0$W_t$% of microcrystalline cellulose, 2.0W$_t$% of magnesium stearate and 10.0W$_t$% of hydroxypropyl methylcellulose. The coating membrane comprised 50W$_t$% of acetyl acetate membrane with an acetyl content of 39.8% and 50W$_t$% of Copovidone VA64. In this example, the membrane weight gain was 4.50%. The final manufactured dosage form delivered levodopa at an average rate of 9.4 mg/hr, with 85% of levodopa delivered in 9.0 hours.

Embodiment 15 Preparation of Extended Release Platform

In this embodiment, the procedures of Embodiment 6 were repeated, and the dosage form comprised a drug layer and a membrane-forming composition were identical to those provided in Embodiment 6. The drug containing layer comprised, in weight percentage, 19.5W$_t$% of levodopa, 20.0W$_t$% of carbidopa, 50.0W$_t$% of mannitol and 10.0W$_t$% of citric acid. The coating membrane comprised 50W$_t$% of acetyl acetate membrane with an acetyl content of 39.8% and 50W$_t$% of Copovidone VA64. In this example, the membrane weight gain was 4.50%. The final manufactured dosage form delivered levodopa at an average rate of 22.9 mg/hr, with 85% of levodopa delivered in 13.0 hours.

Embodiment 16 Preparation of Extended Release Platform

In this embodiment, the procedures of Embodiment 7 were repeated, and the dosage form comprised a drug layer, an osmosis layer and a membrane-forming composition were identical to those provided in Embodiment 7. The drug layer comprised, in weight percentage, 70.0W$_t$% of levodopa, 9.0W$_t$% of mannitol, 20.0% of Povidone K30 and 1.0W$_t$% of magnesium stearate. The osmosis layer comprised, in weight percentage, 85.0W$_t$% of sodium carboxymethyl cellulose (7H4XF), 3.0W$_t$% of Povidone K30, 5.0W$_t$% of sorbitol, 5.0W$_t$% of iron oxide red and 2.0W$_t$% of magnesium stearate. The coating membrane comprised, in weight percentage, 70.0W$_t$% of acetyl acetate membrane with an acetyl content of 39.8% and 30W$_t$% of Copovidone VA64. In this example, the membrane weight gain was 4.5%. The final manufactured dosage form delivered levodopa at an average rate of 35.0 mg/hr, with 85% of levodopa delivered in 8.5 hours.

Embodiment 17 Preparation of Extended Release Platform

In this embodiment, the procedures of Embodiment 7 were repeated, and the dosage form comprised a drug layer, an osmosis layer and a membrane-forming composition were identical to those provided in Embodiment 2. The drug layer comprised, in weight percentage, 20.0W$_t$% of levodopa, 20.0W$_t$% of carbidopa, 50.0W$_t$% of hydroxypropyl cellulose, 4.0W$_t$% of mannitol, 5.0W$_t$% of aspartame and 1.0W$_t$% of magnesium stearate. The osmosis layer comprised, in weight percentage, 25.0W$_t$% of sodium carboxymethyl cellulose (7H4XF), 9.5W$_t$% of Povidone K30, 65.0W$_t$% of sorbitol and 0.5W$_t$% of magnesium stearate. The coating membrane comprised, in weight percentage, 90W$_t$% of acetyl acetate membrane with an acetyl content of 39.8% and 10W$_t$% of Copovidone VA64. In this example, the membrane weight gain was 4.5%. The final manufactured dosage form delivered levodopa and CD at an average rate of 7.1 mg/hr, with 85% of levodopa/CD delivered in 12 hours.

Embodiment 18 Preparation of Extended Release Platform

In this embodiment, the procedures of Embodiment 13 were repeated, and the dosage form comprised a drug layer, an osmosis layer, a membrane-forming composition and an overcoat were identical to those provided in Embodiment 13. The drug layer comprised, in weight percentage, 45.0W$_t$% of levodopa, 31.0W$_t$% of hydroxypropyl cellulose, 17.0W$_t$% of mannitol, 5.0W$_t$% of Povidone K30, 1.0W$_t$% of magnesium stearate and 1.0W$_t$% of aspartame. The osmosis layer comprised, in weight percentage, 60.0W$_t$% of sodium carboxymethyl cellulose (7H4XF), 10.0W$_t$% of Povidone K30, 26.0W$_t$% of sorbitol, 2.0W$_t$% of iron oxide red and 2.0W$_t$% of magnesium stearate. The coating membrane comprised, in weight percentage, 70W$_t$% of acetyl acetate membrane with an acetyl content of 39.8% and 30W$_t$% of Copovidone VA64. The weight of the coating membrane was 4.5% of the mass of the tablet core. The immediate-release overcoat comprised, in weight percentage, 93.0W$_t$% of CD, 2.0W$_t$% of hydroxypropyl cellulose EF and 5.0W$_t$% of aspartame; the mass of the overcoat was 13.2% of the mass of the tablet core (table core+first layer coating membrane comprising cellulose acetate and Copovidone VA64). The immediate-release overcoat of the dosage form was first released rapidly, followed by an extended release with a release duration of approximately 8 hours. The osmotic delivery system can be kept in oral cavity for 4-5 hours and then swallowed before meal time or kept in oral cavity for the whole release duration, or fastened on the corresponding teeth in the oral cavity after being combined with the retention enabling platform REP and maintained there for 8 hours.

Embodiment 19 Preparation of Extended Release Platform

In this embodiment, the procedures of embodiment 13 were repeated, and the dosage form comprised a drug layer, an osmosis layer, a membrane-forming composition and an overcoat were identical to those provided in Embodiment 13. The drug layer comprised, in weight percentage, 45.0W$_t$% of levodopa, 31.0W$_t$% of hydroxypropyl cellulose, 12.0W$_t$% of mannitol, 5.0W$_t$% of Povidone K30, 5.0W$_t$% of Mint flavor, 1.0W$_t$% of magnesium stearate and 1.0W$_t$% of aspartame. The osmosis layer comprised, in weight percentage, 40.0W$_t$% of sodium carboxymethyl cellulose (7H4XF), 20.0W$_t$% of Povidone K30, 36.0W$_t$% of sorbitol, 3.5W$_t$% of iron oxide red and 0.5W$_t$% of magnesium stearate. The coating membrane comprised, in weight percentage, 70W$_t$% of acetyl acetate membrane with an acetyl content of 39.8% and 30W$_t$% of copovidone VA64. The weight of the coating membrane was 4.5% of the mass of the tablet core. The immediate-release overcoat comprised, in weight percentage, 75.0W$_t$% of LD, 20.0W$_t$% of hydroxypropyl cellulose and 5.0W$_t$% Mint flavor; the mass of the overcoat was 13.2% of the mass of the tablet core (table core+first layer coating membrane comprising cellulose acetate and Copovidone VA64). The immediate-release overcoat of the dosage form was first released rapidly, followed by an extended release with a release duration of approximately 8 hours. The osmotic delivery system can be kept in oral cavity for 4-5 hours and then be swallowed before meal time or kept in oral cavity for the whole release duration, or fastened on the corresponding teeth in the oral cavity after being combined with the retention enabling platform REP and maintained there for 8 hours.

Embodiment 20 Preparation of Extended Release Platform

In this embodiment, the procedures of embodiment 8 were repeated, and the dosage form comprised a drug layer, an osmosis layer, a membrane-forming composition and an overcoat were identical to those provided in example 8. The drug layer comprised, in weight percentage, 45.0$W_t$% of levodopa, 31.0$W_t$% of hydroxypropyl cellulose, 17.0$W_t$% of mannitol, 5.0$W_t$% of Povidone K30, 1.0$W_t$% magnesium stearate and 1.0$W_t$% of aspartame. The osmosis layer comprised, in weight percentage, 55.0$W_t$% of sodium carboxymethyl cellulose (7H4XF), 10.0$W_t$% of hydroxypropyl cellulose, 34.0$W_t$% sorbitol, 0.5$W_t$% of iron oxide red and 0.5$W_t$% of magnesium stearate. The coating membrane comprised, in weight percentage, 70$W_t$% of acetyl acetate membrane with an acetyl content of 39.8% and 30$W_t$% of copovidone VA64. The weight of the coating membrane was 5.9% of the mass of the tablet core. The solid content of the immediate-release overcoat suspension was 10.0$W_t$%, comprising, in weight percentage, 24.0$W_t$% of levodopa, 65.0$W_t$% of carbidopa monohydrate, 10.0$W_t$% of hydroxypropyl cellulose and 1.0$W_t$% of aspartame; the weight of the overcoat was 13.2% of the weight of the tablet core (table core+first layer coating membrane comprising cellulose acetate and Copovidone VA64). When the solvent for the overcoat suspension was anhydrous ethanol, the level of the carbidopa-related genotoxic impurity hydrazine in the obtained dosage form was 1.7 ppm, and the level of the carbidopa-related impurity dihydroxyphenylacetone (DHPA) was 0.21%. When the solvent for the coating suspension of the overcoat was purified water, the solid content of the overcoat was 10.0$W_t$%, comprising, in weight percentage, 24.0$W_t$% of levodopa, 65.0$W_t$% of carbidopa monohydrate, 10.0$W_t$% of hydroxypropyl cellulose and 1.0$W_t$% of aspartame; the level of the carbidopa-related genotoxic impurity hydrazine in the obtained dosage form was 3.8 ppm, and the level of the carbidopa-related impurity DHPA was 0.28%. The carbidopa-related genotoxic impurity hydrazine and impurity DHPA of the obtained dosage form when the solvent for the coating suspension of the overcoat was anhydrous ethanol, were significantly lower than those of the obtained dosage form when the solvent for the coating suspension was purified water. The immediate-release overcoat of the dosage form was first released rapidly, followed by a sustained release with a duration of approximately 8 hours. The dosage form can be held in the oral cavity for 3-5 hours, and then be swallowed before meal time or kept in oral cavity for the whole release duration.

Embodiment 21 Preparation of Extended Release Platform (Each Tablet Contains 62.5 mgCD+500 mgLD)

Dosage forms that were designed, shaped and suitable for dispensing the beneficial drugs levodopa and carbidopa monohydrate to the oral cavity were prepared as follows: First, a drug-containing layer composition was prepared, which comprises, in weight percentage, 67.9 wt % of LD, 25.1 wt % of hydroxypropyl cellulose with an average molecular weight of 80,000, 5.0 wt % of povidone K30, and 1.0 wt % of aspartame. The excipients were sieved by a 40 mesh stainless steel sieve respectively, then mixed with pure water and granulated until a homogenous wet substance was formed; the wet substance was sieved by a 4×4 mm sieve and dried at 60° C. for 1 hour; the dried granules were sieved by a Φ1.5 mm sieve, and then mixed with 1.0 wt % of magnesium stearate.

Next, a second composition, an osmotic layer, which comprises 55.0 wt % of sodium carboxymethylcellulose 7H4XF, 39.0 wt % of sorbitol, 5.0 wt % of povidone K30 and 0.5 wt % of iron oxide red, was prepared; each of these components was sieved by 40 mesh stainless steel sieve, and then mixed with 95% ethanol and granulated until a homogenous wet substance was formed; the wet substance was sieved by a 4×4 mm sieve and dried at 80° C. for 2 hours; the dried granules were sieved by a Φ1.2 mm sieve, and then mixed with 0.5 wt % of magnesium stearate.

Next, the drug-containing layer and the osmotic layer granules were pressed into a bi-layer tablet core. First, 700 mg of the drug-containing layer granules were added to the 19×7.5 mm special-shaped punch of the tablet press and compacted, then 350 mg of the osmotic layer granules were added to the punch, and the two layers of granules were pressed into a contact bi-layer tablet core by the tablet press.

Next, the bi-layer tablet core was coated with a semipermeable membrane. The membrane-forming composition comprised, in weight percentage, 70 wt % of cellulose acetate with an acetyl content of 39.8 wt % and 30 wt % of copovidone VA64. The membrane-forming composition was mixed with acetone to form a 4% of solid suspension. Using the technological parameters listed in embodiment 6, the membrane-forming composition was sprayed onto the bi-layer tablet cores in a Glatt GC 1 pan coater to form a coating membrane. The membrane weight gain of the coated tablets was 5.0%. Finally, a 1.0 mm exit orifice was mechanically drilled on the side of drug-containing layer of the dosage form. Residual solvent was removed by drying the dosage forms at 40° C. and ambient humidity for 72 hours. Immediate release overcoat comprised, in weight percentage, 24.1 wt % of LD, 64.9 wt % of CD, 10.0 wt % of hydroxypropyl cellulose and 1.0 wt % of aspartame; the weight of the overcoat was 9.4% of the weight of the tablet core (table core+first coating membrane cellulose acetate and copovidone VA64). The immediate release overcoat of the dosage form was rapidly released first, then released for an extended release with a duration of approximately 16 hours. The osmotic delivery system can be maintained in the oral cavity for 16 hours, maintained in the oral cavity during the entire release duration, or fastened on the corresponding teeth in the oral cavity after being combined with the retention enabling platform REP and maintained there for 16 hours.

Embodiment 22 Preparation of Extended Release Platform (Each Tablet Comprises 62.5 mgCD+375 mgLD)

In this embodiment, the procedures of embodiment 20 were repeated, and the dosage form comprising a drug-containing layer, an osmotic layer, a membrane-forming composition and an overcoat was identical to those provided in embodiment 20. The drug-containing layer comprised, in weight percentage, 53.5 wt % of LD, 39.5 wt % of hydroxypropyl cellulose with an average molecular weight of 80,000, 5.0 wt % of povidone K30, 1.0 wt % of aspartame and 1.0 wt % of magnesium stearate. The osmotic layer comprised, in weight percentage, 55.0 wt % of sodium carboxymethylcellulose 7H4XF, 39.0 wt % of sorbitol, 5.0 wt % of povidone K30, 0.5 wt % of iron oxide red and 0.5 wt % of magnesium stearate. The membrane-forming composition comprised, in weight percentage, 70 wt % of cellulose acetate with 39.8 wt % of acetyl content, and 30 wt % of copovidone VA64. The weight of the overcoat is 9.4% of the weight of the tablet core (table core+first coating membrane cellulose acetate and copovidone VA64). The immediate release overcoat of the dosage form was rapidly released first, then released for an extended release with a duration of approximately 16 hours. The osmotic delivery system can be maintained in the oral cavity for 16 hours, maintained in the oral cavity during the entire release duration, or fastened on the corresponding teeth in the oral cavity after being combined with the retention enabling platform REP and maintained there for 16 hours.

Embodiment 23 Preparation of Extended Release Platform (Each Tablet Contains 50 mgCD+500 mgLD)

Dosage forms that were designed, shaped and suitable for dispensing the beneficial drugs levodopa and carbidopa monohydrate to the oral cavity were prepared as follows: First, a drug-containing layer composition was prepared, which comprises 62.5 wt % of LD, 31 wt % of hydroxypropyl cellulose with an average molecular weight of 80,000, 4.5 wt % of mannitol, 0.9 wt % of aspartame, 0.1% wt % of Mint Flavor and 0.5 wt % of magnesium stearate, these excipients were made by dry granulation, then sieved by a 1.2 mm sieve, and then mixed with 0.5 wt % of magnesium stearate.

Next, a second composition, an osmotic layer, which comprises 55.0 wt % of sodium carboxymethylcellulose 7H4XF, 34.0 wt % of sorbitol, 10 wt % of hydroxypropyl cellulose and 0.5 wt % of iron oxide red, was prepared; these excipients were made by dry granulation, then sieved by a 1.2 mm sieve, and then mixed with 0.5 wt % of magnesium stearate.

Next, the drug-containing layer and the osmotic layer granules were pressed into a bi-layer tablet core. First, 600 mg of the drug-containing layer granules were added to the 19×7.5 mm special-shaped punch of the tablet press and compacted, then 300 mg of the osmotic layer granules were added to the punch, and the two layers of granules were pressed into a contact bi-layer tablet core by the tablet press.

Figure 16:
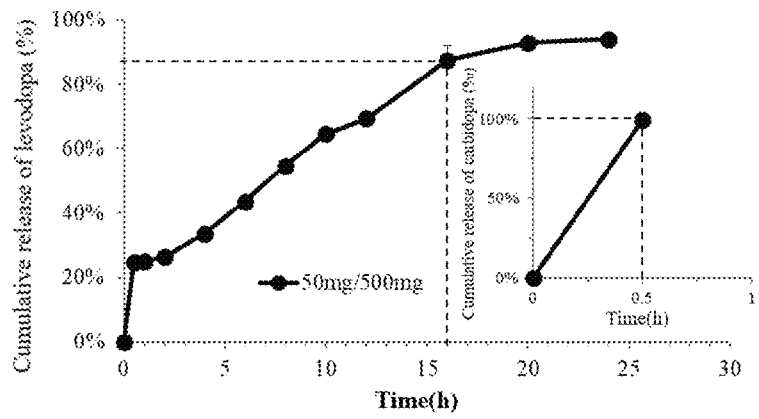
FIG. 16 is a release profile of the extended release platform (ERP) described in embodiment 14, and error bars indicate a standard deviation of n=3.

Next, the bi-layer tablet core was coated with a semi-permeable membrane. The membrane-forming composition comprised, in weight percentage, 70 wt % of cellulose acetate with 39.8 wt % of acetyl content, and 30 wt % of copovidone VA64. The membrane-forming composition was mixed with acetone to form a 4% of solid suspension. Using the technological parameters listed in embodiment 6, the membrane-forming composition was sprayed onto the bi-layer tablet cores in a Glatt GC 1 pan coater to form a coating membrane. The membrane weight gain of the coated tablets was 6.5%. Finally, a 1.0 mm exit orifice was mechanically drilled on the drug-containing layer side of the dosage form. The immediate release overcoat comprised, in weight percentage, 62.15 wt % of LD, 26.85 wt % of CD, 10.0 wt % of hydroxypropyl cellulose and 0.9 wt % of aspartame; the weight of the overcoat is 21.0% of the weight of the tablet core (table core+first coating membrane cellulose acetate and copovidone VA64). As shown in FIG. 16, the release profile of the dosage form showed rapid release of LD/CD, followed by an extended release with a duration of approximately 16 hours. The osmotic delivery system can be maintained in the oral cavity for 16 hours, maintained in the oral cavity during the entire release duration, or fastened on the corresponding teeth in the oral cavity after being combined with the retention enabling platform REP and maintained there for 16 hours.

Embodiment 24 Preparation of Extended Release Platform (Each Tablet Contains 37.5 mgCD+375 mgLD)

Dosage forms that were designed, shaped and suitable for dispensing the beneficial drugs levodopa and carbidopa monohydrate to the oral cavity were prepared as follows: First, a drug-containing layer composition was prepared, which comprised 46.9 wt % of LD, 31.0 wt % of hydroxypropyl cellulose with an average molecular weight of 80,000, 20.1 wt % of mannitol, 0.9 wt % of aspartame, 0.1% wt % of Mint Flavor and 0.5 wt % of magnesium stearate, these excipients were made by dry granulation, then sieved by a 1.2 mm sieve, and then mixed with 0.5 wt % of magnesium stearate.

Next, a second composition, the osmotic layer, which comprised 55.0 wt % of sodium carboxymethylcellulose 7H4XF, 34.0 wt % of sorbitol, 10 wt % of hydroxypropyl cellulose and 0.5 wt % of iron oxide red, was prepared; these excipients were made by dry granulation, sieved by a 1.2 mm sieve, and then mixed with 0.5 wt % of magnesium stearate.

Next, the drug-containing layer and the osmotic layer granules were pressed into a bi-layer tablet core. First, 600 mg of the drug-containing layer granules were added to the 19×7.5 mm special-shaped punch of the tablet press and compacted, then 300 mg of the osmotic layer granules were added to the punch, and the two layers of granules were pressed into a contact bi-layer tablet core by the tablet press.

Figure 17:
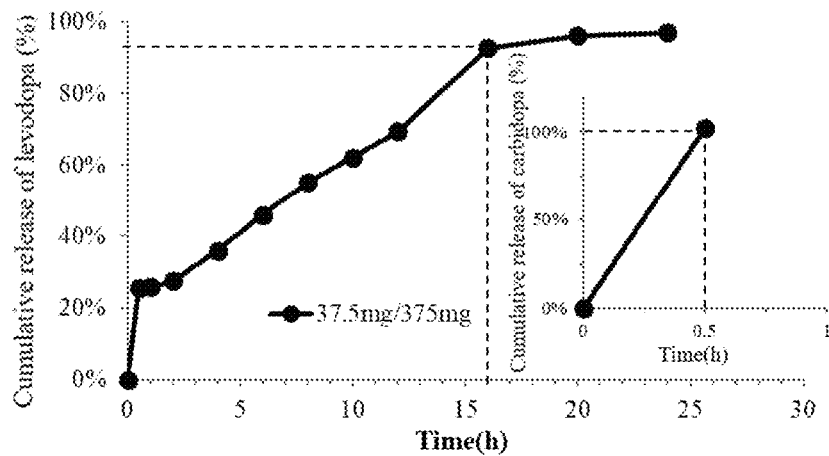
FIG. 17 is a release profile of the extended release platform (ERP) described in embodiment 15, and error bars indicate a standard deviation of n=3.

Next, the bi-layer tablet core was coated with a semi-permeable membrane. The membrane-forming composition comprised, in weight percentage, 70 wt % of cellulose acetate with 39.8 wt % of acetyl content, and 30 wt % of copovidone VA64. The membrane-forming composition was mixed with acetone to form a 4% of solid suspension. Using the technological parameters listed in embodiment 6, the membrane-forming composition was sprayed onto the bi-layer tablet cores in a Glatt GC 1 pan coater to form a coating membrane. The membrane weight gain of the coated tablets was 6.5%. Finally, a 1.0 mm exit orifice was mechanically drilled on the drug-containing layer side of the dosage form. The immediate release overcoat comprised, in weight percentage 62.15 wt % of LD, 26.85 wt % of CD, 10.0 wt % of hydroxypropyl cellulose and 0.9 wt % of aspartame; the weight of the overcoat was 15.7% of the weight of the tablet core (table core+first coating membrane cellulose acetate and copovidone VA64). As shown in FIG. 17, the release profile of the dosage form showed rapid release of LD/CD, followed by extended release with a duration of approximately 16 hours. The osmotic delivery system can be maintained in the oral cavity for 16 hours, maintained in the oral cavity during the entire release duration, or fastened on the corresponding teeth in the oral cavity after being combined with the retention enabling platform REP and maintained there for 16 hours.

Embodiment 25 Preparation of Extended Release Platform (Each Tablet Comprises 37.5 mgCD+250 mgLD)

Firstly, a drug layer composition comprising $45.0W_t\%$ of levodopa, $31.0W_t\%$ of hydroxypropyl cellulose, $22.0W_t\%$ of mannitol, $0.9W_t\%$ of aspartame, $0.1W_t\%$ of Mint flavor and $0.5W_t\%$ of magnesium stearate was prepared, the components were each passed through a 40-mesh stainless steel sieve and granulated to obtain dry granules by a dry granulator, and then mixed with 0.5$W_t$% of magnesium stearate.

Next, a second composition, an osmosis layer, comprising 55.0$W_t$% of sodium carboxymethyl cellulose 7H4XF, 34.0$W_t$% of sorbitol, 10.0$W_t$% of hydroxypropyl cellulose and 0.5$W_t$% of iron oxide red was prepared; the components were respectively passed through a 40-mesh stainless steel sieve and then dried to obtain dry granules by a dry granulator, and then mixed with 0.5$W_t$% of magnesium stearate.

Next, the drug layer and osmotic layer granules were compressed into a bi-layer tablet core. First, 417 mg of drug layer granules were added to the 16×7 mm punch and tamped, and 208 mg of osmotic layer granules were added, then the two layers of granules were compressed into a contact bi-layer tablet core with a tablet press.

Next, the bi-layer tablet core was coated with a semipermeable membrane. The membrane-forming composition comprised, in weight percentage, 70$W_t$% of cellulose acetate with an acetyl content of 39.8$W_t$%, and 30$W_t$% of Copovidone VA64. The membrane-forming composition was mixed with acetone to make a solution with 4% of solid suspension. Using the process parameters listed in Embodiment 6, the membrane-forming composition was sprayed onto the bi-layer tablet core in a Glatt GC 1 pan coater to form a coating membrane, and the membrane weight gain of the coated tablet was 6.5%. Finally, a 1.0 mm exit orifice was drilled mechanically on the drug layer side of the dosage form.

Next, an immediate-release composition, comprising 54.0$W_t$% of levodopa, 35.0$W_t$% of carbidopa monohydrate, 10.0$W_t$% of hydroxypropyl cellulose, 0.9$W_t$% of aspartame and 0.1$W_t$% of Mint flavor, was used to overcoat the dried dosage form, with the membrane weight gain of 6.5%. The immediate-release overcoat composition was mixed with anhydrous ethanol to make a 10.0$W_t$% of solid suspension. The final dosage form comprises an immediate-release overcoat comprising 62.5 mg of levodopa and 37.5 mg of carbidopa, and a controlled-release drug layer comprising 187.5 mg of levodopa.

Figure 18:
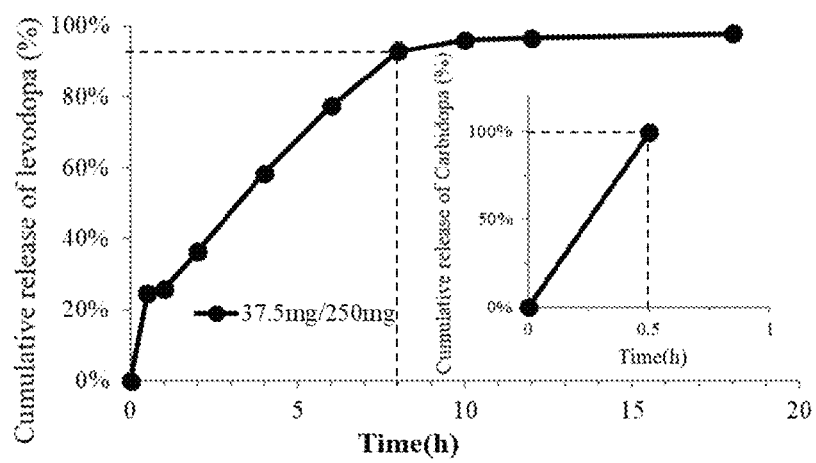
FIG. 18 is a release profile of the extended release platform (ERP) described in embodiment 16, and error bars indicate a standard deviation of n=3.

As shown in FIG. 18, the release profile of the dosage form showed rapid release of LD/CD, followed by an extended release with a release duration of approximately 8 hours. The osmotic delivery system can be kept in oral cavity for 4-5 hours, and then was be swallowed before meal time or kept in oral cavity for the whole release duration.

Embodiment 26 Preparation of Extended Release Platform (Each Tablet Comprises 37.5 mgCD+150 mgLD)

In this embodiment, the procedures of embodiment 25 were repeated, and the dosage form comprising a drug layer, an osmotic layer, a membrane-forming composition and an overcoat were all identical to those provided in embodiment 25.

First, a drug layer composition comprising 45.0$W_t$% of levodopa, 31.0$W_t$% of hydroxypropyl cellulose, 22.0$W_t$% of mannitol, 0.9$W_t$% of aspartame, 0.1$W_t$% of Mint flavor and 0.5$W_t$% of magnesium stearate was prepared, the components were each passed through a 40-mesh stainless steel sieve, and dried to obtain dry granules by a dry granulator, then mixed with 0.5$W_t$% of magnesium stearate.

Next, a second composition, i.e. an osmosis layer, comprising 55.0$W_t$% of sodium carboxymethyl cellulose 7H4XF, 34.0$W_t$% of sorbitol, 10.0$W_t$% of hydroxypropyl cellulose and 0.5$W_t$% of iron oxide red was prepared; the components were each passed through a 40-mesh stainless steel sieve, and dried to obtain dry granules by a dry granulator, then mixed with 0.5$W_t$% of magnesium stearate.

Next, the drug layer and osmotic layer granules were compressed into a bi-layer tablet core. Firstly, 250 mg of drug layer granules were added to a 9 mm round punch of a tablet press and tamped, then 125 mg of osmotic layer granules were added to the punch, and the two layers of granules were compressed with a tablet press into a contact bi-layer tablet core.

Next, the bi-layer tablet core was coated with a semipermeable membrane. The membrane-forming composition comprised, in weight percentage, 70$W_t$% of cellulose acetate with an acetyl content of 39.8$W_t$%, and 30$W_t$% of Copovidone VA64. The membrane-forming composition was mixed with acetone to make a 4% of solid suspension. Using the technological parameters listed in embodiment 6, the membrane-forming composition was sprayed onto the bi-layer tablet core in a Glatt GC 1 pan coater to form a coating membrane, and the membrane weight gain of the coated tablet was 7.0%. Finally, a 0.75 mm exit orifice was drilled mechanically on the drug layer side of the dosage form.

Next, an immediate-release composition, comprising 42.8$W_t$% of levodopa, 46.2$W_t$% of carbidopa monohydrate, 10.0$W_t$% of hydroxypropyl cellulose, 0.9$W_t$% of aspartame and 0.1$W_t$% of Mint Flavor, was used to overcoat the dried dosage form, with the membrane weight gain of 7.0%. The immediate-release overcoat composition was mixed with anhydrous ethanol to make a 10.0$W_t$% of solid suspension. The final dosage form comprises an immediate-release overcoat comprising 37.5 mg of levodopa and 37.5 mg of carbidopa, and a controlled-release drug layer comprising 112.5 mg of levodopa.

Figure 19:
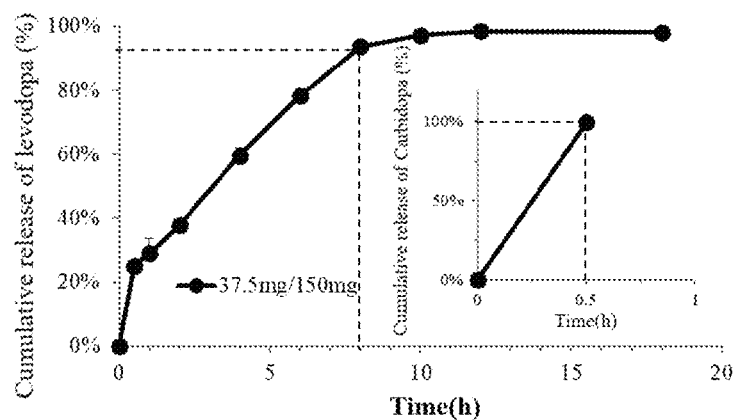
FIG. 19 is a release profile of the extended release platform (ERP) described in embodiment 17, and error bars indicate a standard deviation of n=3.

As shown in FIG. 19, the release profile of the dosage form showed rapid release of LD/CD, followed by an extended release with a release duration of approximately 8 hours. The osmotic delivery system can be kept in oral cavity for 4-5 hours, and then be swallowed before meal time or kept in oral cavity for the whole release duration.

Embodiment 27 Preparation of Extended Release Platform (Each Tablet Contains 37.5 mgCD+75 mgLD)

In this embodiment, the procedures of embodiment 25 were repeated, and the dosage form comprised a drug layer, an osmosis layer, a membrane-forming composition and an overcoat were identical to those provided in embodiment 25.

First, a drug layer composition comprising 45.0$W_t$% of levodopa, 31.0$W_t$% of hydroxypropyl cellulose, 22.0$W_t$% of mannitol, 0.9$W_t$% of aspartame, 0.1$W_t$% of Mint Flavor and 0.5$W_t$% of magnesium stearate was prepared, the components were each passed through a 40-mesh stainless steel sieve, and dried to obtain dry granules by a dry granulator, then mixed with 0.5$W_t$% of magnesium stearate.

Next, a second composition, i.e. an osmosis layer, comprising 55.0$W_t$% of sodium carboxymethyl cellulose 7H4XF, 34.0$W_t$% of sorbitol, 10.0$W_t$% of hydroxypropyl cellulose and 0.5$W_t$% of iron oxide red was prepared; the components were each passed through a 40-mesh stainless steel sieve, and dried to obtain dry granules by a dry granulator, then mixed with 0.5$W_t$% of magnesium stearate.

Next, the drug layer and osmotic layer granules were compressed into a bi-layer tablet core. Firstly, 125 mg of drug layer granules were added to a 7 mm round punch of a tablet press and tamped, then 62.5 mg of osmotic layer granules were added to the punch, and the two layers of granules were compressed into a contact bi-layer tablet core with a tablet press.

Next, the bi-layer tablet core was coated with a semi-permeable membrane. The membrane-forming composition comprised, in weight percentage, 70$W_t$% of cellulose acetate with an acetyl content of 39.8$W_t$%, and 30$W_t$% of Copovidone VA64. The membrane-forming composition was mixed with acetone to make a 4% of solid suspension. Using the process parameters listed in Embodiment 6, the membrane-forming composition was sprayed onto the bi-layer tablet core in a Glatt GC 1 pan coater to form a coating membrane, and the membrane weight gain of the coated tablet was 9.0%. Finally, a 0.5 mm exit orifice was drilled mechanically on the drug layer side of the dosage form.

Next, an immediate-release composition comprising 28.2$W_t$% of levodopa, 60.8$W_t$% of carbidopa monohydrate, 10.0$W_t$% of hydroxypropyl cellulose, 0.9$W_t$% of aspartame and 0.1$W_t$% of Mint flavor, was used to overcoat the dried dosage form, with a membrane weight gain of 9.0%. The immediate-release overcoat composition was mixed with anhydrous ethanol to make a 10.0$W_t$% of solid suspension. The final dosage form comprised an immediate-release overcoat comprising 18.75 mg of levodopa and 37.5 mg of carbidopa, and a controlled-release drug layer comprising 56.25 mg of levodopa.

Figure 20:
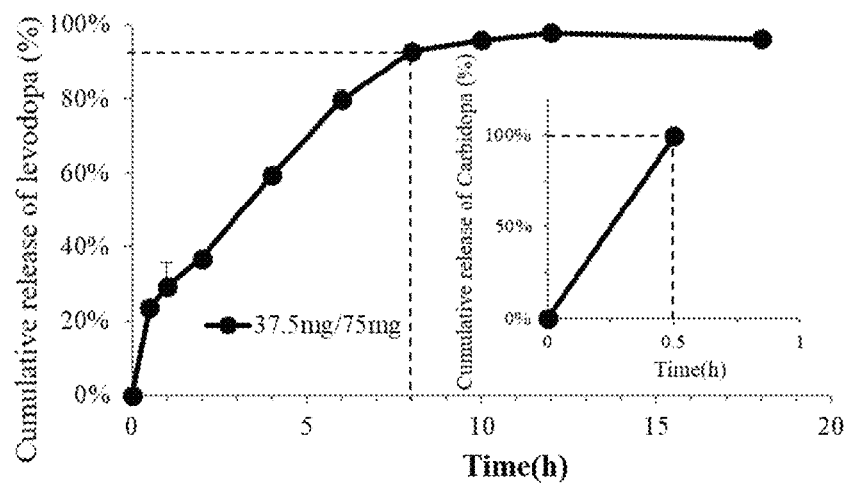
FIG. 20 is a release profile of the extended release platform (ERP) described in embodiment 18, and error bars indicate a standard deviation of n=3.

As shown in FIG. 20, the release profile of the dosage form showed rapid release of LD/CD, followed by an extended release with a release duration of approximately 8 hours. The osmotic delivery system can be kept in oral cavity for 4-5 hours, and then was be swallowed before meal time or kept in oral cavity for the whole release duration.

Embodiment 28 Coordination of Extended Release Platform and Retention Enabling Platform The extended release platform (ERP) of embodiments 6-27 was fastened to the personalized retention enabling platform (REP) of embodiments 1-5 to form the extended release dosage form (ERP+REP) of the present invention. Then, the extended release dosage form (ERP+REP) was fastened on the corresponding teeth in the oral cavity. The extended release dosage form (ERP+REP) can be maintained in the oral cavity until the push layer reaches the delivery orifice, or maintained there for 4-24 hours. The extended release dosage form (ERP+REP) was taken out, the extended release platform (ERP) was replaced, and the extended release dosage form (ERP+REP) was fastened on the corresponding teeth in the oral cavity again, thus releasing the drug continuously.

Embodiment 29 Coordination of Extended Release Platform and Retention Enabling Platform (Each Tablet Comprises 62.5 mgCD+250 mgLD)

In this embodiment, the procedures of embodiment 9 were repeated, the dried dosage form with 4.8% membrane weight gain was coated with an immediate release composition comprising 23.79 wt % of levodopa, 64.22 wt % of carbidopa, 10.0 wt % of hydroxypropyl cellulose and 1.0 wt % of aspartame (as shown in FIG. 3C). The immediate release overcoat composition was mixed with absolute ethanol to make a 6.7 wt % of solid suspension. The final extended release platform ERP dosage form comprises an immediate release coating layer of 62.5 mg carbidopa and 25 mg levodopa, and an extended release drug-containing layer of 225 mg levodopa.

The extended release platform (ERP) was fastened to the personalized retention enabling platform (REP) to form the extended release dosage form (ERP+REP) of the present invention. Then, the extended release dosage form (ERP+REP) was fastened on the corresponding teeth in the oral cavity. The extended release dosage form (ERP+REP) can be maintained in the oral cavity until the push layer reaches the delivery orifice or maintained there for 8 hours. The extended release dosage form (ERP+REP) was taken out, the extended release platform (ERP) was replaced, and the extended release dosage form (ERP+REP) was fastened on the corresponding teeth in the oral cavity again, thus releasing the drug continuously.

Figure 21:
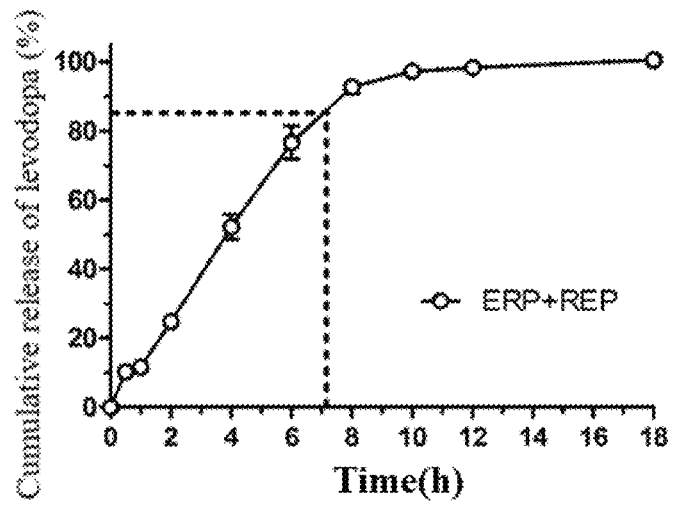
FIG. 21 is a release profile of the extended release platform (ERP+REP) described in embodiment 19, and error bars indicate a standard deviation of n=3.

The USP I basket method was used to determine the release profile of an extended release dosage form (ERP+REP) in a 0.1N hydrochloric acid aqueous solution. As shown in FIG. 21, an extended release dosage form (ERP+REP) with a membrane weight gain of 4.8% delivered LD at an average rate of 27.6 mg/hr, with 85% of LD delivered in 7.7 hours and 85% of CD delivered in 1 hour.

Example 30 Cobalt-Chromium Alloy Back-Insertion Oral Retention Device

Figure 22:
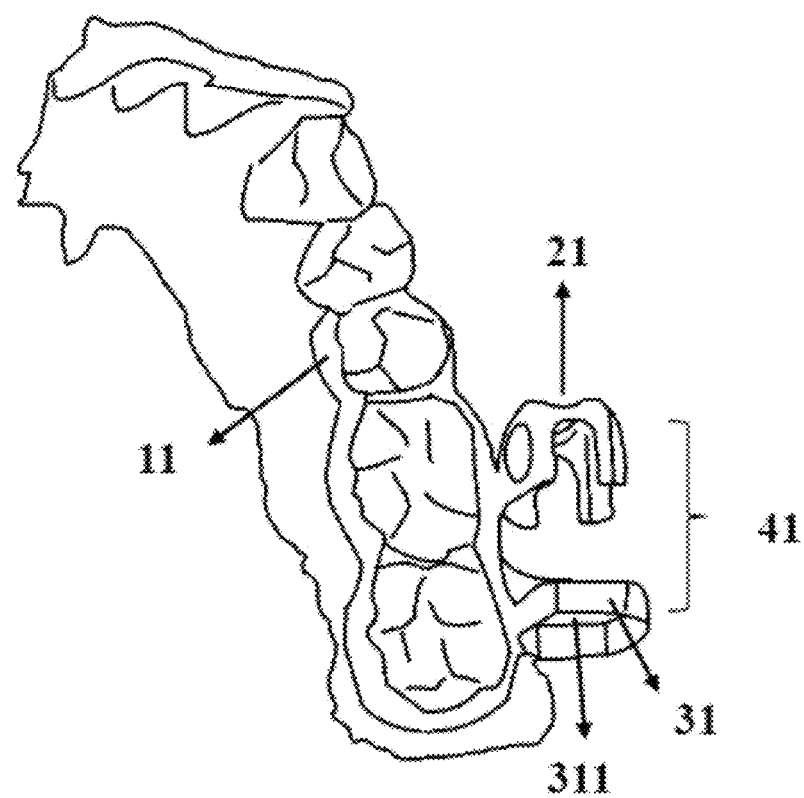
FIG. 22 is an oral retention device with a medicinal tablet being inserted from the back according to an embodiment of the present disclosure, the device being composed of a tooth matching component 11 and a drug-loaded component 41, wherein the drug-loaded component 41 is composed of a retainer 21 and a ring body 31, the ring body 31 being provided with an opening 311.

In the embodiment shown in FIG. 22, the oral retention device with a medicinal tablet being inserted from the back is composed of a tooth matching component 11 and a drug-loaded component 41 connected to each other. The tooth matching component 11 can be closely attached to the teeth in the oral cavity of the subject, and the drug-loaded component 41 is sized to hold at least one medicinal tablet and retain the medicinal tablet in the oral cavity. Both the tooth matching component 11 and the drug-loaded component 41 are made of cobalt-chromium alloy, and the tooth matching component 11 and the drug-loaded component 41 are connected on respective sides. The drug-loaded component comprises a ring body 31 and a retainer 21 that is located at the end. The ring body 31 is a circular closed ring body with an opening 311 for insertion of a medicinal tablet. The retainer and the ring body are arranged at an interval, and are respectively connected to the tooth matching component 11. In another solution, the retainer may be integrally formed with the ring body and then fixed on the tooth matching component, and may also be integrally formed with the ring body and the tooth matching component. After the oral retention device matches with the teeth in the oral cavity of the subject via the tooth matching component, the opening 311 opens toward the molars in the horizontal direction formed by the molars and the incisors (the ring body 31 is located on the molar side in the horizontal direction, that is, the position of the ring body 31 is closer to the molars than the position of the retainer 21), and the medicinal tablet is inserted from the molars toward the incisors in the horizontal direction. The retainer is of a circular arc hollow shape, and has a structure configured to limit the medicinal tablet in the drug-loaded component. The tooth matching component 11 matches the first molar, the second molar and/or the third molar on the mandible in the oral cavity of the subject, and wraps the teeth by means of matching.

Wearing the oral retention device loaded with a medicinal tablet according to this embodiment in the oral cavity, even if the immediate release layer of the drug is quickly dissolved after intensive gargle, the medicinal tablet can be firmly secured and will not slip off the device.

Example 31 Cobalt-Chromium Alloy Front-Insertion Oral Retention Device

Figure 23:
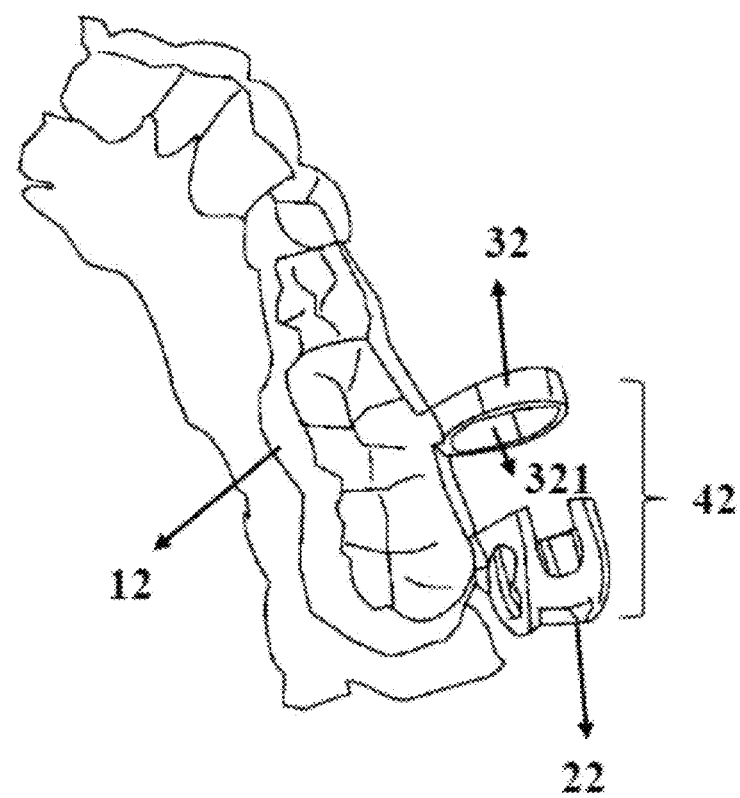
FIG. 23 is an oral retention device with a medicinal tablet being inserted from the front according to an embodiment of the present disclosure, the device being composed of a tooth matching component 12 and a drug-loaded component 42, wherein the drug-loaded component 42 is composed of a retainer 22 and a ring body 32, the ring body 32 being provided with an opening 321.

In the embodiment shown in FIG. 23, the oral retention device with a medicinal tablet being inserted from the front is composed of a tooth matching component 12 and a drug-loaded component 42 connected to each other. The tooth matching component 12 can be closely attached to the teeth in the oral cavity of the subject, and the drug-loaded component 42 is sized to hold at least one medicinal tablet and retain the medicinal tablet in the oral cavity. Both the tooth matching component 12 and the drug-loaded component 42 are made of cobalt-chromium alloy, and the tooth matching component 12 and the drug-loaded component 42 are connected on respective sides. The drug-loaded component 42 comprises a ring body 32 and a retainer 22 that is located at the end. The ring body 32 is a circular closed ring body with an opening 321 for insertion of a medicinal tablet. The retainer and the ring body are arranged at an interval, and are respectively connected to the tooth matching component 11. In another solution, the retainer may be integrally formed with the ring body and then fixed on the tooth matching component, and may also be integrally formed with the ring body and the tooth matching component. The opening 321 opens toward the incisors in the horizontal direction formed by the molars and the incisors (the ring body 32 is located on the molar side in the horizontal direction formed by the molars and the incisors, that is, the position of the ring body 32 is closer to the incisors than the position of the retainer 22), and the medicinal tablet is inserted from the incisors toward the molars in the horizontal direction formed by the molars and the incisors. The retainer is of a circular arc hollow shape, and the retainer has a structure configured to limit the medicinal tablet in the drug-loaded component. The tooth matching component 11 matches the first molar, the second molar and/or the third molar on the mandible in the oral cavity of the subject, and wraps the teeth by means of matching.

Wearing the oral retention device loaded with a medicinal tablet according to this embodiment in the oral cavity, the medicinal tablet may slip off the device during the rapid dissolution of the immediate release layer of the drug after intensive gargle, and may slip off the device during the wearing, but still has a certain use value.

Figure 1C:
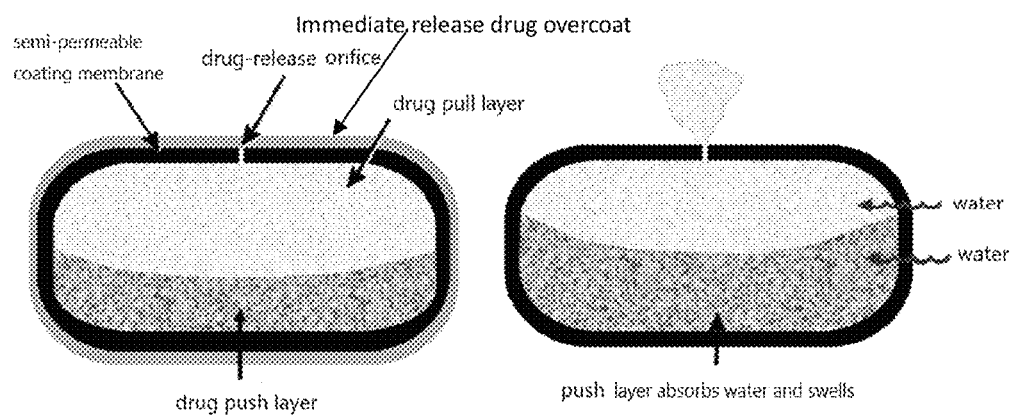
FIG. 1C is a schematic diagram of an ERP, wherein the ERP is a bi-layer osmotic push-pull system with an immediate release drug overcoat.

Example 32 Preparation of Cobalt-Chromium Alloy Back-Insertion Oral Retention Device by Means of 3D Printing The method for preparing the cobalt-chromium alloy back-insertion oral retention device according to this embodiment comprises the following steps:

step 1: obtaining the data of size of the medicinal tablet by scanning with a "3 Shape Dental System" scanner; then, with the software "SolidWorks", designing a drug-loaded component capable of loading the drug part, and creating and saving a "standard attachment" file; and every time an oral retention device is designed in the software "3 Shape Dental System", adding the "standard attachment" and assembling same with the tooth matching component to form an integrated oral retention device;

step 2: performing an intraoral scan:
  a. opening Trios intraoral scanning software;
  b. creating a new patient file, creating a new case file, and confirming;
  c. choosing a research model;
  d. performing scanning on the mandible with the Trios intraoral scanner;
  e. performing scanning on the maxillary;
  f. performing scanning for the occlusal relationship;
  g. post-processing the files to confirm that the scanning data of all molars and premolars are complete and free of defects, and the accurate scanning of occlusion of upper and lower teeth is implemented; and
  h. saving 3OXZ or STL format files;

step 3: designing the device
  a. opening the software 3 Shape Dental System;
  b. creating a new order;
  c. selecting the tooth position;
  d. choosing a basal crown design;
  e. importing the oral scanning teeth data (a STL file);
  f. adding the "standard attachment" and assembling with the tooth matching component to form an integrated oral retention device, in which the opening opens toward the molars in the horizontal direction formed by the molars and the incisors such that the medicinal tablet is located in the horizontal direction formed by the molars and the incisors and can be inserted from the molars toward the incisors; and
  g. after the design is completed, exporting a 3OXZ or STL format file; and step 4: performing 3D printing/in-place polishing;
  a. inputting a CAM program;
  b. turning on an EOS laser accumulation apparatus;
  c. preparing cobalt-chromium alloy metal powder;
  d. downloading the processing program of the product to be produced;
  e. clicking to start processing;
  f. after the processing is completed, opening the compartment door and cleaning by dust collection; and
  g. taking out the device, performing in-place/grinding and polishing. The device is as shown in FIG. 1A, FIG. 1B and FIG. 1C.

As shown in FIG. 22, the cobalt-chromium alloy back-insertion oral retention device prepared according to this embodiment comprises a tooth matching component 11 and a drug-loaded component. The tooth matching component 11 and the drug-loaded component are connected on respective sides, the tooth matching component can be closely attached to a tooth in the oral cavity, and the drug-loaded component can hold at least one medicinal tablet and retain the medicinal tablet in the oral cavity. The medicinal tablet may be a controlled-release preparation, preferably an osmotic pump tablet. The osmotic pump tablet contains an active drug and adjuvants, the active drug has an ingredient of one of levodopa or its ester, carbidopa, baclofen, acyclovir, valaciclovir, ganciclovir, metformin, and gabapentin, or one or two of levodopa or its ester and carbidopa. The drug-loaded component has a cross section in the shape of a circular closed loop. The drug-loaded component may have a reticular structure or a nonreticular structure. The drug-loaded component comprises at least one ring body 31 and at least one retainer 21 that is located at the end, and the ring body 31 forms an opening 311 for insertion of a medicinal tablet. The retainer is of a circular arc hollow shape. The opening faces the molars in the horizontal direction formed by the molars and the incisors, and the medicinal tablet is inserted from the molars toward the incisors in the horizontal direction.

Example 33 Preparation of Cobalt-Chromium Alloy Oral Retention Device by Means of Injection Molding At first, a tooth gypsum model of a patient/volunteer is prepared by means of the traditional model-taking technology; then, by means of a traditional manual process, with dental wax as the material, a dental wax model is manually prepared based on the gypsum model; and finally, with cobalt-chromium porcelain alloy as the material, the oral retention device is prepared by means of a traditional injection molding process.

Example 34 Cobalt-Chromium Alloy Front-Insertion Oral Retention Device Prepared by Means of 3D Printing The oral retention device as shown in FIG. 23 is prepared by the same method as Example 32, only different in the fin step 3, the positions of the ring body and the retainer of the drug-loaded component are opposite to those in Example 32. The ring body 32 of the drug-loaded component 42 forms an opening 321 for insertion of a medicinal tablet, the opening opens toward the incisors in the horizontal direction formed by the molars and the incisors, and the medicinal tablet is inserted from the incisors to the molars in the horizontal direction. The medicinal tablet may be a controlled-release preparation, preferably an osmotic pump tablet.

Although the specific embodiments of the present invention are described above, those skilled in the art should understand that these are merely embodiments, and that various changes or modifications may be made to these embodiments without departing from the principle and essence of the present invention. Therefore, the protection scope of the present invention is defined by the appended claims.

What is claimed is:

1. A method for treating Parkinson's disease in a subject in need thereof, comprising administrating an extended release dosage form to the subject,
    wherein the extended release dosage form has an absorption window at the upper gastrointestinal tract comprising an extended release platform and a retention enabling platform;
    wherein the extended release platform is a pharmaceutical composition comprising a tablet core and a coating membrane, the tablet core comprises a drug-containing layer, and the coating membrane comprises cellulose acetate and copovidone, wherein the weight of the cellulose acetate is 50-70% of the weight of the coating membrane, the weight of the copovidone is 30-50% of the weight of the coating membrane; and
    wherein the retention enabling platform is used for maintaining the extended release platform in the oral cavity, and at least one end of the retention enabling platform is connected with a cover, so that the extended release platform is retained in the retention enabling platform.

2. The method of claim 1, wherein the method comprises the following steps: placing the extended release platform in a personalized retention enabling platform, and fastening the retention enabling platform on the corresponding teeth in the oral cavity; taking out the extended release dosage form after keeping for 4-24 hours, replacing the extended release platform with a new one and fastening the retention enabling platform on the corresponding teeth in the oral cavity again, so that the drug is released continuously and stably.

3. The method of claim 1, wherein the retention enabling platform comprises a personalized retention enabling module and a drug fastened module, the drug fastened module can fix the extended release platform, and the personalized retention enabling module can maintain the drug fastened module in the oral cavity;
    or, the retention enabling platform comprises a tooth matching component and a drug-loaded component, the tooth matching component being connected to the drug-loaded component, wherein the tooth matching component is used to bridge a tooth in the oral cavity and matches with the tooth, and the drug-loaded component can hold at least one medicinal tablet and is used to retain the medicinal tablet in the oral cavity;
    or, the retention enabling platform is prepared by a method comprising 3D printing, injection molding or impression molding;
    or, the retention enabling platform is prepared from one or more oral stable materials, and the oral stable materials comprise oral stable metals and thermoplastic elastomers;
    wherein, the oral stable metal comprises dental titanium, stainless steel, cobalt chromium alloy, cobalt chromium molybdenum alloy, nickel chromium alloy or precious metal, and the thermoplastic elastomer comprises polycaprolactone, ethylene vinyl acetate copolymer, high density polyethylene, polypropylene, polyacrylate, polyurethane, silicone polymer, polyester, poly (styrene-ethylene-butene-styrene), poly (styrene-butadiene-styrene), poly (styrene-isoprene-styrene), or a copolymer of any two or more of the above, or their physical combination;
    or, in the extended release platform, the drug-containing layer comprises active pharmaceutical ingredients and excipients, and the active pharmaceutical ingredient is one or more of levodopa or its ester, carbidopa, baclofen, acyclovir, valacyclovir, ganciclovir, metformin and gabapentin, or one or two of levodopa or its ester and carbidopa.

4. The method of claim 3, wherein the tooth matching component and the drug-loaded component are connected on respective sides; or the drug-loaded component has a reticular structure or a nonreticular structure, and the drug-loaded component has a cross section in the shape of a circular, elliptical, polygonal, or special-shaped closed ring or open ring structure;
    or, the drug fastened module is one or more reservoirs; or, the retention enabling module can fit to any one or more teeth in the oral cavity; or, the retention enabling module is customized to fit and wrap, clamp or insert teeth;
    or, the drug-loaded component comprises at least one ring body and at least one retainer, or the drug-loaded component is constituted by at least one retainer; wherein the ring body has an opening for insertion of a medicinal tablet, and the retainer has a structure for limiting the medicinal tablet in the drug-loaded component; or the tooth is maxillary tooth or mandibular tooth;
    or, the opening faces the molars in a horizontal direction formed by the molars and the incisors, and is used to enable the medicinal tablet to be inserted from the molars toward the incisors in the horizontal direction; or the opening is provided in a direction perpendicular to the horizontal direction such that the medicinal tablet is inserted down from the above in the direction perpendicular to the horizontal direction; or the opening faces the buccal side in a direction perpendicular to the horizontal direction such that the medicinal tablet is inserted from the buccal side to the lingual side in the direction perpendicular to the horizontal direction; or, the tooth is the mandibular molar, mandibular second molar or its anterior and posterior molar;

or, the reservoir has a basket structure; or, the shape of the cross section of the reservoir is polygon, circular closed-loop or circular open-loop, or a combination thereof;

or, at least one end of the reservoir is connected with a cover, so that the extended release platform is maintained in the reservoir; or, at least one end of the reservoir is connected with a strip, so that the extended release platform is maintained in the reservoir;

or, the retention enabling module is customized to fit and wrap, clamp or insert the entire maxillary teeth or the entire mandibular permanent teeth;

or, the retention enabling module is customized to wrap, clamp or insert the mandibular permanent teeth;

or, the retention enabling module is customized to wrap the mandibular molar;

or, the retention enabling module is customized to wrap, clamp or insert the second mandibular molar and its adjacent parts of the first molar and the second bicuspid;

or, the active pharmaceutical ingredient comprises levodopa or carbidopa; or, the excipient is one or more of filler, osmotic agent, hydrophilic polymer, binding agent, lubricant, preservative, flavoring agent, acidifying agent and antioxidant; or, the excipient is one or more of filler, osmotic agent, hydrophilic polymer, binding agent, lubricant and preservative; or, the excipients are filler, osmotic agent, hydrophilic polymer, binding agent, lubricant and preservative;

or, when the pharmaceutically active ingredient comprises levodopa, the weight percentage of the levodopa is 20-70%; when the active ingredient comprises carbidopa, the weight percentage of carbidopa is 0-20% but not 0%; wherein the weight percentage is the weight percentage of each component of the drug-containing layer;

or, when the pharmaceutically active ingredient comprises levodopa, the weight percentage of the levodopa is 30-50%; when the active ingredient comprises carbidopa, the weight percentage of carbidopa is 1-10%; wherein the weight percentage is the weight percentage of each component of the drug-containing layer;

or, in the extended release platform, the tablet core of the pharmaceutical composition further comprises an osmotic push layer, and the osmotic push layer comprises a hydrophilic polymer, an osmotic agent and a binding agent; or, the osmotic push layer comprises a hydrophilic polymer, an osmotic agent, a binding agent, and a lubricant; or, the osmotic push layer comprises a hydrophilic polymer, an osmotic agent, a binding agent, a lubricant and a colorant;

or, wherein in the extended release platform, the coating membrane of the pharmaceutical composition is further overcoated with a drug-containing immediate release overcoat;

the drug-containing immediate release overcoat comprises an active pharmaceutical ingredient and an excipient, the active pharmaceutical ingredient comprises levodopa or carbidopa, and the excipient is one or more of hydroxypropyl cellulose, aspartame and mint flavor; wherein, when the active pharmaceutical ingredient is levodopa, the weight percentage of the levodopa is 0-75% but not 0%, or 23.78-75%;

or, when the active pharmaceutical ingredient is carbidopa, the weight percentage of carbidopa is 0-93% but not 0%, or 26.85-93%;

or, when the excipient of the overcoat comprises hydroxypropyl cellulose, the weight percentage of the hydroxypropyl cellulose is 2-20%, or 10%;

or, when the excipient of the overcoat comprises aspartame, the weight percentage of the aspartame is 0-5%, or 0.9-5%;

or, when the excipient of the overcoat comprises mint flavor, the weight percentage of the mint flavor is 0-5%, or 0.1%; wherein the weight percentage is the weight percentage of each component of the overcoat;

or, wherein in the extended release platform, the weight of the coating membrane is not less than 2.0% of the weight of the tablet core; the coating membrane has one or more orifices, and the diameter of orifice is 0.5 mm-1.0 mm, or 0.5 mm, 0.75 mm and 1.0 mm;

or, the weight of the coating membrane is 2.0-15.0% of the weight of the tablet core; or, the weight of the coating membrane is 4.0-8.0% of the weight of the tablet core.

5. The method of claim 4, wherein in the extended release platform:

when the excipient comprises a filler, the filler is one or more of microcrystalline cellulose, hydroxypropyl cellulose and mannitol, and the weight percentage of the filler is 0-50% but not 0%;

or, when the excipient comprises an osmotic agent, the osmotic agent is one or more of magnesium sulfate, magnesium chloride, sodium chloride, lithium chloride, potassium sulfate, sodium sulfate, mannitol, urea, sorbitol, inositol, sucrose, glucose, and the weight percentage of the osmotic agent is 0-50% but not 0%;

or, when the excipient comprises a hydrophilic polymer, the hydrophilic polymer is one or more of hydroxypropyl cellulose, hydroxypropyl methyl cellulose, carboxymethyl cellulose, polyvinylpyrrolidone and hydroxyethyl cellulose, and the weight percentage of the hydrophilic polymer is 0-50% but not 0%;

or, when the excipient comprises an acidifying agent, the acidifying agent is one or more of citric acid, sodium citrate, potassium citrate, malic acid, fumaric acid, lactic acid, phosphoric acid and tartaric acid, and the weight percentage of the acidifying agent is 0-10% but not 0%;

wherein the weight percentage is the weight percentage of each component of the drug-containing layer;

or, wherein in the extended release platform, the hydrophilic polymer in the osmotic push layer is x-carrageenan, sodium carboxymethyl cellulose or polyethylene oxide, wherein the molecular weight of the hydrophilic polymer is 75,000-7,500,000, and the weight percentage of the hydrophilic polymer is 25-85%;

or, the osmotic agent in the osmotic pump push layer is one or more of magnesium sulfate, magnesium chloride, sodium chloride, lithium chloride, potassium sulfate, sodium sulfate, mannitol, urea, sorbitol, inositol, sucrose, glucose, and the weight percentage of the osmotic agent is 5-65%;

or, when the osmotic push layer comprises a binding agent, the binding agent is one or more of methyl cellulose, hydroxypropyl methyl cellulose, hydroxypropyl cellulose, sodium carboxymethyl cellulose, povidone and gelatin, and the weight percentage of the binding agent is 3-20%;

or, when the osmotic push layer comprises a lubricant, the lubricant is one or more of magnesium stearate, magnesium stearate fumarate, talc, and colloidal silica, and the weight percentage of the lubricant is 0-2% but not 0%;

or, when the osmotic push layer comprises a colorant, the colorant is one or more of iron oxide red, iron oxide yellow, and iron oxide black, and the weight percentage of the colorant is 0-5% but not 0%;

wherein the weight percentage is the weight percentage of each component of the osmotic push layer;

or, wherein in the extended release platform, the osmotic push layer comprises sodium carboxymethyl cellulose, povidone K30, sorbitol, iron oxide red and magnesium stearate;

or comprises sodium carboxymethyl cellulose, hydroxypropyl cellulose, sorbitol, iron oxide red and magnesium stearate;

or, the sodium carboxymethyl cellulose is sodium carboxymethyl cellulose 7H4XF or 9H4XF;

or, the osmotic push layer comprises 25-85 wt % of sodium carboxymethyl cellulose, 5-65 wt % of sorbitol, 3-20 wt % of povidone, 0-5 wt % of iron oxide red and 0.5-2 wt % of magnesium stearate;

or, the osmotic push layer comprises 55 wt % of sodium carboxymethyl cellulose, 34.0-39.0 wt % of sorbitol, 3-20 wt % of povidone or 10 wt % of hydroxylpropyl cellulose, 0.5-5 wt % of iron oxide red and 0.5-2 wt % of magnesium stearate;

or, the osmotic push layer comprises 55 wt % of sodium carboxymethyl cellulose, 39.0 wt % of sorbitol, 5.0 wt % of povidone and 0.5 wt % of iron oxide red and 0.5 wt % of magnesium stearate; or comprises 55 wt % of sodium carboxymethyl cellulose, 34.0 wt % of sorbitol, 10.0 wt % of povidone, 0.5 wt % of iron oxide red and 0.5 wt % of magnesium stearate, or comprises 55 wt % of sodium carboxymethyl cellulose, 34.0 wt % of sorbitol, 10.0 wt % of hydroxypropyl cellulose, 0.5 wt % of iron oxide red and 0.5 wt % of magnesium stearate; wherein the weight percentage is the weight percentage of each component of the osmotic push layer.

6. The method of claim 5, wherein in the extended release platform, the pharmaceutical composition is composed of a drug-containing layer and a coating membrane; the pharmaceutical composition is composed of a drug-containing layer, an osmotic push layer and a coating membrane; or the pharmaceutical composition is composed of a drug-containing layer, an osmotic push layer, a coating membrane, and an overcoat;

or, the drug-containing layer is composed of levodopa, carbidopa, microcrystalline cellulose, mannitol, citric acid, sodium hydroxypropyl methyl cellulose and magnesium stearate; or the drug-containing layer is composed of levodopa, microcrystalline cellulose, hydroxypropyl methyl cellulose and magnesium stearate; or the drug-containing layer is composed of levodopa, carbidopa, mannitol, citric acid and magnesium stearate; or the drug-containing layer is composed of levodopa, carbidopa, hydroxypropyl cellulose, mannitol, citric acid and magnesium stearate; or the drug-containing layer is composed of levodopa, carbidopa, hydroxypropyl cellulose, mannitol, citric acid, and povidone K30; or the drug-containing layer is composed of levodopa, hydroxypropyl cellulose, mannitol, povidone K30, magnesium stearate, mint flavor and aspartame; or the drug-containing layer is composed of levodopa, mannitol, povidone K30 and magnesium stearate; or the drug-containing layer is composed of levodopa, carbidopa, hydroxypropyl cellulose, mannitol, aspartame and magnesium stearate; or the drug-containing layer is composed of levodopa, hydroxypropyl cellulose, mannitol, magnesium stearate, mint flavor and aspartame; or the drug-containing layer is composed of levodopa, hydroxypropyl cellulose, mannitol, povidone K30, magnesium stearate and aspartame; or the drug-containing layer is composed of levodopa, hydroxypropyl cellulose, mannitol, povidone K30, magnesium stearate, and aspartame;

the osmotic push layer is composed of sodium carboxymethyl cellulose, povidone K30, sorbitol, iron oxide red and magnesium stearate, or the osmotic push layer is composed of sodium carboxymethyl cellulose, hydroxypropyl cellulose, sorbitol, iron oxide red and magnesium stearate; or, the sodium carboxymethyl cellulose is sodium carboxymethyl cellulose 7H4XF or 9H4XF;

or, the overcoat is composed of levodopa, carbidopa, hydroxypropyl cellulose, aspartame, and mint flavor; or the overcoat is composed of levodopa, carbidopa, hydroxypropyl cellulose and aspartame; or the overcoat is composed of carbidopa, hydroxypropyl cellulose and aspartame; or the overcoat is composed of levodopa, hydroxypropyl cellulose, and mint flavor.

7. The method of claim 6, wherein in the extended release platform, when the drug-containing layer is composed of levodopa, carbidopa, microcrystalline cellulose, mannitol, citric acid, sodium hydroxypropyl methyl cellulose and magnesium stearate, the weight percentage of levodopa is 40%, the weight percentage of carbidopa is 10.8%, the weight percentage of microcrystalline cellulose is 20%, the weight percentage of mannitol is 18.7%, the weight percentage of citric acid is 5%, the weight percentage of hydroxypropyl methyl cellulose sodium is 5%, and the weight percentage of magnesium stearate is 0.5%, wherein the weight percentage is the weight percentage of each component of the drug-containing layer;

or, when the drug-containing layer is composed of levodopa, microcrystalline cellulose, hydroxypropyl methyl cellulose and magnesium stearate, and the weight percentage of the levodopa is 38%, the weight percentage of microcrystalline cellulose is 50%, the weight percentage of hydroxypropyl methyl cellulose is 10%, and the weight percentage of magnesium stearate is 2%, wherein the weight percentage is the weight percentage of each component of the drug-containing layer;

or, when the drug-containing layer is composed of levodopa, carbidopa, mannitol, citric acid and magnesium stearate, the weight percentage of the levodopa is 19.5%, and the weight percentage of carbidopa is 20%, the weight percentage of mannitol is 50%, the weight percentage of citric acid is 10%, and the weight percentage of magnesium stearate is 0.5%, wherein the weight percentage is the weight percentage of each component of the drug-containing layer;

or, when the drug-containing layer is composed of levodopa, carbidopa, hydroxypropyl cellulose, mannitol, citric acid and magnesium stearate, the weight percentage of the levodopa is 40%, the weight percentage of carbidopa is 10.8%, the weight percentage of hydroxypropyl cellulose is 31%, the weight percentage of mannitol is 12.7%, and the weight percentage of citric acid is 5%, the weight percentage of the magnesium stearate is 0.5%, wherein the weight percentage is the weight percentage of each component of the drug-containing layer;

or, when the drug-containing layer is composed of levodopa, carbidopa, hydroxypropyl cellulose, mannitol, citric acid and povidone K30, the weight percentage of levodopa is 40%, the weight percentage of carbidopa is 10.8%, the weight percentage of hydroxypropyl cellulose is 31%, the weight percentage of mannitol is 12.7%, and the weight percentage of citric acid is 5%, the weight percentage of povidone K30 is 0.5%, wherein the weight percentage is the weight percentage of each component of the drug-containing layer;

or, when the drug-containing layer is composed of levodopa, hydroxypropyl cellulose, mannitol, povidone K30, magnesium stearate, mint flavor and aspartame, the weight percentage of levodopa is 45%, the weight percentage of hydroxypropyl cellulose is 31%, the weight percentage of mannitol is 16%, the weight percentage of povidone K30 is 5%, the weight percentage of the magnesium stearate is 1%, the weight percentage of the mint flavor is 1%, and the weight percentage of the aspartame is 1%, wherein the weight percentage is the weight percentage of each component of the drug-containing layer;

or, when the drug-containing layer is composed of levodopa, mannitol, povidone K30, and magnesium stearate, the weight percentage of levodopa is 70%, the weight percentage of mannitol is 9%, the weight percentage of povidone K30 is 20%, and the weight percentage of magnesium stearate is 1%, wherein the weight percentage is the weight percentage of each component of the drug-containing layer;

or, when the drug-containing layer is composed of levodopa, carbidopa, hydroxypropyl cellulose, mannitol, aspartame and magnesium stearate, the weight percentage of levodopa is 20%, the weight percentage of carbidopa is 20%, the weight percentage of hydroxypropyl cellulose is 50%, the weight percentage of mannitol is 4%, and the weight percentage of aspartame is 5%, the weight percentage of magnesium stearate is 1%, wherein the weight percentage is the weight percentage of each component of the drug-containing layer;

or, when the drug-containing layer is composed of levodopa, hydroxypropyl cellulose, mannitol, povidone K30, magnesium stearate, and aspartame, the weight percentage of levodopa is 45%, the weight percentage of the hydroxypropyl cellulose is 31%, the weight percentage of the mannitol is 16%, the weight percentage of the povidone K30 is 5%, the weight percentage of magnesium stearate is 1%, the weight percentage of the mint flavor is 1%, and the weight percentage of aspartame is 1%, wherein the weight percentage is the weight percentage of each component of the drug-containing layer;

or, when the drug-containing layer is composed of levodopa, hydroxypropyl cellulose, mannitol, povidone K30, magnesium stearate and aspartame, the weight percentage of levodopa is 45%, the weight percentage of the hydroxypropyl cellulose is 31%, the weight percentage of the mannitol is 17%, the weight percentage of the povidone K30 is 5%, the weight percentage of magnesium stearate is 1% and the weight percentage of aspartame is 1%, wherein the weight percentage is the weight percentage of each component of the drug-containing layer;

or, when the drug-containing layer is composed of levodopa, hydroxypropyl cellulose, mannitol, povidone K30, magnesium stearate, mint flavor and aspartame; the weight percentage of the levodopa is 45%, the weight percentage of the hydroxypropyl cellulose is 31%, the weight percentage of the mannitol is 12%, and the weight percentage of the povidone K30 is 5%, the weight percentage of the mint flavor is 5%, the weight percentage of aspartame is 1%, and the weight percentage of magnesium stearate is 1%, wherein the weight percentage is the weight percentage of each component of the drug-containing layer;

or, when the drug-containing layer is composed of levodopa, hydroxypropyl cellulose, mannitol, magnesium stearate, mint flavor and aspartame, the weight percentage of the levodopa is 62.5%, the weight percentage of the hydroxypropyl cellulose is 31%, the weight percentage of the mannitol is 4.5%, the weight percentage of the mint flavor is 0.1%, the weight percentage of aspartame is 0.9% and the weight percentage of magnesium stearate is 1%, wherein the weight percentage is the weight percentage of each component of the drug-containing layer;

or, when the drug-containing layer is composed of levodopa, hydroxypropyl cellulose, mannitol, magnesium stearate, mint flavor and aspartame, the weight percentage of the levodopa is 46.9%, the weight percentage of the hydroxypropyl cellulose is 31%, the weight percentage of the mannitol is 20.1%, the weight percentage of the mint flavor is 0.1%, the weight percentage of aspartame is 0.9%, the weight percentage of magnesium stearate is 1%, wherein the weight percentage is the weight percentage of each component of the drug-containing layer.

8. The method of claim 6, wherein in the extended release platform, the coating membrane is composed of 50 wt % of cellulose acetate membrane and 50 wt % of copovidone VA64; the coating membrane is composed of 70 wt % of cellulose acetate membrane and 30 wt % of copovidone VA64; or the coating membrane is composed of 60 wt % of cellulose acetate membrane and 40 wt % of copovidone VA64; wherein the weight percentage is the weight percentage of each component of the coating membrane;

or, the weight of the coating membrane is 2.0%, 4.2%, 4.5%, 4.6%, 4.8%, 5.0%, 5.9%, 6.5%, 6.7%, 7.0%, 7.7%, 7.9% or 9.7% of the weight of the tablet core.

9. The method of claim 6, wherein in the extended release platform, when the osmotic push layer is composed of sodium carboxymethyl cellulose 7H4XF, povidone K30, sorbitol, iron oxide red and magnesium stearate, the weight percentage of the carboxymethyl cellulose sodium 7H4XF is 55%, the weight percentage of the povidone K30 is 5%, the weight percentage of the sorbitol is 39%, the weight percentage of the iron oxide red is 0.5%, and the weight percentage of the magnesium stearate is 0.5%, wherein the weight percentage is the weight percentage of each component of the osmotic push layer;

the weight percentage of the carboxymethyl cellulose sodium 7H4XF is 55%, the weight percentage of the povidone K30 is 10%, the weight percentage of the sorbitol is 34%, the weight percentage of the iron oxide red is 0.5%, and the weight percentage of the magnesium stearate is 0.5%, wherein the weight percentage is the weight percentage of each component of the osmotic push layer;

the weight percentage of the sodium carboxymethyl cellulose is 85%, the weight percentage of the povidone K30 is 3%, the weight percentage of the sorbitol is 5%, the weight percentage of the iron oxide red is 5%, and the weight percentage of the magnesium stearate is 2%, wherein the weight percentage is the weight percentage of each component of the osmotic push layer;

the weight percentage of the sodium carboxymethyl cellulose is 25%, the weight percentage of the povidone K30 is 9.5%, the weight percentage of the sorbitol is 65% and the weight percentage of the magnesium stearate is 0.5%, wherein the weight percentage is the weight percentage of each component of the osmotic push layer;

the weight percentage of the carboxymethyl cellulose sodium 7H4XF is 60%, the weight percentage of the povidone K30 is 10%, the weight percentage of the sorbitol is 26%, the weight percentage of the iron oxide red is 2%, and the weight percentage of the magnesium stearate is 2%, wherein the weight percentage is the weight percentage of each component of the osmotic push layer;

the weight percentage of the carboxymethyl cellulose sodium 7H4XF is 40%, the weight percentage of the povidone K30 is 20%, the weight percentage of the sorbitol is 36%, the weight percentage of the iron oxide red is 3.5%, and the weight percentage of the magnesium stearate is 0.5%, wherein the weight percentage is the weight percentage of each component of the osmotic push layer;

or, when the osmotic push layer is composed of sodium carboxymethyl cellulose 9H4XF, povidone K30, sorbitol, iron oxide red and magnesium stearate, the weight percentage of sodium carboxymethyl cellulose 9H4XF is 55%, the weight percentage of povidone K30 is 5%, the weight percentage of sorbitol is 39%, and the weight percentage of iron oxide red is 0.5% and the weight percentage of magnesium stearate is 0.5%, wherein the weight percentage is the weight percentage of each component of the osmotic push layer;

or, when the osmotic push layer is composed of sodium carboxymethyl cellulose 7H4XF, hydroxypropyl cellulose, sorbitol, iron oxide red and magnesium stearate, the weight percentage of sodium carboxymethyl cellulose 7H4XF is 55%, the weight percentage of hydroxypropyl cellulose is 10%, the weight percentage of sorbitol is 34%, the weight percentage of the iron oxide red is 0.5% and the weight percentage of the magnesium stearate is 0.5%, wherein the weight percentage is the weight percentage of each component of the osmotic push layer.

10. The method of claim 6, wherein in the extended release platform, when the overcoat is composed of levodopa, carbidopa, hydroxypropyl cellulose, aspartame and mint flavor, the weight percentage of the levodopa is 23.78%, the weight percentage of the carbidopa is 64.22%, the weight percentage of the hydroxypropyl cellulose is 10%, and the weight percentage of the aspartame is 1%, the weight percentage of the mint flavor is 1%; or the weight percentage of the levodopa is 54%, the weight percentage of the carbidopa is 35%, the weight percentage of the hydroxypropyl cellulose is 10%, and the weight percentage of the aspartame is 0.9%, the weight percentage of the mint flavor is 0.1%; or the weight percentage of the levodopa is 42.8%, the weight percentage of the carbidopa is 46.2%, the weight percentage of the hydroxypropyl cellulose is 10%, and the weight percentage of the aspartame is 0.9%, and the weight percentage of the mint flavor is 0.1%, wherein the weight percentage is the weight percentage of each component of the overcoat;

when the overcoat is composed of levodopa, carbidopa, hydroxypropyl cellulose, aspartame and mint flavor, the weight percentage of the levodopa is 62.15%, the weight percentage of the carbidopa is 26.85%, the weight percentage of the hydroxypropyl cellulose is 10%, the weight percentage of the aspartame is 0.9%, and the weight percentage of the mint flavor is 0.1%;

or, the weight percentage of the levodopa is 42.8%, the weight percentage of the carbidopa is 46.2%, the weight percentage of the hydroxypropyl cellulose is 10%, the weight percentage of the aspartame is 0.9%, the weight percentage of the mint flavor is 0.1%, or the weight percentage of the levodopa is 28.2%, and the weight percentage of the carbidopa is 60.8%, the weight percentage of the hydroxypropyl cellulose is 10%, the weight percentage of the aspartame is 0.9%, and the weight percentage of the mint flavor is 0.1%, wherein the weight percentage is the weight percentage of each component of the overcoat;

or, when the overcoat is composed of carbidopa, hydroxypropyl cellulose and aspartame, the weight percentage of carbidopa is 93%, the weight percentage of hydroxypropyl cellulose is 2% and the weight percentage of aspartame is 5%, wherein the weight percentage is the weight percentage of each component of the overcoat;

or, when the overcoat is composed of levodopa, hydroxypropyl cellulose and mint flavor, the weight percentage of the levodopa is 75%, the weight percentage of the hydroxypropyl cellulose is 20%, and the weight percentage of the mint flavor is 5%, wherein the weight percentage is the weight percentage of each component of the overcoat;

or, when the overcoat is composed of levodopa, carbidopa, hydroxypropyl cellulose and aspartame, the weight percentage of levodopa is 24%, the weight percentage of carbidopa is 65%, the weight percentage of hydroxypropyl cellulose is 10% and the weight percentage of aspartame is 1%, wherein the weight percentage is the weight percentage of each component of the overcoat;

or, the weight gain of the overcoat relative to the tablet core is 12.9% or 13.2% or 15.7% or 21.0% by weight.

11. The method of claim 6, wherein in the extended release platform, the pharmaceutical composition is composed of a drug-containing layer and a coating membrane, the drug containing layer is composed of 40 wt % of levodopa, 10.8 wt % of carbidopa, 20 wt % of microcrystalline cellulose, 18.7 wt % of mannitol, 5 wt % of citric acid, 5 wt % of hydroxypropyl methyl cellulose sodium and 0.5 wt % of magnesium stearate, wherein the weight percentage is the weight percentage of each component of the drug-containing layer; the coating membrane is composed of 50 wt % of cellulose acetate membrane and 50 wt % of copovidone VA64, wherein the weight percentage is the weight percentage of each component of the coating membrane; the weight of the coating membrane is 2.0% of the weight of the tablet core;

or, the pharmaceutical composition is composed of a drug-containing layer and a coating membrane, the drug-containing layer is composed of 38 wt % of levodopa, 50 wt % of microcrystalline cellulose, 10 wt % of hydroxypropyl methyl cellulose and 2 wt % of magnesium stearate, wherein the weight percentage is the weight percentage of each component of the drug-containing layer; the coating membrane is composed of 50 wt % of cellulose acetate membrane and 50 wt % of copovidone VA64, wherein the weight percentage is the weight percentage of each component of the coating membrane, and the weight of the coating membrane is 4.5% of the weight of tablet core;

or, the pharmaceutical composition is composed of a drug-containing layer and a coating membrane, the drug-containing layer comprises 19.5 wt % of levodopa, 20 wt % of carbidopa, 50 wt % of mannitol, 10 wt % of citric acid and 0.5 wt % of magnesium stearate, wherein the weight percentage is the weight percentage of each component of the drug-containing layer; the coating membrane is composed of 50 wt % of cellulose acetate membrane and 50 wt % of copovidone VA64, wherein the weight percentage is the weight percentage of each component of the coating membrane, and the weight of the coating membrane is 4.5% of the weight of tablet core;

or, the pharmaceutical composition is composed of a drug-containing layer, an osmotic push layer, and a coating membrane, and the drug-containing layer is composed of 40 wt % of levodopa, 10.8 wt % of carbidopa, 31 wt % of hydroxypropyl cellulose, 12.7 wt % of mannitol, 5 wt % of citric acid and 0.5 wt % of magnesium stearate, wherein the weight percentage is the weight percentage of each component of the drug-containing layer; the osmotic push layer is composed of 55 wt % of sodium carboxymethyl cellulose 7H4XF or 9H4 XF, 5 wt % of povidone K30, 39 wt % of sorbitol, 0.5 wt % of iron oxide red and 0.5 wt % of magnesium stearate, wherein the weight percentage is the weight percentage of each component of the osmotic push layer; the coating membrane is composed of 70 wt % of cellulose acetate membrane and 30 wt % of copovidone VA64, wherein the weight percentage is the weight percentage of each component of the coating membrane; the weight of the coating membrane is 2.0%, 4.0% or 5.0% of the weight of the tablet core;

or, the pharmaceutical composition is composed of a drug-containing layer, an osmotic push layer, and a coating membrane, the drug-containing layer is composed of 40 wt % of levodopa, 10.8 wt % of carbidopa, 31 wt % of hydroxypropyl cellulose, 12.7 wt % of mannitol, 5 wt % of citric acid and 0.5 wt % of povidone K30, wherein the weight percentage is the weight percentage of each component of the drug-containing layer; the osmotic push layer is composed of 55 wt % of sodium carboxymethyl cellulose 7H4XF, 5 wt % of povidone K30, 39 wt % of sorbitol, 0.5 wt % of iron oxide red, and 0.5 wt % of magnesium stearate, wherein the weight percentage is the weight percentage of each component of the osmotic push layer; the coating membrane is composed of 60 wt % of cellulose acetate membrane and 40% copovidone VA64, wherein the weight percentage is the weight percentage of each component of the coating membrane; and the weight of the coating membrane is 5.0% of the weight of the tablet core;

or, the pharmaceutical composition is composed of a drug-containing layer, an osmotic push layer, and a coating membrane, the drug-containing layer is composed of 45 wt % of levodopa, 31 wt % of hydroxypropyl cellulose, 16 wt % of mannitol, 5 wt % of povidone K30, and 1 wt % of magnesium stearate, 1 wt % of mint flavor and 1 wt % of aspartame, wherein the weight percentage is the weight percentage of each component of the drug-containing layer; the osmotic push layer is composed of 55 wt % of sodium carboxymethyl cellulose 7H4 XF, 10 wt % of povidone K30, 34 wt % of sorbitol, 0.5 wt % of iron oxide red and 0.5 wt % of magnesium stearate, wherein the weight percentage is the weight percentage of each component of the osmotic push layer; the coating membrane is composed of 60 wt % of cellulose acetate membrane and 40 wt % of copovidone VA64, wherein the weight percentage is the weight percentage of each component of the coating membrane; and the weight of the coating membrane is 4.2%, 6.7% or 9.7% of the weight of the tablet core;

or, the pharmaceutical composition is composed of a drug-containing layer, an osmotic push layer, and a coating membrane, the drug-containing layer is composed of 45 wt % of levodopa, 31 wt % of hydroxypropyl cellulose, 16 wt % of mannitol, 5 wt % of povidone K30, 1 wt % of magnesium stearate, 1 wt % of mint flavor and 1 wt % of aspartame, wherein the weight percentage is the weight percentage of each component of the drug-containing layer; the osmotic push layer is composed of 55 wt % of sodium carboxymethyl cellulose 7H4XF, 10 wt % of povidone K30, 34 wt % of sorbitol, 0.5 wt % of iron oxide red and 0.5 wt % of magnesium stearate, wherein the weight percentage is the weight percentage of each component of the osmotic push layer; the coating membrane is composed of 70 wt % of cellulose acetate membrane and 30 wt % of copovidone VA64, wherein the weight percentage is the weight percentage of each component of the coating membrane; and the weight of the coating membrane is 4.6% or 7.9% of the weight of the tablet core;

or, the pharmaceutical composition is composed of a drug-containing layer, an osmotic push layer, and a coating membrane, the drug-containing layer is composed of 70 wt % of levodopa, 9 wt % of mannitol, 20 wt % of povidone K30, 1 wt % of magnesium stearate, wherein the weight percentage is the weight percentage of each component of the drug-containing layer; the osmotic push layer is composed of 85 wt % of sodium carboxymethyl cellulose, 3 wt % of povidone K30, 5 wt % of sorbitol, 5 wt % of iron oxide red and 2 wt % of magnesium stearate, wherein the weight percentage is the weight percentage of each component of the osmotic push layer; the coating membrane is composed of 70 wt % of cellulose acetate membrane and 30 wt % of copovidone VA64, wherein the weight percentage is the weight percentage of each component of the coating membrane; and the weight of the coating membrane is 4.5% of the weight of the tablet core;

or, the pharmaceutical composition is composed of a drug-containing layer, an osmotic push layer, a coating membrane and an overcoat, the drug-containing layer is composed of 45 wt % of levodopa, 31 wt % of hydroxypropyl cellulose, 16 wt % of mannitol, 5 wt % of povidone K30, 1 wt % of magnesium stearate, 1 wt % of mint flavor and 1 wt % of aspartame, wherein the weight percentage is the weight percentage of each component of the drug-containing layer; the osmotic push layer is composed of 55 wt % of sodium carboxymethyl cellulose 7H4XF, 10 wt % of povidone K30, 34 wt % of sorbitol, 0.5 wt % of iron oxide red and 0.5 wt % of magnesium stearate, wherein the weight percentage is the weight percentage of each component of the osmotic push layer; the coating membrane is composed of 70 wt % of cellulose acetate membrane and 30 wt % of copovidone VA64, wherein the weight percentage is the weight percentage of each component of the coating membrane; and the weight of the coating membrane is 4.8% or 7.7% of the weight of the tablet core, the overcoat is composed of 23.78 wt % of levodopa, 64.22 wt % of carbidopa, 10 wt % of hydroxypropyl cellulose, 1 wt % of aspartame and 1 wt % of mint flavor immediate release composition, wherein the weight percentage is the weight percentage of each component of the overcoat, and the weight gain of the overcoat relative to the tablet core is 13.2% and 12.9% by weight, respectively;

or, the pharmaceutical composition is composed of a drug-containing layer, an osmotic push layer, a coating membrane and an overcoat, the drug-containing layer is composed of 45 wt % of levodopa, 31 wt % of hydroxypropyl cellulose, 17 wt % of mannitol, 5 wt % of povidone K30, 1 wt % of magnesium stearate and 1 wt % of aspartame, wherein the weight percentage is the weight percentage of each component of the drug-containing layer; the osmotic push layer is composed of 60 wt % of sodium carboxymethyl cellulose 7H4XF, 10 wt % of povidone K30, 26 wt % of sorbitol, 2 wt % of iron oxide red and 2 wt % of magnesium stearate, wherein the weight percentage is the weight percentage of each component of the osmotic push layer; the coating membrane is composed of 70 wt % of cellulose acetate membrane and 30 wt % of copovidone VA64, wherein the weight percentage is the weight percentage of each component of the coating membrane; and the weight of the coating membrane is 4.8% of the weight of the tablet core; the overcoat is composed of 93 wt % of carbidopa (CD), 2 wt % of hydroxypropyl cellulose and 5 wt % of aspartame immediate release composition, wherein the weight percentage is the weight percentage of each component of the overcoat, and the weight gain of the overcoat relative to the tablet core is 13.2% by weight;

or, the pharmaceutical composition is composed of a drug-containing layer, an osmotic push layer, a coating membrane and an overcoat, the drug-containing layer is composed of 45 wt % of levodopa, 31 wt % of hydroxypropyl cellulose, 12 wt % of mannitol, 5 wt % of povidone K30, 5 wt % of mint flavor, 1 wt % of aspartame and 1 wt % of magnesium stearate, wherein the weight percentage is the weight percentage of each component of the drug-containing layer; the osmotic push layer is composed of 40 wt % of sodium carboxymethyl cellulose 7H4XF, 20 wt % of povidone K30, 36 wt % of sorbitol, 3.5 wt % of iron oxide red and 0.5 wt % of magnesium stearate, wherein the weight percentage is the weight percentage of each component of the osmotic push layer; the coating membrane is composed of 70 wt % of cellulose acetate membrane and 30 wt % of copovidone VA64, wherein the weight percentage is the weight percentage of each component of the coating membrane; and the weight of the coating membrane is 4.8% of the weight of the tablet core; the overcoat is composed of 75 wt % of levodopa, 20 wt % of hydroxypropyl cellulose and 5 wt % of mint flavor immediate release composition, wherein the weight percentage is the weight percentage of each component of the overcoat, and the weight gain of the overcoat relative to the tablet core is 13.2% by weight;

or, the pharmaceutical composition is composed of a drug-containing layer, an osmotic push layer, a coating membrane and an overcoat, the drug-containing layer is composed of 62.5 wt % of levodopa, 31 wt % of hydroxypropyl cellulose, 4.5 wt % of mannitol, 0.1 wt % of mint flavor, 0.9 wt % of aspartame and 1 wt % of magnesium stearate, wherein the weight percentage is the weight percentage of each component of the drug-containing layer; the osmotic push layer is composed of 55 wt % of sodium carboxymethyl cellulose 7H4XF, 10 wt % of hydroxypropyl cellulose, 34 wt % of sorbitol, 0.5 wt % of iron oxide red and 0.5 wt % of magnesium stearate, wherein the weight percentage is the weight percentage of each component of the osmotic push layer; the coating membrane is composed of 70 wt % of cellulose acetate membrane and 30 wt % of copovidone VA64, wherein the weight percentage is the weight percentage of each component of the coating membrane; and the weight of the coating membrane is 6.5% of the weight of the tablet core, the overcoat is composed of 62.15 wt % of levodopa, 26.85 wt % of carbidopa, 10 wt % of hydroxypropyl cellulose, 0.9 wt % of aspartame and 0.1 wt % of mint flavor immediate release composition, wherein the weight percentage is the weight percentage of each component of the overcoat, and the weight gain of the overcoat relative to the tablet core is 21.0% by weight;

or, the pharmaceutical composition is composed of a drug-containing layer, an osmotic push layer, a coating membrane and an overcoat, the drug-containing layer is composed of 46.9 wt % of levodopa, 31 wt % of hydroxypropyl cellulose, 20.1 wt % of mannitol, 0.1 wt % of mint flavor, 0.9 wt % of aspartame and 1 wt % of magnesium stearate, wherein the weight percentage is the weight percentage of each component of the drug-containing layer; the osmotic push layer is composed of 55 wt % of sodium carboxymethyl cellulose 7H4XF, 10 wt % of hydroxypropyl cellulose, 34 wt % of sorbitol, 0.5 wt % of iron oxide red and 0.5 wt % of magnesium stearate, wherein the weight percentage is the weight percentage of each component of the osmotic push layer; the coating membrane is composed of 70 wt % of cellulose acetate membrane and 30 wt % of copovidone VA64, wherein the weight percentage is the weight percentage of each component of the coating membrane; and the weight of the coating membrane is 6.5% of the weight of the tablet core, the overcoat is composed of 62.15 wt % of levodopa, 26.85 wt % of carbidopa, 10 wt % of hydroxypropyl cellulose, 0.9 wt % of aspartame and 0.1 wt % of mint flavor immediate release composition, wherein the weight percentage is the weight percentage of each component of the overcoat, and the weight gain of the overcoat relative to the tablet core is 15.7% by weight;

or, the pharmaceutical composition is composed of a drug-containing layer, an osmotic push layer, a coating membrane and an overcoat; wherein the drug-containing layer is composed of 45 wt % of levodopa, 31 wt % of hydroxypropyl cellulose, 17 wt % of mannitol, 5 wt % of povidone K30, 1 wt % of magnesium stearate and 1 wt % of aspartame, wherein the weight percentage is the weight percentage of each component of the drug-containing layer; the osmotic push layer is composed of 55 wt % of sodium carboxymethyl cellulose 7H4XF, 10 wt % of hydroxypropyl cellulose, 34 wt % of sorbitol, 0.5 wt % of iron oxide red and 0.5 wt % of magnesium stearate, wherein the weight percentage is the weight percentage of each component of the osmotic push layer; the coating membrane is composed of 70 wt % of cellulose acetate membrane and 30 wt % of copovidone VA64, wherein the weight percentage is the weight percentage of each component of the coating membrane; wherein, the cellulose acetate is a cellulose acetate membrane containing 39.8 wt % of acetyl, and the weight of the coating membrane is 5.9% of the weight of the tablet core; and, the overcoat is composed of 24 wt % of levodopa, 65 wt % of carbidopa, 10 wt % of hydroxypropyl cellulose and 1 wt % of aspartame, wherein the weight percentage is the weight percentage of each component of the overcoat, the weight of the overcoat is 13.1% of the total weight of the tablet core and the coating membrane;

or, the pharmaceutical composition is composed of a drug-containing layer, an osmotic push layer, a coating membrane and an overcoat; the drug-containing layer is composed of 45 wt % of levodopa, 31 wt % of hydroxypropyl cellulose, 22 wt % of mannitol, 0.9 wt % of aspartame, 1 wt % of magnesium stearate and 0.1 wt % of mint flavor, wherein the weight percentage is the weight percentage of each component of the drug-containing layer; the osmotic push layer is composed of 55 wt % of sodium carboxymethyl cellulose 7H4XF, 10 wt % of hydroxypropyl cellulose, 34 wt % of sorbitol, 0.5 wt % of iron oxide red and 0.5 wt % of magnesium stearate, wherein the weight percentage is the weight percentage of each component of the osmotic push layer; the coating membrane is composed of 70 wt % of cellulose acetate membrane and 30 wt % of copovidone VA64, wherein the weight percentage is the weight percentage of each component of the coating membrane; wherein, the cellulose acetate is a cellulose acetate membrane containing 39.8 wt % of acetyl, and the weight of the coating membrane is 6.5% of the weight of the tablet core; and, the overcoat is composed of 54 wt % of levodopa, 35 wt % of carbidopa, 10 wt % of hydroxypropyl cellulose, 0.9 wt % of aspartame and 0.1 wt % of mint flavor, wherein the weight percentage is the weight percentage of each component of the overcoat, the weight of the overcoat is 13.1% of the total weight of the tablet core and the coating membrane;

or, the pharmaceutical composition is composed of a drug-containing layer, an osmotic push layer, a coating membrane and an overcoat; the drug-containing layer is composed of 45 wt % of levodopa, 31 wt % of hydroxypropyl cellulose, 22 wt % of mannitol, 0.9 wt % of aspartame, 1 wt % of magnesium stearate and 0.1 wt % of mint flavor, wherein the weight percentage is the weight percentage of each component of the drug-containing layer; the osmotic push layer is composed of 55 wt % of sodium carboxymethyl cellulose 7H4XF, 10 wt % of hydroxypropyl cellulose, 34 wt % of sorbitol, 0.5 wt % of iron oxide red and 0.5 wt % of magnesium stearate, wherein the weight percentage is the weight percentage of each component of the osmotic push layer; the coating membrane is composed of 70 wt % of cellulose acetate membrane and 30 wt % of copovidone VA64, wherein the weight percentage is the weight percentage of each component of the coating membrane; wherein, the cellulose acetate is a cellulose acetate membrane containing 39.8 wt % of acetyl, and the weight of the coating membrane is 7.0% of the weight of the tablet core; and, the overcoat is composed of 42.8 wt % of levodopa, 46.2 wt % of carbidopa, 10 wt % of hydroxypropyl cellulose, 0.9 wt % of aspartame and 0.1 wt % of mint flavor, wherein the weight percentage is the weight percentage of each component of the overcoat, the weight of the overcoat is 13.1% of the total weight of the tablet core and the coating membrane;

or, the pharmaceutical composition is composed of a drug-containing layer, an osmotic push layer, a coating membrane and an overcoat; the drug-containing layer is composed of 45 wt % of levodopa, 31 wt % of hydroxypropyl cellulose, 22 wt % of mannitol, 0.9 wt % of aspartame, 1 wt % of magnesium stearate and 0.1 wt % of mint flavor, wherein the weight percentage is the weight percentage of each component of the drug-containing layer; the osmotic push layer is composed of 55 wt % of sodium carboxymethyl cellulose 7H4XF, 10 wt % of hydroxypropyl cellulose, 34 wt % of sorbitol, 0.5 wt % of iron oxide red and 0.5 wt % of magnesium stearate, wherein the weight percentage is the weight percentage of each component of the osmotic push layer; the coating membrane is composed of 70 wt % of cellulose acetate membrane and 30 wt % of copovidone VA64, wherein the weight percentage is the weight percentage of each component of the coating membrane; wherein, the cellulose acetate is a cellulose acetate membrane containing 39.8 wt % of acetyl, and the weight of the coating membrane is 9.0% of the weight of the tablet core; and, the overcoat is composed of 28.2 wt % of levodopa, 60.8 wt % of carbidopa, 10 wt % of hydroxypropyl cellulose, 0.9 wt % of aspartame and 0.1 wt % of mint flavor, wherein the weight percentage is the weight percentage of each component of the overcoat, the weight of the overcoat is 13.1% of the total weight of the tablet core and the coating membrane.

12. The method of claim 1, wherein the pharmaceutical composition is an osmotic pump extended release drug delivery system, wherein, the osmotic pump extended release drug delivery system is an extended release tablet.

13. The method of claim 12, wherein the extended release tablet is a cylinder with a diameter of 5-10 mm and a height of 5-30 mm, or a caplet with a length of 10-25 mm and a width of 5-10 mm; or, each of the extended release tablets contains 62.5 mg carbidopa (CD) and 500 mg levodopa (LD), or 62.5 mg CD and 375 mg LD, or 62.5 mg carbidopa and 250 mg levodopa, or 50 mg carbidopa and 500 mg levodopa, or 37.5 mg carbidopa and 375 mg levodopa.

14. The method of claim 4, wherein the ring body is an open ring body or a closed ring body; or, the ring body is a circular, elliptical, polygonal, or special-shaped closed ring body or open ring body;

or, the retainer is of a circular arc hollow or solid shape, or the retainer is formed by connecting a closed ring body and a semicircular part perpendicular to the closed ring body;

or the retainer abuts with the ring body, or the retainer and the ring body are arranged at an interval; or, the retainer and the ring body are abutted by means of integral molding or are connected together by a connecting structure;

or, the retainer is provided as one retainer that is located on the incisor side in the horizontal direction formed by the molars and the incisors; or the ring body is provided as one ring body that is located on the molar side in the horizontal direction formed by the molars and the incisors;

or, the tooth matching component can match with any one or more teeth in the oral cavity, or the tooth matching component has a length equal to the length of 2-5 teeth;

wherein, the teeth are mandibular permanent teeth, or mandibular molars, or the first molar and the second molar, or the first molar, the second molar and the second premolar, or the first molar, the second molar and the third molar, or the first molar, the second molar, the third molar and the second premolar on the mandible;

or, the tooth matching component is wrapped, embedded, fitted, or inserted into the tooth that matches with the tooth matching component;

or, the material of the oral retention device is an oral stable material, which is selected from oral stable metal or thermoplastic elastomer;

wherein, the oral stable metal is selected from one of titanium, stainless steel, cobalt-chromium alloy, cobalt-chromium-molybdenum alloy or precious metal for dental use, and the thermoplastic elastomer is selected from copolymers of one or two of polycaprolactone, ethylene-vinyl acetate copolymer, high-density polyethylene, polypropylene, polyacrylate, polyurethane, silicon polymer, polyester, poly(styrene-ethylene-butylene-styrene), poly(styrene-butadiene-styrene), and poly(styrene-isoprene-styrene); and or, the materials of the tooth matching component and the drug-loaded component are cobalt-chromium alloy.

15. The method of claim 1, wherein the tablet core of the pharmaceutical composition further comprises an osmotic push layer, and the osmotic push layer comprising a hydrophilic polymer, an osmotic agent and a binding agent.

16. The method of claim 15, wherein the drug-containing layer comprises active pharmaceutical ingredients and excipients, and the active pharmaceutical ingredient is one or two of levodopa or its ester and carbidopa.

17. The method of claim 15, wherein the copovidone is prepared by the following method comprising the following steps: polymerizing vinyl pyrrolidone and vinyl acetate, wherein the molar ratio of the vinyl pyrrolidone and vinyl acetate is 40:60-80:20.

18. The method of claim 3, wherein the 3D printing comprises the following steps:
(1) in design software 3Shape Dental System, adding a saved drug-loaded component plan, assembling the plan with a tooth matching component plan to form an integrated oral retention device plan, and exporting a 3D printable file;
(2) importing the 3D printable file into a 3D printer, and printing the oral retention device.

19. The method of claim 18, wherein the 3D printing uses a laser sintering process;
or, before the step (1), the following steps are included:
(0) in software SolidWorks, designing the drug-loaded component plan according to the data of the size of the medicinal tablet, and saving the plan;
or in the design software 3 Shape Dental System, designing the tooth matching component plan according to the data of the size of teeth of the subject.

* * * * *